US007582650B2

United States Patent
DeCorte et al.

(10) Patent No.: US 7,582,650 B2
(45) Date of Patent: *Sep. 1, 2009

(54) TRICYCLIC OPIOID MODULATORS

(75) Inventors: Bart DeCorte, Southampton, PA (US); Li Liu, Doylestown, PA (US); Mark McDonnell, Lansdale, PA (US); Jim McNally, Souderton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/424,311

(22) Filed: Jun. 15, 2006

(65) Prior Publication Data

US 2006/0287297 A1  Dec. 21, 2006

Related U.S. Application Data

(60) Provisional application No. 60/691,101, filed on Jun. 16, 2005.

(51) Int. Cl.
C07D 221/22 (2006.01)
A61K 31/46 (2006.01)
(52) U.S. Cl. .................................. 514/299; 546/112
(58) Field of Classification Search ................ 546/112; 514/299
See application file for complete search history.

(56) References Cited

U.S. PATENT DOCUMENTS

| 2,368,006 | A | 1/1945 | Cusic |
| 2,784,185 | A | 3/1957 | Schuler |
| 2,901,478 | A | 8/1959 | Schuler |
| 3,179,665 | A | 4/1965 | Schmutz |
| 3,305,547 | A | 2/1967 | Stach et al. |
| 3,470,188 | A | 9/1969 | Kaiser et al. |
| 3,557,287 | A | 1/1971 | Berde et al. |
| 3,931,232 | A | 1/1976 | Bender et al. |
| 3,987,042 | A | 10/1976 | Gueremy et al. |
| 4,086,350 | A | 4/1978 | Zirkle |
| 4,275,209 | A | 6/1981 | Lassen et al. |
| 4,356,184 | A | 10/1982 | Deason et al. |
| 4,666,907 | A | 5/1987 | Fortin et al. |
| 4,777,177 | A | 10/1988 | Traber et al. |
| 5,502,049 | A | 3/1996 | Garret et al. |
| 6,004,983 | A | 12/1999 | Andersen et al. |
| 6,114,354 | A | 9/2000 | Andersen et al. |
| 6,153,626 | A | 11/2000 | Pelcman et al. |
| 7,060,711 | B2 | 6/2006 | Lubbert et al. |
| 2003/0018447 | A1 | 1/2003 | Florschuetz |
| 2003/0166672 | A1 | 9/2003 | Lubbert et al. |
| 2005/0009860 | A1* | 1/2005 | Carson et al. ........... 514/297 |
| 2006/0030585 | A1* | 2/2006 | Dax et al. ............... 514/304 |
| 2006/0135522 | A1 | 6/2006 | Carson et al. |
| 2006/0135524 | A1* | 6/2006 | Carson et al. .......... 514/252.04 |
| 2006/0135763 | A1 | 6/2006 | Coats et al. |
| 2006/0148823 | A1 | 7/2006 | Coats et al. |
| 2006/0287297 | A1 | 12/2006 | DeCorte et al. |

FOREIGN PATENT DOCUMENTS

| DE | 2009555 | 10/1970 |
| EP | 0005607 B1 | 11/1979 |
| EP | 1049676 B1 | 11/2000 |
| EP | 1306376 A | 5/2003 |
| EP | 1321169 A1 | 6/2003 |
| FR | 2290202 A1 | 6/1976 |
| GB | 1128734 | 10/1968 |
| WO | WO 9828275 A1 | 7/1998 |
| WO | WO 9900376 A1 | 1/1999 |
| WO | WO 0146191 A1 | 6/2001 |
| WO | WO 0166543 A2 | 9/2001 |
| WO | WO 0172303 A1 | 10/2001 |
| WO | WO 0236573 A2 | 5/2002 |
| WO | WO 0248122 A2 | 6/2002 |
| WO | WO 03035646 A2 | 5/2003 |
| WO | WO 2004/026030 A2 | 4/2004 |
| WO | WO 2004035541 A1 | 4/2004 |
| WO | WO 2004/092165 A | 10/2004 |
| WO | WO 2005/003131 A | 1/2005 |

OTHER PUBLICATIONS

Hutchins, R.O. et. al. J. Org. Chem. 1977, 42, 82-91.*
Gribble, G. in Encyclopedia of Reagents for Organic Synthesis "Sodium Triacetoxy Borohydride" online "http://www.mrw.interscience.wiley.com/eros/articles/rs112/sect0.html" Apr. 24, 2007.*
Quock et. al., "The d-Opioid Receptor: Molecular Pharmacology, Signal Transduction, and the Determination of Drug Efficacy" Pharmacological Reviews 1999, 51(3), 503-532.*
Ananthan, S. The AAPS Journal 2006, 8 (1), E118-E125.*
Structures in copending U.S. Appl. No. 11/195,231 (created by examiner).*
Tao et. al. Bioorganic & Medicinal Chemistry Letters 2006 16, 938-942.*
Calo et. al. British Journal of Pharmacology 2002, 136, 303-311.*
Chang et. al. Molecular Pharmacology, 1984, 26, 484-488.*
Erchegyi et. al. Journal of Medicinal Chemistry 2003, 46, 5587-5596.*
Kruzsynski et. al. Journal of Peptide Research 2005, 66, 125-131.*
Dorwald F. A. Side Reactions in Organic Synthesis, 2005, Wiley: VCH, Weinheim p. IX of Preface.*
Pozharskii et. al. Heterocycles in Life and Society Wiley, 1997, pp. 1-6.*
West, Anthony R., Solid State Chemistry and its Applications, Wiley, New York, 1988, pp. 358 & 365.*

(Continued)

Primary Examiner—Rita J Desai
Assistant Examiner—David K O'Dell

(57) ABSTRACT

The invention is directed to compounds of Formula (I) useful as delta and mu opioid receptor modulators. Pharmaceutical and veterinary compositions and methods of treating mild to severe pain and various diseases using compounds of the invention are also described.

17 Claims, No Drawings

OTHER PUBLICATIONS

John R. Carson et. al. "N-Alkyl-4-[(8-azabicyclo[3.2.1]-oct-3-ylidene)phenylmethyl]-benzamides, mu and delta opioid agonists" Bioorganic & Medicinal Chemistry Letters 2004, 14, 2113-2116.*
Furness et. al. Journal of Medicinal Chemistry 2000, 43, 3193-3196.*
Jones, M. Organic Chemistry Norton: New York, 1997, pp. 578-591.*
PCT International Search Report, PCT/US2006/023429, Dec. 1, 2006.
Berge, S.M. et al.: Pharmaceutical Salts; J. of Pharmaceutical Sciences (1977) 66(1): 1-19.
Bidlack, J.M. et al.: 8-Carboxamidocyclazocine: A Long-Acting, Novel Benzomorphan; The J. of Pharm. & Exper. Therapeutics (2002) 302(1): 374-380.
Biemans, H.A.M. et al.: "Hexapyrrolylbenzene and Octapyrrolylnaphthalene"; J. Org. Chem. (1996) 61: 9012-9015.
Boyd, R.E. et al.: Synthesis and Binding Affinities of 4-Diarylaminotropanes, a New Class of Delta Opioid Agonists; Bioorg. & Med. Chem. Letters (2000) 10: 1109-1111.
Commercial 2-Bromo-Phenols from Sigma-Aldrich.
Commercial 4-piperidinones.
Connor, M. et al.: Opioid Receptor Signalling Mechanisms; Clinical and Exper. Pharmacology and Physiology (1999) 26: 493-499.
Dorwald, F.Z.: Side Reactions in Organic Synthesis (2005) Wiley: VCH, Weinheim p. 1X of Preface: 1-15.
Dörwald, F.Z.: Side Reactions in Organic Synthesis (2005) Wiley: VCH, Weinheim p. 1X of Preface & Chapter 8: 279-308.
Frontier Scientific Catalog, Logan, Utah, online http://www.frontiersci.com/browse.php?browse=Boronic%20acid : 39 pgs.
Frontier Scientific Catalog (Logan, UT) Advanced Discovery Chemicals Pure (*and not so*) Simple 2006; Discover Chemicals A-F, H-I, M-N, P-Q and T.
Gilbert, P.E. et al.: The Effects of Morphine- and Nalorphine-Like Drugs in the Nondependent, Morphine-Dependent and Cyclazocine-Dependent Chronic Spinal Dog; The J. of Pharm. And Exp. Thera. (1976) 198(1):66-82.
Gould, P.L.: Salt selection for basic drugs; Intl J. of Pharmaceutics (1986) 33: 201-217.
Gross, R.A. et al.: Dynorphin A and cAMP-dependent protein kinase independently regulate neuronal calcium currents; Proc. Natl. Acad. Sci. (1990) 87: 7025-7029.
Hancock, B.C. et al.: Characteristics and Significance of the Amorphous State in Pharmaceutical Systems; J. of Pharm. Sciences (1997) 86(1): 1-12.
Kaiser, C. et al.: Analogs of Phenothiazines. 5. Synthesis and Neuropharmacological Activity of Some Piperidylidene Derivatives of Thioxanthenes, Xanthenes, Dibenzoxepins, and Acridans; J. of Med. Chem. (1974) 17(1): 57-62.
Kenakin, T. et al.: The ligand paradox between affinity and efficacy: can you be there and not make a difference?; Trends in Pharm. Sciences (2002) 23(6): 275-280.
Le Bars, D. et al.: Animal Models of Nociception; Pharmacological Reviews (2001) 53: 597-652.
Lord, John A.H. et al.: Endogenous opioid peptides: multiple agonists and receptors; Nature (1977) 267: 495-499.
Loughhead, D.G.: "Unusual Reductions Induced by Formic Acid[1]"; Tetrahedron Letters, (1988) 29(45): 5701-5702.
Mansour, A. et al.: Anatomy of CNS opioid receptors; Trends in Neuroscience (1988) 11(7): 308-314.
Nieschulz, O. et al.: "Pharmacological studies on 10-(1-methyl-3-piperidyl)-2 methoxyphenothiazine and related compounds"; Arzneimittel-Forschung 1960, 10, 156-165.
Pert, C.B. et al.: Opiate Receptor: Demonstration in Nervous Tissue; Science (1973) 179: 1011-1014.
Sharma, S.K. et al.: Dual regulation of adenylate cyclase accounts for narcotic dependence and tolerance; Proc. Natl. Acad. Sci. (1975) 72(8): 3092-3096.
Still, W. Clark et al.: Rapid Chromatographic Technique for Preparative Separations with Moderate Resolution; J. Org. Chem. (1978) 43(14): 2923-2925.

Sun, X. et al.: Synthesis and Opioid Receptor Binding Properties of Conformation-Rigidified Analogues of 8-Carboxamidocyclazoxcine and 8-Formamidocyclazocine; Abstract of Papers 229th ACS Natl Meeting NY 2005.
Thomas, J.B. et al.: 4-[(8-Alkyl-8-azabicyclo[3.2.1]octyl-3-yl)-3-arylanilino]-*N,N*-diethylbenzamides: High Affinity, Selective Ligands for the Delta Opioid Receptor Illustrate Factors Important to Antagonist Activity; Bioorg. & Med. Chem. Letters (2000) 10(11): 1281-1284.
Thomas, J.B. et al.: (±) -4-[(N-Allyl-*CIS*-3-Methyl-4-Piperidinyl)Phenylamino]-*N,N*-Diethylbenzamide Displays Selective Binding for the Delta Opioid Receptor; Bioorg. & Med. Chem. Letters (1999) 9(20): 3053-3056.
Thomas, J.B. et al.: Factors Influencing Agonist Potency and Selectivity for the Opioid δ Receptor Are Revealed in Structure—Activity Relationship Studies of the 4-[(*N*-Substituted-4-piperidinyl)arylamino]-*N,N*-diethylbenzamides; J. Med. Chem. (2001) 44(6): 972-987.
Truce, W. E. et al.: The Smiles and Related Rearrangements of Aromatic Systems; Organic Reactions (1970) 18: 99-215.
Van Alstine, M.A. et al.: Synthesis and evaluation of novel N-substituted derivatives of 8-carboxamidocyclazocine; Abstract of Papers 231st ACS National Meeting, Atlanta, GA 2006, MEDI-009.
Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954.
Wentland, M.P. et al.: 8-Aminocyclazocine Analogues: Synthesis and Structure—Activity Relationships[†]; Bioorg. & Med. Chem. Letters (2000) 10(2): 183-187.
Wentland, M.P. et al.: Selective Protection and Functionalization of Morphine: Synthesis and Opioid Receptor Binding Properties of 3-Amino-3-desoxymorphine Derivatives[†,1]; J. Med. Chem. (2000) 43(19): 3558-3565.
Wentland, M.P. et al.: 3-Carboxamido Analogues of Morphine and Naltrexone: Synthesis and Opioid Receptor Binding Properties; Bioorg. & Med. Chem. Letters (2001) 11: 1717-1721.
Wentland, M.P. et al.: 8-Carboxamidocyclazocine Analogues: Redefining the Structure—Activity Relationships of 2,6-Methano-3-benzazocines; Bioorg. & Med. Chem. Letters (2001) 11: 623-626.
Wentland, M.P. et al.: Syntheses and Opioid Receptor Binding Affinities of 8-Amino-2,6-methano-3-benzazocines; J. Med. Chem. (2003) 46: 838-849.
Wentland, M.P. et al.: Redefining the Structure—Activity Relationships of 2,6-Methano-3-benzazocines. Part 2: 8-Formamidocyclazocine Analogues; Bioorg. & Med. Chem. Letters (2003) 13: 1911-1914.
Wentland, M.P. et al.: Thioformamido and Thiocarboxamido Derivatives of Cyclazocine: Syntheses and Opioid Receptor Binding Properties; Abstract of Papers 226th ACS Natl. Meeting NY 2003.
Wentland, M.P. et al.: Redefining the structure—activity relationships of 2,6-methano-3-benzazocines. Part 3: 8-Thiocarboxamido and 8-thioformamido derivatives of cyclazocine; Bioorg. & Med. Chem. Letters (2005) 15: 2547-2551.
Wentland, M.P. et al.: Synthesis and opioid receptor binding properties of a highly potent 4-hydroxy analogue of naltrexone; Bioorg. & Med. Chem. Letters (2005) 15: 2107-2110.
Wollemann, M.: Recent Developments in the Research of Opioid Receptor Subtype Molecular Characterization; J. of Neurochemistry (1990) 54(4): 1095-1101.
Zhang, A. et al.: 10-Ketomorphinan and 3-Substituted-3-desoxymorphinan Analogues as Mixed κ and μ Opioid Ligands: Synthesis and Biological Evaluation of Their Binding Affinity at Opioid Receptors; J. Med. Chem. (2004) 47(1):165-174.
Zhang, X. et al.: "Probes for Narcotic Receptor Mediated Phenomena. 26.[1-3] Synthesis and Biological Evaluation of Diarylmethylpiperazines and Diarylmethylpiperidines as Novel, Nonpeptidic δ Opioid Receptor Ligands"; J. Med. Chem. (1999) 42: 5455-5463.
Calderon, S.N. et al.: SNC 80 and Related Opioid Agonists; Current Pharmaceutical Design (2004) 10: 733-742.

* cited by examiner

TRICYCLIC OPIOID MODULATORS

CROSS-REFERENCE TO RELATED APPLICATIONS

This Application claims priority to U.S. Provisional Patent Application No. 60/691,101, filed Jun. 16, 2005, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

C. Kaiser, and others (J. Med. Chem. 1974, Volume 17, pages 57-61) disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or vasoactive agents. These, agents, however, differ significantly from the compounds of the present invention both structurally and pharmacologically.

J. Neumeyer, M. Wentland, and others have disclosed morphine and cyclazocine derivatives wherein their 8-hydroxy group has been replaced by various amino and substituted amino groups (Neumeyer, John L. et al. *J Med. Chem.* 2004, 47 165-174; Wentland, Mark P. et al. *Bioorg. Med. Chem. Lett.* 2003, 13,1911-1914; Wentland, Mark P. et al. *J. Med. Chem.* 2000, 43,3558-3565; and Wentland, Mark P. et al. *J. Med. Chem.* 2003, 46, 838-849).

PCT patent WO 02/36573 discloses 8-substituted-2,6-methano-3-benzazocines that are useful as analgesics, anti-diarrheal agents, anticonvulsants, antitussives, and anti-addiction medications.

U.S. Pat. No. 4,001,419 discloses 1'-substituted xanthene-9-spiro-4'-piperidine derivatives which possess analgesic activity, but does not disclose or suggest compounds of the present invention.

There is a continuing need for new opioid receptor modulators as analgesics. There is a further need for delta and mu opioid receptor agonists as analgesics having reduced side effects. There is a further need for mu opioid receptor agonists as analgesics having reduced side effects for the treatment of pain, immune function, esophageal reflux, and cough. There is also a need for delta opioid receptor agonists as analgesic agents, agents for the treatment of respiratory diseases, cardiovascular agents, agents for treating urological dysfunction, and agents for the treatment of neurological and psychiatric conditions. There is further need for dual delta opioid receptor/mu opioid receptor agonists.

SUMMARY OF THE INVENTION

The present invention is directed to a compound of Formula (I):

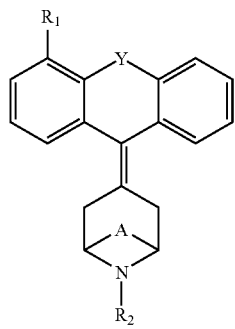

Formula (I)

wherein:
R₁ is hydroxy; mercapto; aminocarbonyl; $C_{1-4}$alkanylaminocarbonyl; di($C_{1-4}$alkanyl)aminocarbonyl; di($C_{1-4}$alkanyl)amino-$C_{1-4}$alkyl-aminocarbonyl; phenyl-aminocarbonyl; phenyl($C_{1-4}$)alkanylaminocarbonyl; $C_{1-4}$alkanyloxycarbonyl; aminothiocarbonyl; amidino; hydroxyamidino; phenylcarbonyl; —C(=NOH)phenyl; amino; $C_{1-4}$alkanylamino; di($C_{1-4}$alkanyl)amino; aminomethyl; hydroxymethyl; $C_{1-4}$alkanylsulfonylamino; $C_{6-10}$arylamino wherein $C_{6-10}$aryl is optionally substituted with one to three substitutents independently selected from the group consisting of $C_{1-6}$alkanyl, $C_{1-6}$alkoxy, halogen, and hydroxy; dihydroimidazolyl; formylamino; thioformylamino; or pyridinylamino; or, optionally, R₁ is —S—C(NH₂)=N— to form a fused moiety in which the second point of attachment is an adjacent non-bridging carbon atom;

R₂ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$) alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, benzothiophenyl, tetrazolyl, and thiazolyl; wherein phenyl, naphthyl and heteroaryl are optionally substituted with phenyl, and one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH₂)₃₋₅—, —O(CH₂)₂₋₄—, —(CH₂)₂₋₄O—, and —O(CH₂)₁₋₃O—;

A is absent or —(CH₂)₂₋₃—;

Y is O or S;

and enantiomers, diastereomers, tautomers, solvates, or pharmaceutically acceptable salts thereof.

Finally, the present invention is directed to veterinary and pharmaceutical compositions containing compounds of Formula (I) wherein the compositions are used to treat mild to severe pain in warm-blooded animals

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or (C$_1$-C$_6$) alkyl.

"Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is (C$_{6-26}$) arylalkyl, e.g., the alkanyl, alkenyl or alkynyl moiety of the arylalkyl group is (C$_{1-6}$) and the aryl moiety is (C$_{5-20}$). In particularly preferred embodiments the arylalkyl group is (C$_{6-13}$), e.g., the alkanyl, alkenyl or alkynyl moiety of the arylalkyl group is (C$_{1-3}$) and the aryl moiety is (C$_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy (CH$_3$CH$_2$CH$_2$O—), propan-2-yloxy ((CH$_3$)$_2$CHO—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are (C$_{1-8}$) alkanyloxy groups, with (C$_{1-3}$) being particularly preferred.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —O(O)SR, —C(S)SR, —O(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, (C$_{1-8}$alkylamino)carbonyl, (arylamino)carbonyl and aryl(C$_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkanyl" substituent refers to a group of the formula

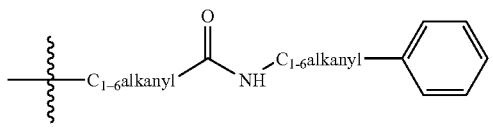

An embodiment of the present invention is directed to a compound of Formula (I) wherein the structure is numbered as defined herein.

Formula (I)

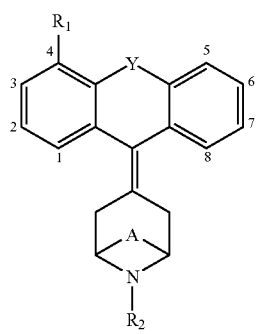

The present invention is directed to analgesic uses of compositions comprising a compound of Formula (I):

Formula (I)

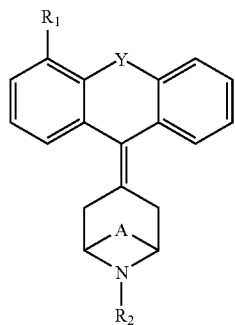

wherein:

R$_1$ is hydroxy; mercapto; aminocarbonyl; C$_{1-4}$alkanylaminocarbonyl; di(C$_{1-4}$alkanyl)aminocarbonyl; (phenylmethyl)aminocarbonyl; (4-methoxy-phenylmethyl)aminocarbonyl; C$_{1-4}$alkanyloxycarbonyl; aminothiocarbonyl; amidino; hydroxyamidino; phenylcarbonyl; —C(=NOH)phenyl; amino; C$_{1-4}$alkanylamino; di(C$_{1-4}$alkanyl)amino; aminomethyl; hydroxymethyl; methanesulfonylamino; C$_{6-10}$arylamino wherein C$_{6-10}$aryl is optionally substituted with one to three substitutents independently selected from the group consisting of C$_{1-6}$alkanyl, C$_{1-6}$alkoxy, halogen, and hydroxy; dihydroimidazolyl; formylamino; thioformylamino; or pyridinylamino; or, optionally, R$_1$ is —S—C(NH$_2$)=N— to form a fused moiety in which the second point of attachment is an adjacent non-bridging carbon atom;

R$_2$ is a substituent selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, C$_{1-8}$alkanyloxycarbonyl, halo$_{1-3}$(C$_{1-8}$)alkanylcarbonyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl(C$_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with phenyl, and one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl, thioureido, and fluoro(C$_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

A is absent or —(CH$_2$)$_{2-3}$—;

Y is O or S;

and enantiomers, diastereomers, tautomers, solvates, or pharmaceutically acceptable salts thereof.

In another embodiment, the present invention is directed to anti-pyretic uses of compositions comprising a compound of Formula (I):

Formula (I)

wherein:

R$_1$ is hydroxy; mercapto; aminocarbonyl; C$_{1-4}$alkanylaminocarbonyl; di(C$_{1-4}$alkanyl)aminocarbonyl; (phenylmethyl)aminocarbonyl; (4-methoxy-phenylmethyl)aminocarbonyl; C$_{1-4}$alkanyloxycarbonyl; aminothiocarbonyl; amidino; hydroxyamidino; phenylcarbonyl; —C(=NOH)phenyl; amino; C$_{1-4}$alkanylamino; di(C$_{1-4}$alkanyl)amino; aminomethyl; hydroxymethyl; methanesulfonylamino; C$_{6-10}$arylamino wherein C$_{6-10}$aryl is optionally substituted with one to three substitutents independently selected from the group consisting of C$_{1-6}$alkanyl, C$_{1-6}$alkoxy, halogen, and hydroxy; dihydroimidazolyl; formylamino; thioformylamino; or pyridinylamino; or, optionally, $R_1$ is —S—C($NH_2$)=N— to form a fused moiety in which the second point of attachment is an adjacent non-bridging carbon atom;

$R_2$ is a substituent selected from the group consisting of hydrogen, $C_{1-8}$alkanyl, $halo_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, $halo_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with phenyl, and one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —($CH_2$)$_{3-5}$—, —O($CH_2$)$_{2-4}$—, —($CH_2$)$_{2-4}$O—, and —O($CH_2$)$_{1-3}$O—;

A is absent or —($CH_2$)$_{2-3}$—;

Y is O or S;

and enantiomers, diastereomers, tautomers, solvates, or pharmaceutically acceptable salts thereof.

Embodiments of the present invention include compounds of Formula (I) wherein:

a) $R_1$ is hydroxy, aminocarbonyl, aminothiocarbonyl; hydroxyamidino, or formylamino;

b) $R_1$ is hydroxy or aminocarbonyl;

c) $R_1$ is hydroxy;

d) $R_2$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form —O($CH_2$)$_{1-3}$O—;

e) $R_2$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with a hydroxyl group;

f) $R_2$ is hydrogen, methyl, allyl, or heteroarylmethyl wherein heteroaryl is selected from the group consisting of benzo[1,3]dioxolyl, imidazolyl, furanyl, pyridinyl, and thienyl;

g) $R_2$ is hydrogen;

h) A is absent or —($CH_2$)$_2$—;

i) A is —($CH_2$)$_2$—;

j) Y is O;

and combinations of a) through j) above.

One embodiment of the present invention is a compound of Formula (I) wherein:

$R_1$ is hydroxy, aminocarbonyl, aminothiocarbonyl; hydroxyamidino, or formylamino;

$R_2$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form —O($CH_2$)$_{1-3}$O—;

A is absent or —($CH_2$)$_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy or aminocarbonyl;

$R_2$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with a hydroxyl group;

A is —($CH_2$)$_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy;

$R_2$ is hydrogen, methyl, allyl, or heteroarylmethyl wherein heteroaryl is selected from the group consisting of benzo[1,3]dioxolyl, imidazolyl, furanyl, pyridinyl, and thienyl;

A is —($CH_2$)$_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy;

$R_2$ is hydrogen;

A is —(CH$_2$)$_2$—;
Y is O;
and enantiomers, diastereomers, tautomers, solvates, or pharmaceutically acceptable salts thereof.

The present invention is also directed to analgesic uses of compositions comprising a compound of Formula (I):

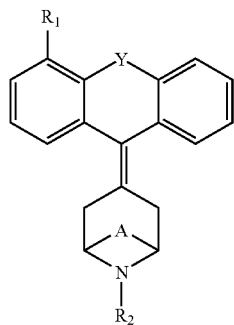

Formula (I)

wherein:
R$_1$ is hydroxy; mercapto; aminocarbonyl; C$_{1-4}$alkanylaminocarbonyl; di(C$_{1-4}$alkanyl)aminocarbonyl; di(C$_{1-4}$alkanyl)amino-C$_{1-4}$alkyl-aminocarbonyl; phenyl-aminocarbonyl; phenyl(C$_{1-4}$)alkanylaminocarbonyl; C$_{1-4}$alkanyloxycarbonyl; aminothiocarbonyl; amidino; hydroxyamidino; phenylcarbonyl; —C(=NOH)phenyl; amino; C$_{1-4}$alkanylamino; di(C$_{1-4}$alkanyl)amino; aminomethyl; hydroxymethyl; C$_{1-4}$alkanylsulfonylamino; C$_{6-10}$arylamino wherein C$_{6-10}$aryl is optionally substituted with one to three substitutents independently selected from the group consisting of C$_{1-6}$alkanyl, C$_{1-6}$alkoxy, halogen, and hydroxy; dihydroimidazolyl; formylamino; thioformylamino; or pyridinylamino; or, optionally, R$_1$ is —S—C(NH$_2$)=N— to form a fused moiety in which the second point of attachment is an adjacent non-bridging carbon atom;

R$_2$ is a substituent selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, C$_{1-8}$alkanyloxycarbonyl, halo$_{1-3}$(C$_{1-8}$)alkanylcarbonyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl(C$_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, benzothiophenyl, tetrazolyl, and thiazolyl; wherein phenyl, naphthyl and heteroaryl are optionally substituted with phenyl, and one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl, thioureido, and fluoro(C$_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

A is absent or —(CH$_2$)$_{2-3}$—;
Y is O or S;
and enantiomers, diastereomers, tautomers, solvates, or pharmaceutically acceptable salts thereof.

In another embodiment, the present invention is directed to anti-pyretic uses of compositions comprising a compound of Formula (I):

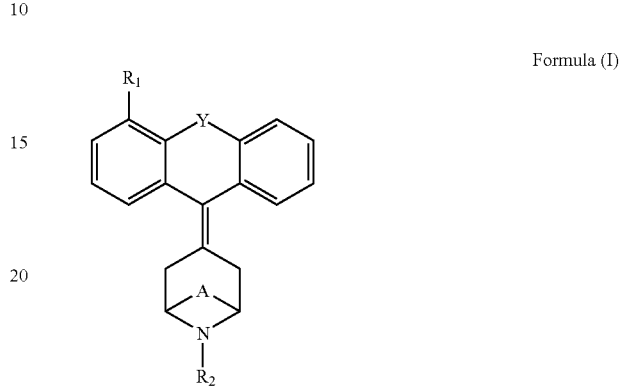

Formula (I)

wherein:
R$_1$ is hydroxy; mercapto; aminocarbonyl; C$_{1-4}$alkanylaminocarbonyl; di(C$_{1-4}$alkanyl)aminocarbonyl; di(C$_{1-4}$alkanyl)amino-C$_{1-4}$alkyl-aminocarbonyl; phenyl-aminocarbonyl; phenyl(C$_{1-4}$)alkanylaminocarbonyl; C$_{1-4}$alkanyloxycarbonyl; aminothiocarbonyl; amidino; hydroxyamidino; phenylcarbonyl; —C(=NOH)phenyl; amino; C$_{1-4}$alkanylamino; di(C$_{1-4}$alkanyl)amino; aminomethyl; hydroxymethyl; C$_{1-4}$alkanylsulfonylamino; C$_{6-10}$arylamino wherein C$_{6-10}$aryl is optionally substituted with one to three substitutents independently selected from the group consisting of C$_{1-6}$alkanyl, C$_{1-6}$alkoxy, halogen, and hydroxy; dihydroimidazolyl; formylamino; thioformylamino; or pyridinylamino; or, optionally, R$_1$ is —S—C(NH$_2$)=N— to form a fused moiety in which the second point of attachment is an adjacent non-bridging carbon atom;

R$_2$ is a substituent selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, C$_{1-8}$alkanyloxycarbonyl, halo$_{1-3}$(C$_{1-8}$)alkanylcarbonyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl(C$_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, benzothiophenyl, tetrazolyl, and thiazolyl; wherein phenyl, naphthyl and heteroaryl are optionally substituted with phenyl, and one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoro(C$_{1-6}$)alkanyl, thioureido, and fluoro(C$_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —$(CH_2)_{3-5}$—, —$O(CH_2)_{2-4}$—, —$(CH_2)_{2-4}O$—, and —$O(CH_2)_{1-3}O$—;

A is absent or —$(CH_2)_{2-3}$—;

Y is O or S;

and enantiomers, diastereomers, tautomers, solvates, or pharmaceutically acceptable salts thereof.

Embodiments of the present invention include compounds of Formula (I) wherein:

a) $R_1$ is hydroxy, aminocarbonyl, hydroxyamidino, formylamino; $C_{1-4}$alkanylaminocarbonyl; phenyl-aminocarbonyl; phenyl($C_{1-4}$)alkanylaminocarbonyl; $C_{6-10}$arylamino wherein $C_{6-10}$aryl is optionally substituted with one to two substitutents independently selected from the group consisting of $C_{1-4}$alkanyl, $C_{1-4}$alkoxy, halogen, and hydroxy; or pyridinylamino;

b) $R_1$ is hydroxy, aminocarbonyl, hydroxyamidino, formylamino; $C_{1-4}$alkanylaminocarbonyl; phenyl-aminocarbonyl; phenyl($C_{1-4}$)alkanylaminocarbonyl; or pyridinylamino;

c) $R_1$ is hydroxy, aminocarbonyl, formylamino; phenyl-aminocarbonyl; or phenyl($C_{1-4}$)alkanylaminocarbonyl;

d) $R_1$ is hydroxy, aminocarbonyl, formylamino; phenyl-aminocarbonyl; or phenylmethylaminocarbonyl;

e) $R_2$ is selected from the group consisting of hydrogen, $C_{1-8}$alkanyl, $C_{2-8}$alkenyl, $C_{2-8}$alkynyl, $C_{3-8}$-cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, benzothiophenyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form —$O(CH_2)_{1-3}O$—;

f) $R_2$ is selected from the group consisting of hydrogen, methyl, allyl, 2-methyl-allyl, 3-methyl-but-2-enyl, propynyl, hydroxyethyl, $C_{3-5}$cycloalkanylmethyl, methylthioethyl, methoxyethyl, thioformyl, phenyliminomethyl, phenethyl, and heteroaryl($C_{1-2}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, benzothiophenyl, tetrazolyl; wherein the phenyl in any phenyl-containing substituent and the pyridinyl substituent are optionally substituted with one hydroxyl group;

g) $R_2$ is hydrogen, methyl, allyl, 3-methyl-but-2-enyl, cyclopropylmethyl, phenylmethyl, or heteroarylmethyl wherein heteroaryl is selected from the group consisting of benzo[1,3]dioxolyl, imidazolyl, furanyl, pyridinyl, and thienyl;

h) $R_2$ is hydrogen, methyl, 3-methyl-but-2-enyl, cyclopropylmethyl, phenylmethyl, pyridin-2-ylmethyl, pyridin-3-ylmethyl, pyridin-4-ylmethyl, 2-hydroxy-pyridin-4-ylmethyl, imidazol-2-ylmethyl, thien-2-ylmethyl, or furan-3-ylmethyl;

i) A is absent or —$(CH_2)_2$—;

j) A is —$(CH_2)_2$—;

k) Y is O;

and combinations of a) through k) above.

One embodiment of the present invention is a compound of Formula (I) wherein:

$R_1$ is hydroxy, aminocarbonyl, hydroxyamidino, formylamino; $C_{1-4}$alkanylaminocarbonyl; phenyl-aminocarbonyl; phenyl($C_{1-4}$)alkanylaminocarbonyl; $C_{6-10}$arylamino wherein $C_{6-10}$aryl is optionally substituted with one to two substitutents independently selected from the group consisting of $C_{1-4}$alkanyl, $C_{1-4}$alkoxy, halogen, and hydroxy; or pyridinylamino;

$R_2$ is selected from the group consisting of hydrogen, $C_{1-8}$alkanyl, $C_{2-8}$alkenyl, $C_{2-8}$alkynyl, $C_{3-8}$cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, benzothiophenyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form —$O(CH_2)_{1-3}O$—;

A is absent or —$(CH_2)_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy, aminocarbonyl, formylamino; phenyl-aminocarbonyl; or pyridinylamino;

$R_2$ is selected from the group consisting of hydrogen, methyl, allyl, 2-methyl-allyl, 3-methyl-but-2-enyl, propynyl, hydroxyethyl, $C_{3-5}$cycloalkanylmethyl, methylthioethyl, methoxyethyl, thioformyl, phenyliminomethyl, phenethyl, and heteroaryl($C_{1-2}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, benzothiophenyl, tetrazolyl; wherein the phenyl in any phenyl-containing substituent and the pyridinyl substituent are optionally substituted with one hydroxyl group;

A is —$(CH_2)_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy, aminocarbonyl, formylamino; phenyl-aminocarbonyl; or phenyl($C_{1-4}$)alkanylaminocarbonyl;

$R_2$ is hydrogen, methyl, allyl, 3-methyl-but-2-enyl, cyclopropylmethyl, phenylmethyl, or heteroarylmethyl wherein heteroaryl is selected from the group consisting of benzo[1,3]dioxolyl, imidazolyl, furanyl, pyridinyl, and thienyl;

A is —$(CH_2)_2$—;

Y is O;

and enantiomers, diastereomers, tautomers, solvates, or pharmaceutically acceptable salts thereof.

Another embodiment of the present invention is a compound of Formula (I) wherein:

$R_1$ is hydroxy, aminocarbonyl, formylamino; phenyl-aminocarbonyl; or phenylmethylaminocarbonyl;
$R_2$ is hydrogen, methyl, 3-methyl-but-2-enyl, cyclopropylmethyl, phenylmethyl, pyridin-2-ylmethyl, pyridin-3-ylmethyl, pyridin-4-ylmethyl, 2-hydroxy-pyridin-4-ylmethyl, imidazol-2-ylmethyl, thien-2-ylmethyl, or furan-3-ylmethyl;
A is —$(CH_2)_2$—;
Y is O;
and enantiomers, diastereomers, tautomers, solvates, or pharmaceutically acceptable salts thereof.

Another embodiment of the present invention is directed to compositions comprising a compound of Formula (Ia)

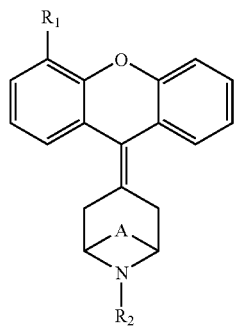

Formula (Ia)

selected from the group consisting of
a compound of Formula (Ia) wherein $R_1$ is methoxy, A is —$(CH_2)_2$—, and $R_2$ is H;
a compound of Formula (Ia) wherein $R_1$ is hydroxy, A is —$(CH_2)_2$—, and $R_2$ is H;
a compound of Formula (Ia) wherein $R_1$ is aminocarbonyl, A is —$(CH_2)_2$—, and $R_2$ is H;
a compound of Formula (Ia) wherein $R_1$ is aminocarbonyl, A is —$(CH_2)_2$—, and $R_2$ is furan-2-ylmethyl;
Enant. A, a compound of Formula (Ia) wherein $R_1$ is hydroxy, A is —$(CH_2)_2$—, and $R_2$ is trifluoromethylcarbonyl;
Enant. B, a compound of Formula (Ia) wherein $R_1$ is hydroxy, A is —$(CH_2)_2$—, and $R_2$ is trifluoromethylcarbonyl;
a compound of Formula (Ia) wherein $R_1$ is methoxycarbonyl, A is —$(CH_2)_2$—, and $R_2$ is trifluoromethylcarbonyl;
a compound of Formula (Ia) wherein $R_1$ is hydroxy, A is —$(CH_2)_2$—, and $R_2$ is H;
a compound of Formula (Ia) wherein $R_1$ is hydroxy, A is —$(CH_2)_2$—, and $R_2$ is H;
a compound of Formula (Ia) wherein $R_1$ is methylaminocarbonyl, A is —$(CH_2)_2$—, and $R_2$ is H;
a compound of Formula (Ia) wherein $R_1$ is dimethylaminocarbonyl, A is —$(CH_2)_2$—, and $R_2$ is H;
a compound of Formula (Ia) wherein $R_1$ is phenyl-aminocarbonyl, A is —$(CH_2)_2$—, and $R_2$ is H;
a compound of Formula (Ia) wherein $R_1$ is phenylmethylaminocarbonyl, A is —$(CH_2)_2$—, and $R_2$ is H;
a compound of Formula (Ia) wherein $R_1$ is phenylethyl-aminocarbonyl, A is —$(CH_2)_2$—, and $R_2$ is H;
a compound of Formula (Ia) wherein $R_1$ is (2-dimethylamino-ethyl)aminocarbonyl, A is —$(CH_2)_2$—, and $R_2$ is H;
a compound of Formula (Ia) wherein $R_1$ is hydroxy, A is absent, and $R_2$ is H;
a compound of Formula (Ia) wherein $R_1$ is hydroxy, A is —$(CH_2)_3$—, and $R_2$ is methyl;
a compound of Formula (Ia) wherein $R_1$ is hydroxy, A is absent, and $R_2$ is methyl;
a compound of Formula (Ia) wherein $R_1$ is hydroxy, A is —$(CH_2)_2$—, and $R_2$ is methyl;
a compound of Formula (Ia) wherein $R_1$ is hydroxy, A is —$(CH_2)_3$—, and $R_2$ is H;
a compound of Formula (Ia) wherein $R_1$ is hydroxy, A is —$(CH_2)_2$—, and $R_2$ is pyridin-2-ylmethyl;
a compound of Formula (Ia) wherein $R_1$ is hydroxy, A is —$(CH_2)_2$—, and $R_2$ is pyridin-4-ylmethyl;
a compound of Formula (Ia) wherein $R_1$ is hydroxy, A is —$(CH_2)_2$—, and $R_2$ is 2-hydroxy-pyridin-4-ylmethyl;
a compound of Formula (Ia) wherein $R_1$ is hydroxy, A is —$(CH_2)_2$—, and $R_2$ is thien-2-ylmethyl;
a compound of Formula (Ia) wherein $R_1$ is hydroxy, A is —$(CH_2)_2$—, and $R_2$ is furan-3-ylmethyl;
a compound of Formula (Ia) wherein $R_1$ is hydroxy, A is —$(CH_2)_2$—, and $R_2$ is cyclopropylmethyl;
a compound of Formula (Ia) wherein $R_1$ is hydroxy, A is —$(CH_2)_2$—, and $R_2$ is 2-methyl-but-2-enyl;
a compound of Formula (Ia) wherein $R_1$ is hydroxy, A is —$(CH_2)_2$—, and $R_2$ is 2-phenyl-imidazol-4-ylmethyl;
a compound of Formula (Ia) wherein $R_1$ is aminocarbonyl, A is —$(CH_2)_2$—, and $R_2$ is trifluoromethylcarbonyl
a compound of Formula (Ia) wherein $R_1$ is hydroxy, A is —$(CH_2)_2$—, and $R_2$ is phenethyl;
a compound of Formula (Ia) wherein $R_1$ is hydroxy, A is —$(CH_2)_2$—, and $R_2$ is pyridin-2-ylmethyl;
a compound of Formula (Ia) wherein $R_1$ is hydroxy, A is —$(CH_2)_2$—, and $R_2$ is phenylmethyl;
a compound of Formula (Ia) wherein $R_1$ is hydroxy, A is —$(CH_2)_2$—, and $R_2$ is benzothien-3-ylmethyl;
a compound of Formula (Ia) wherein $R_1$ is hydroxy, A is —$(CH2)_2$—, and $R_2$ is 1H-imidazol-2-ylmethyl;
a compound of Formula (Ia) wherein $R_1$ is hydroxy, A is —$(CH_2)_2$—, and $R_2$ is isoquinolin-5-ylmethyl;
Enant. A, a compound of Formula (Ia) wherein $R_1$ is aminocarbonyl, A is —$(CH_2)_2$—, and $R_2$ is trifluoromethylcarbonyl;
Enant. A, a compound of Formula (Ia) wherein $R_1$ is aminocarbonyl, A is —$(CH_2)_2$—, and $R_2$ is H;
Enant. B, a compound of Formula (Ia) wherein $R_1$ is aminocarbonyl, A is —$(CH_2)_2$—, and $R_2$ is trifluoromethylcarbonyl;
Enant. A, a compound of Formula (Ia) wherein $R_1$ is aminocarbonyl, A is —$(CH_2)_2$—, and $R_2$ is H;
a compound of Formula (Ia) wherein $R_1$ is amino, A is —$(CH_2)_2$—, and $R_2$ is H;
a compound of Formula (Ia) wherein $R_1$ is hydroxyamidino, A is —$(CH_2)_2$—, and $R_2$ is H;
a compound of Formula (Ia) wherein $R_1$ is hydroxyamidino, A is —$(CH_2)_2$—, and $R_2$ is H;
a compound of Formula (Ia) wherein $R_1$ is formylamino, A is —$(CH_2)_2$—, and $R_2$ is H;
Enant. A, a compound of Formula (Ia) wherein $R_1$ is hydroxy, A is —$(CH_2)_2$—, and $R_2$ is phenylmethyl;
Enant. B, a compound of Formula (Ia) wherein $R_1$ is hydroxy, A is —$(CH_2)_2$—, and $R_2$ is phenylmethyl;
a compound of Formula (Ia) wherein $R_1$ is phenylaminocarbonyl, A is —$(CH_2)_2$—, and $R_2$ is H;
a compound of Formula (Ia) wherein $R_1$ is phenylaminocarbonyl, A is —$(CH_2)_2$—, and $R_2$ is H;
Enant, A, a compound of Formula (Ia) wherein $R_1$ is hydroxy, A is —$(CH_2)_2$—, and $R_2$ is pyridin-3ylmethyl;
Enant. B, a compound of Formula (Ia) wherein $R_1$ is hydroxy, A is —$(CH_2)_2$—, and $R_2$ is pyridin-3-ylmethyl;

Enant. A, a compound of Formula (Ia) wherein $R_1$ is hydroxy, A is —$(CH_2)_2$—, and $R_2$ is methyl;
Enant. B, a compound of Formula (Ia) wherein $R_1$ is hydroxy, A is —$(CH_2)_2$—, and $R_2$ is methyl;
Enant. A, a compound of Formula (Ia) wherein $R_1$ is phenylmethylaminocarbonyl, A is —$(CH_2)_2$—, and $R_2$ is H;
Enant. B, a compound of Formula (Ia) wherein $R_1$ is phenylmethylaminocarbonyl, A is —$(CH_2)_2$—, and $R_2$ is H;
Enant. A, a compound of Formula (Ia) wherein $R_1$ is phenethylaminocarbonyl, A is —$(CH_2)_2$—, and $R_2$ is H;
Enant. B, a compound of Formula (Ia) wherein $R_1$ is phenethylaminocarbonyl, A is —$(CH_2)_2$—, and $R_2$ is H;
Enant. B, a compound of Formula (Ia) wherein $R_1$ is hydroxy, A is —$(CH_2)_2$—, and $R_2$ is furan-3-ylmethyl;
Enant. A, a compound of Formula (Ia) wherein $R_1$ is hydroxy, A is —$(CH_2)_2$—, and $R_2$ is furan-3-ylmethyl;
Enant. A, a compound of Formula (Ia) wherein $R_1$ is hydroxy, A is —$(CH_2)_2$—, and $R_2$ is pyridin-2-ylmethyl;
Enant. B, a compound of Formula (Ia) wherein $R_1$ is hydroxy, A is —$(CH_2)_2$—, and $R_2$ is pyridin-2-ylmethyl;
a compound of Formula (Ia) wherein $R_1$ is 4-chloro-phenylamino, A is —$(CH_2)_2$—, and $R_2$ is H;
a compound of Formula (Ia) wherein $R_1$ is pyridin-3-ylamino, A is —$(CH_2)_2$—, and $R_2$ is H; and
a compound of Formula (Ia) wherein $R_1$ is phenylamino, A is —$(CH_2)_2$—, and $R_2$ is H.

Another embodiment of the present invention is directed to compositions comprising a compound of Formula (Ib)

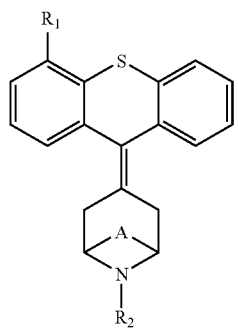

Formula (Ib)

selected from the group consisting of
a compound of Formula (Ib) wherein $R_1$ is aminocarbonyl, A is —$(CH_2)_2$—, and $R_2$ is H; and
a compound of Formula (Ib) wherein $R_1$ is aminocarbonyl, A is —$(CH_2)_2$—, and $R_2$ is trifluoromethylcarbonyl.

Another embodiment of the present invention is a composition comprising the dextrorotatory enantiomer of a compound of formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

The compounds of the present invention may also be present in the form of pharmaceutically acceptable salts. For use in medicine, the salts of the compounds of this invention refer to non-toxic "pharmaceutically acceptable salts" (Ref International J. Pharm., 1986, 33, 201-217; J. Pharm.Sci., 1997 (Jan), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Representative hydroxy group prodrug forms include, but are not limited to, $C_{1-4}$alkanylethers, substituted $C_{1-4}$alkanylethers, and $C_{1-4}$alkanyl esters.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography, The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose.

The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the disases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

The preparation of compounds of this invention wherein $R_1$ is OH is illustrated in Scheme 1. Compounds in which $R_1$ is SH may be prepared in an analogous manner, starting with a thioether, such as a methylthioether, wherein R is methyl. In stages 1.1 and 1.2, intermediates 1C and 2 consist of two functionalized benzene rings connected by a linker —Y—, wherein Y is defined as oxygen or sulfur. One benzene ring must bear a carboxylic acid, or a precursor to a carboxylic acid, positioned ortho to the linker —Y—.

In Scheme 1 Stage 1.1, the —Y— bridge may be constructed from compounds 1A and 1B by a nucleophilic aromatic displacement of an appropriate leaving group X, wherein X is fluoro, chloro, bromo, iodo, or the like. The compounds of formula 2 are then obtained by hydrolysis of the $R_{11}$ ester (wherein $R_{11}$, is a $C_{1-4}$alkanyl) of compounds of formula 1C with an alkali metal hydroxide (Stage 1.2).

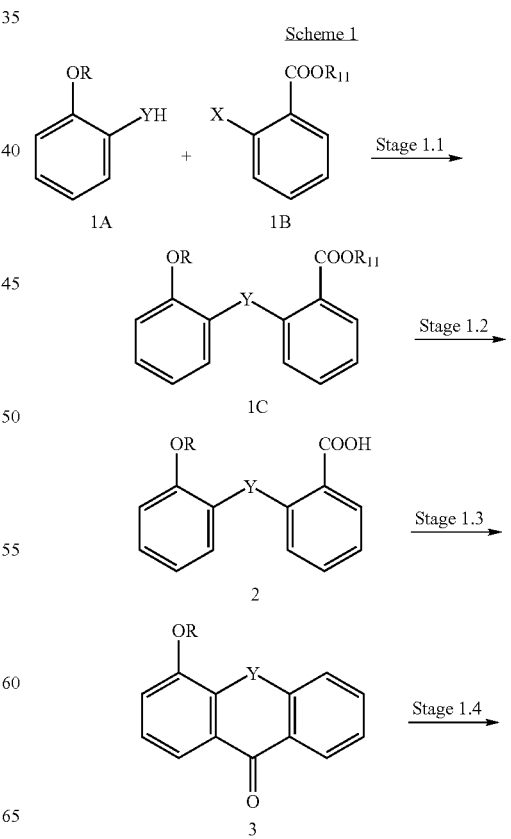

Scheme 1

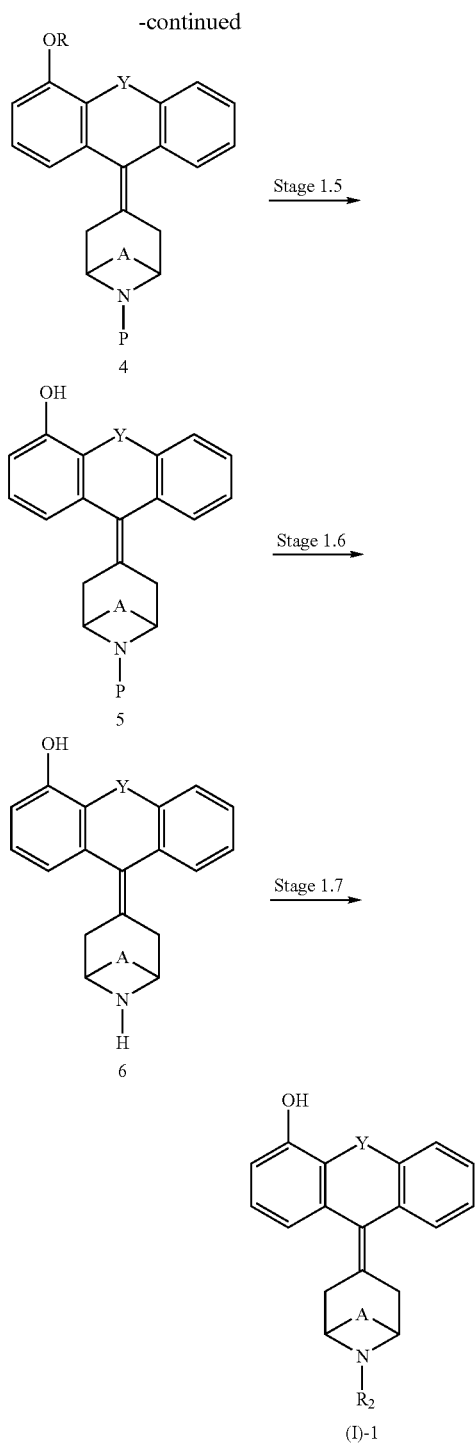

R = C$_{1-4}$alkanyl or benzyl
R$_{11}$ = C$_{1-4}$alkanyl

In Stage 1.3 compounds of formula 2 are converted by cycloacylation to ketones of formula 3, using, for instance, BF$_3$.Et$_2$O-trifluoroacetic anhydride or polyphosphoric acid. Alternatively, the cyclization may be effected by converting the acid functionality of compounds of formula 2 to an acid chloride, for instance with thionyl chloride or oxalyl chloride, followed by Friedel-Crafts ring closure in the presence of a Lewis acid, such as aluminum chloride.

To perform Stage 1.4, the ketone is replaced by an appropriately substituted alkenyl functionality to give compounds of formula 4. This transformation may be carried out by a McMurray condensation of the ketones of formula 3 with a second appropriate ketone in the presence of a lower valent titanium reagent such as the reagent obtained from addition of titanium tetrachloride to zinc dust. Alternatively, an appropriately substituted magnesium halide may be added to ketones of formula 3 to afford carbinols. Dehydration of such carbinols with acidic reagents such as formic acid, sulfuric acid or trifluoroacetic acid gives rise to compounds of formula 4.

Stage 1.5 includes the removal of R (wherein R is C$_{1-4}$alkanyl or benzyl) from compounds of formula 4 using conventional deprotection methods. Such transformations may include the dealkylation of lower alkyl ethers to give their corresponding alcohols, using reagents such as boron trihalides or removal of the benzyl group via hydrogenation using hydrogen gas and a transition metal catalyst such as palladium. In the case of methylthioethers, demethylation of the methyl thiol may be accomplished via treatment with meta-chloroperbenzoic acid, followed by heating in trifluoroacetic anhydride.

As illustrated in Scheme 1, the nitrogen atoms of compounds of formula 4 and 5 may bear a group P. This group may be an alkanyl, alkenyl or aralkanyl in which case they are therapeutically useful products of this invention. The group P may also be trifluoromethylcarbonyl, alkoxycarbonyl or aralkoxycarbonyl. The group P can be removed to produce free amine 6 (Stage 1.6). This transformation may be carried out using certain acidic reagents such as trifluoroacetic acid, hydrogen bromide, or trimethylsilyl iodide. Or, when P is a trifluoromethylcarbonyl, basic reagents such as potassium carbonate in an alcoholic solvent may be used for the removal of P. Compounds of formula 4 and 5 bearing readily cleavable groups such as methyl, allyl or benzyl may be transformed into the aforementioned alkoxycarbonyl derivatives by treatment with alkanylchloroformates such as ethyl chloroformate or 1-chloroethyl chloroformate.

Finally, the secondary amines of formula 6 may be converted to compounds of formula (I)-1 as shown in Stage 1.7. These transformations may be carried out by reductive alkylation with a carbonyl compound in the presence of a reducing agent such as sodium borohydride, sodium cyanoborohydride, sodium triacetoxyborohydride, or tetramethylammonium triacetoxyborohydride. Alternatively, the amines of formula 6 may be treated with an appropriate alkylating agent, such as a halide- or tosylate-substituted alkanyl, alkenyl or aralkyl group and an organic or inorganic base.

Finally, the transformation of compounds of formula 4 into compounds of formula (I)-1 may also be accomplished by reversing the order of Stages 1.5 and Stage 1.6. In this case, group P is removed prior to removal of R by the methods described above.

Scheme 2 demonstrates the preparation of compounds of the present invention wherein R$_1$ is other than hydroxy or mercapto. A compound of formula 5 can be converted to its triflate by treatment with N,N-bis(trifluoromethylsulfonyl)phenylamine or similar reagents to afford a compound of formula 2A. Treatment of the triflate with a cyanide source such as zinc cyanide in the presence of a palladium catalyst provides compounds of formula 2B, which subsequently can be hydrolyzed with hydroxide anion in the presence of hydrogen peroxide to afford compounds of formula (I)-2 wherein R$_1$ is an aminocarbonyl.

Scheme 2

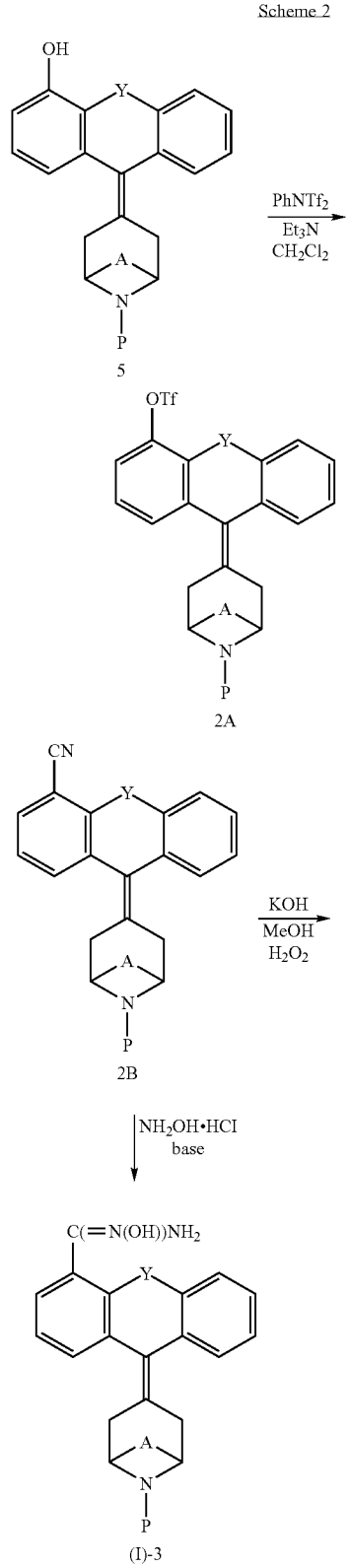

ammonium hydroxide in the presence of a base such as a tertiary amine to afford a hydroxyamidino compound of formula (I)-3.

Similarly, a compound of formula 5 may be treated with amino synthon, wherein a synthon is a synthetic equivalent or a functional group that is related to some other structural unit by a reliable reaction or sequence of reactions. An example of an amino group synthon includes, but is not limited to, benzophenone imine. Benzophenone imine may be used in the presence of an appropriate palladium catalyst under basic conditions, which upon treatment with ammonium hydroxide, affords compounds of formula 3A. The aniline may be formylated with acetic formic anhydride to give compounds of formula (I)-4, followed by removal of P using methods discussed herein. Lawesson's reagent may be used to convert carbonyl-containing $R_1$ substituents to their corresponding thiocarbonyl analogs.

Scheme 3

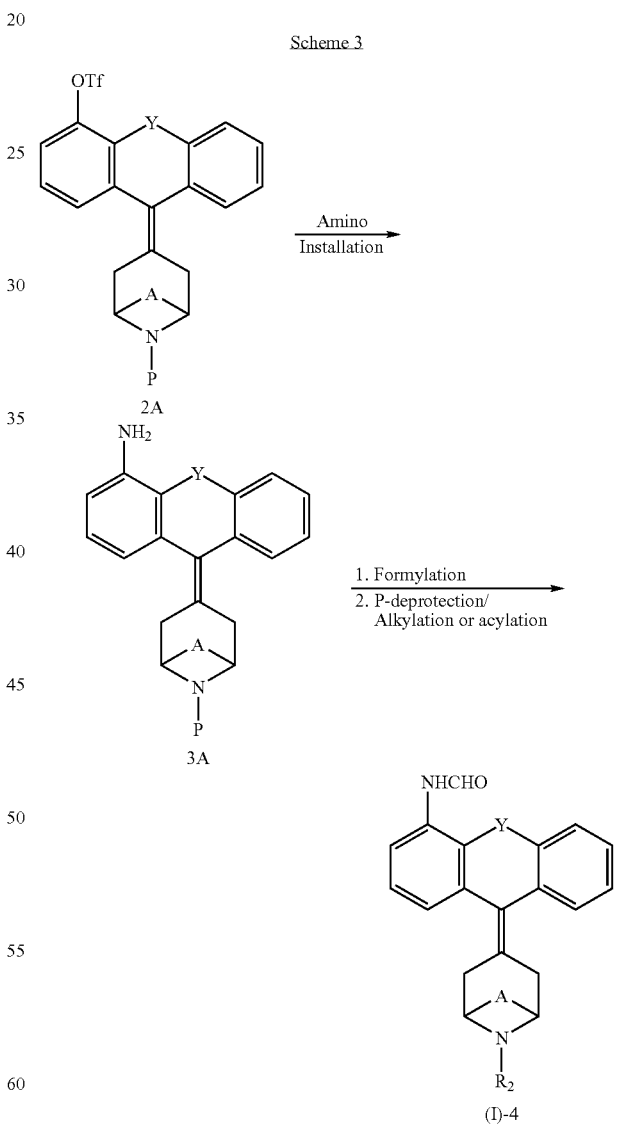

The cyano group of a compound of formula 2B is also a precursor to other $R_1$ substituents of the present invention. For example, a compound of formula 2B can be treated with The preparation of compounds wherein $R_1$ is $C_{6-10}$arylamino can be achieved using a palladium catalyzed amination of a compound of formula 2A with $C_{6-10}$arylamine and an inorganic base, such as cesium carbonate.

Anilines of formula 3A may be converted to the corresponding aminothiazoles of formula (I)-5 via reaction with appropriate reagents such as potassium thiocyanate.

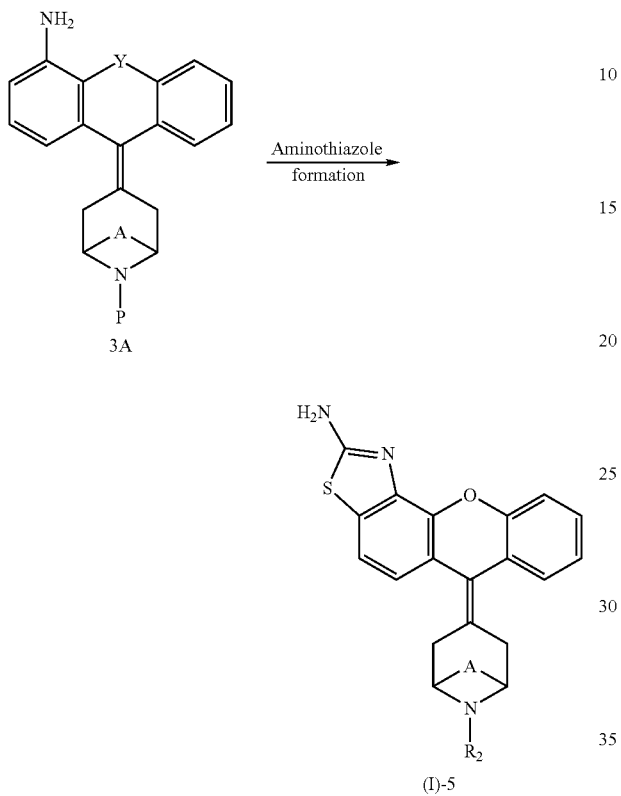

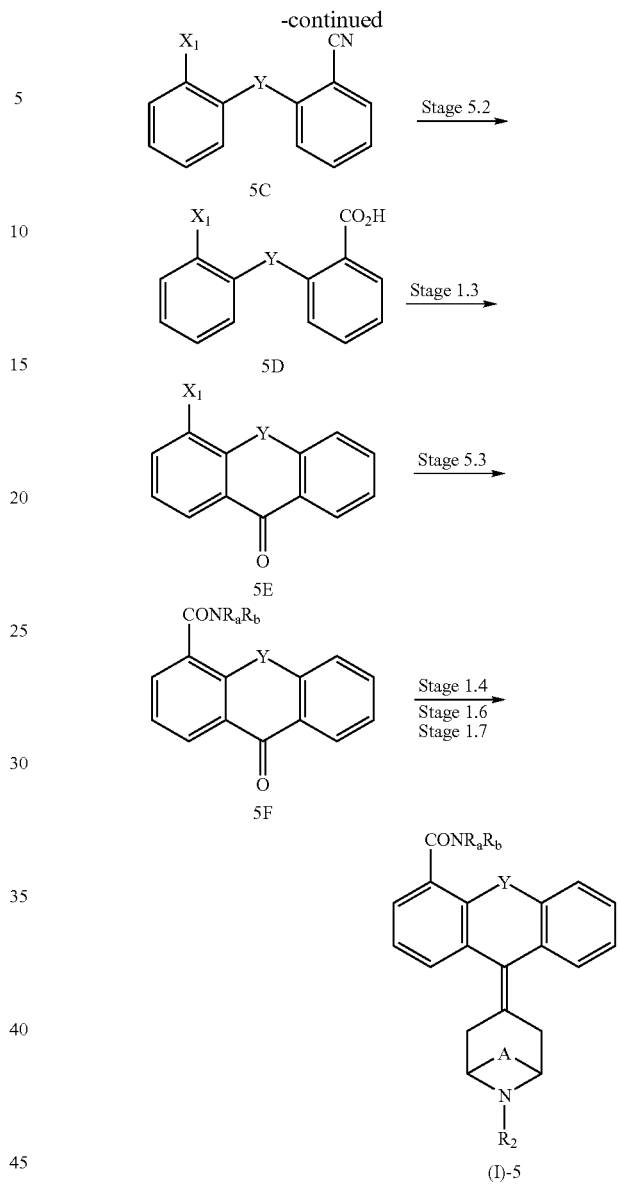

The preparation of compounds of this invention wherein $R_1$ is a carboxamide is illustrated in Scheme 5. In Stage 5.1, the —Y— bridge may be constructed from compounds 5A (wherein $X_1$ is a bromo or chloro substituent) and 5B by a nucleophilic aromatic displacement of an appropriate leaving group $X_2$, wherein $X_2$ is fluoro, chloro, bromo, iodo, or the like. The thus obtained intermediate 5C consists of two functionalized benzene rings connected by an oxygen or sulfer linker, —Y—. One benzene ring must bear a precursor to a carboxamide such as a nitrile or a carboxylic acid, positioned ofthoto the linker —Y—, and the other benzene ring must bear a halogen such as bromine (herein represented as $X_1$), positioned ortho to —YH, that can later be converted to a carboxamide. The compounds of formula 5D are then obtained by hydrolysis of the nitrile of compounds of formula 5C (Stage 5.2) while in the presence of an alkali metal hydroxide.

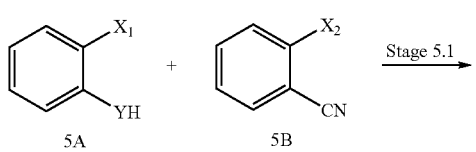

The conversion of compounds of type 5D to compounds of type 5E can be accomplished as previously described in Stage 1.3, using, for instance, $BF_3 \cdot Et_2O$-trifluoroacetic anhydride or polyphosphoric acid. Alternatively, the cyclization may be effected by converting the acid functionality of compounds of formula 5D to an acid chloride, for instance with thionyl chloride or oxalyl chloride, followed by Friedel-Crafts ring closure in the presence of a Lewis acid, such as aluminum chloride.

To perform Stage 5.3, the halogen $X_1$ is converted to a carboxamide, wherein $R_a$ and $R_b$ are each hydrogen or $C_{1-4}$alkanyl. Halogen $X_1$ may be converted to an ester via alkoxycarbonylation using carbon monoxide, an aliphatic alcohol, a trialkanyl amine, and a palladium catalyst such as bis(triphenylphosphine) palladium(II)dichloride. Subsequently, the thus obtained ester may be hydrolyzed to a carboxylic acid and coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the ester may be converted directly to the amide by the action of a dimethylaluminum amide. Finally, the halogen $X_1$ can be displaced with a cyano group, which can then be hydrolyzed to the corresponding amide or acid.

The conversion of compounds of formula 5F to compounds of formula (I)-5 can be accomplished by performing Stages 1.4, 1.6 and 1.7 as described for Scheme 1.

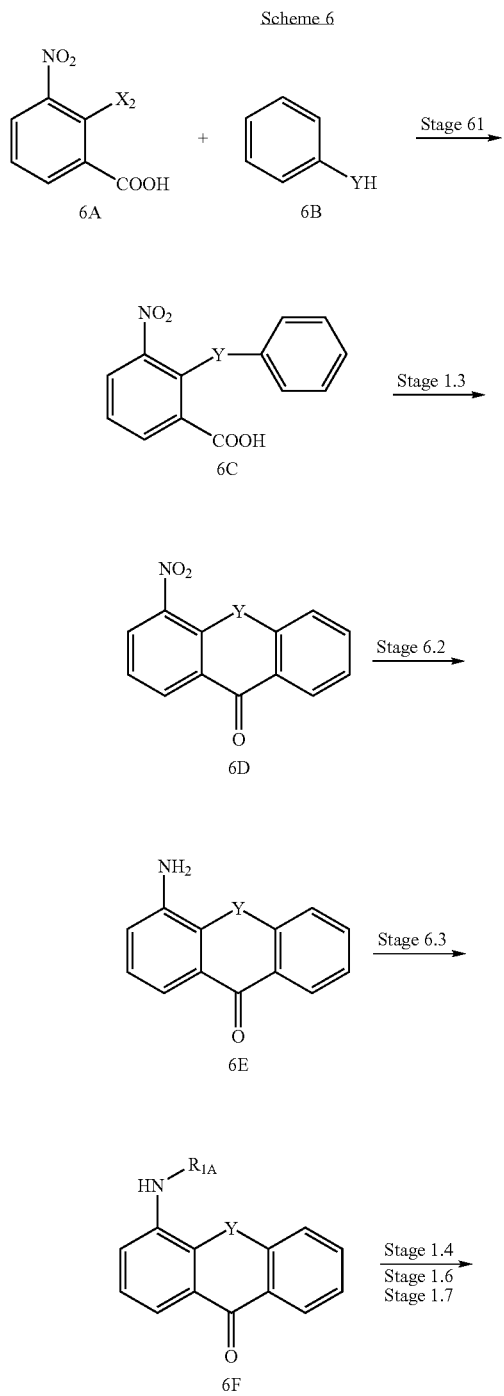

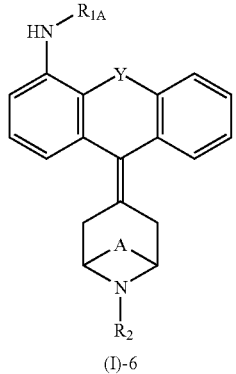

The preparation of compounds of this invention wherein $R_1$ is $C_{6-10}$arylamino or pyridinylamino is illustrated in Scheme 6, ($R_{1A}$ is a $C_{6-10}$aryl or pyridinyl). In Stage 6.1, the —Y— bridge may be constructed from compounds 6A and 6B by a nucleophilic aromatic displacement of an appropriate leaving group $X_2$, as previously defined herein. The thus obtained intermediate 6C consists of two functionalized benzene rings connected by an oxygen or sulfur linker —Y—. One benzene ring must bear a precursor to an amine such as a nitro group, positioned ortho to the linker —Y—, and a carboxylic acid or equivalent such as nitrite, also positioned ortho to the linker —Y—.

The conversion of compounds of formula 6C to compounds of formula 6D can be accomplished as previously described in Stage 1.3, using, for instance, $BF_3.Et_2O$-trifluoroacetic anhydride or polyphosphoric acid. Alternatively, the cyclization may be effected by converting the acid functionality of compounds of formula 6C to an acid chloride, for instance with thionyl chloride or oxalyl chloride, followed by Friedel-Crafts ring closure in the presence of a Lewis acid, such as aluminum chloride.

The conversion of compounds of formula 6D to compounds of formula 6E can be accomplished via catalytic reduction of the nitro group to the corresponding amine using standard hydrogenation conditions in the presence of palladium metal. Installation of an $R_{1A}$ substituent can be accomplished via transition metal-mediated coupling reactions with aryl halides or pyridinyl halides in the presence of a suitable catalyst such as $Pd_2(dba)_3$ or the like, a suitable ligand such as Xanthphos or the like, and a base, such as potassium tert-butoxide or cesium carbonate.

The conversion of compounds of formula 6F to compounds of formula (I)-6 can be accomplished by performing Stages 1.4, 1.6 and 1.7 as described for Scheme 1.

Compounds of Formula (I) that are chiral may be separated into their enantiomers by chromatography on a chiral stationary phase following Stages 1.4, through 1.7. Alternatively, the basic compounds of the present invention may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., J. Org. Chem. 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS), circular dichroism (CD), and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC. CD spectra were generated on a Jasco J-710 spectropolarimeter. Specific conditions were as follows: cell length: 0.1 cm; concentration: 0.238M in methanol); temperature: 25° C.; Ch2-mode: HT voltage; Range 350-200 nm; Band with: 1.0 nm; Sensitivity: 20 mdeg; Resolution: 0.2 nm; Response: 2 sec; Speed: 100 nm/min; Accumulation: 2 scans.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

| Abbreviations | |
|---|---|
| CD = | circular dichroism |
| DMF = | N,N-dimethylformamide |
| dppf = | diphenylphosphinoferrocene |
| h/hr = | hour(s) |
| Me = | methyl |
| min = | minute(s) |
| PPA = | polyphosphoric acid |
| t-Boc = | tert-butoxycarbonyl |
| TFA = | trifluoroacetic acid |
| THF = | tetrahydrofuran |

EXAMPLES

Examples A

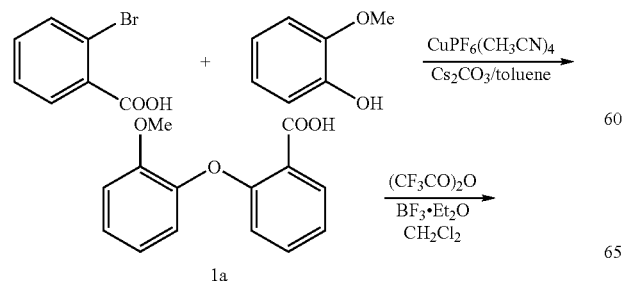

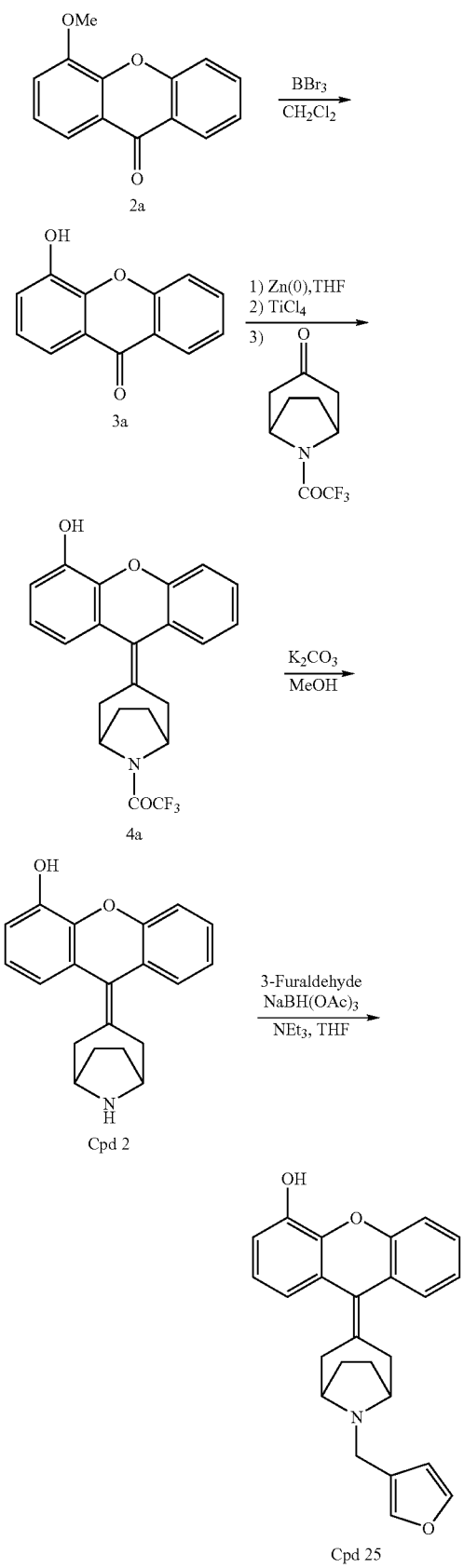

Procedure 1

2-(2-Methoxy-phenoxy)-benzoic acid, 1a

Tetrakis(acetonitrile)copper(I) hexafluorophosphate (4.62 g, 12.4 mmol), cesium carbonate (32 g, 98 mmol), 2-bromobenzoic acid (10g, 49. 7 mmol) and 2-methoxyphenol (6.17 g, 49.7 mmol) were combined in toluene (100 mL), and the mixture was heated to reflux for 15 hr. Ethyl acetate (200 mL) and 1N HCl (200 mL) were added, and the organic layer was separated. The organic layer was dried over $MgSO_4$, filtered, and evaporated to yield 16.8 g of Compound 1a. The residue was used without further purification. MS m/z (M-H)⁻ 243.1.

Procedure 2

4-Methoxy-xanthen-9-one, 2a

To a suspension of 2-(2-methoxy-phenoxy)-benzoic acid (16.8 g, 68.8 mmol) in methylene chloride (100 mL) at 0° C. was added dropwise trifluoroacetic anhydride (12.7 mL, 89.4 mmol), and the reaction was stirred for 30 min at 0° C. At that time, boron trifluoride diethyl etherate (1.29 mL, 10.3 mmol) was added dropwise. The reaction was stirred overnight at rt, poured into $H_2O$, and washed with brine. The organic phase was dried over $MgSO_4$, filtered, and concentrated to give 12.4 g (54.8 mmol) of Compound 2a.

Procedure 3

4-Hydroxy-xanthen-9-one, 3a

To a solution of 4-methoxy-xanthen-9-one (12 g, 53 mmol) in methylene chloride (100 mL) at 0° C. was added a 1M solution of boron tribromide in methylene chloride (160 mL, 160 mmol) and the mixture was stirred at rt for 2 h. The reaction was slowly poured into a solution of ammonia in methanol (2M). The reaction was concentrated under reduced pressure and the resulting residue was partitioned between 1N HCl and methylene chloride. The organic phase was separated, dried over $MgSO_4$, filtered, and evaporated to afford 7.5 g of Compound 3a, without further purification. MS m/z (M-H)⁻ 243.1.

Procedure 4

2,2,2-Trifluoro-1-[3-(4-hydroxy-xanthen-9-ylidene)-8-aza-bicyclo[3.2.1]oct-8-yl]-ethanone, 4a A suspension of zinc metal dust (16.9 g, 259 mmol) in THF (150 mL) under Argon at 5° C. was treated dropwise with titanium (IV) tetrachloride (14.3 mL, 130 mmol). The reaction was refluxed for 2 h. The heat was removed and 4-hydroxy-xanthen-9-one (6.92 g, 46 mmol) and N-trifluoroacetyl-nortropinone (7.18 g, 32.5 mmol) were added, The reaction was refluxed for another 2 h. The reaction was cooled, filtered, and evaporated. The residue was partitioned in chloroform:ethyl acetate and 1N HCl. The organic phase was separated, dried, over $MgSO_4$, filtered and evaporated to give 13.22 g of Compound 4a. MS m/z=402.0 (MH⁺).

Procedure 5

9-(8-Aza-bicyclo[3.2.1]oct-3-ylidene)-9H-xanthen-4-ol, Cpd 2

Potassium carbonate (7.21 g, 52 mmol) was added to a solution of Compound 4a (7.27 g, 18 mmol) in methanol (60 mL), and the reaction was stirred overnight. The reaction was filtered and then ion exchange resin was added (100 g, AG 50W-X210) and the reaction stirred 1 h. The resin was collected by filtration and washed sequentially with water (50 mL) and then methanol (50 mL). The resin was then treated with ammonia in methanol (2M, 500 mL) for 1 h before being collected by filtration again. The filtrate was concentrated under reduced pressure to afford Compound 2 (2.1 g).

Procedure 6

9-(8-Furan-3-ylmethyl-8-aza-bicyclo[3.2.1]oct-3-ylidene)-9H-xanthen-4-ol, Cpd 25

A portion of 9-(8-Aza-bicyclo[3.2.1]oct-3-ylidene)-9H-xanthen-4-ol trifluoroacetate salt (0.10 g, 0.23 mmol), 3-furaldehyde (0.025 g, 0.26 mmol), triethylamine (0.036 g, 0.35 mmol, Aldrich), and sodium triacetoxyborohydride (0.065 g, 0.30 mmol) were stirred in THF (4 mL) overnight. The solvent was evaporated and the residue dissolved in methanol (3 mL) and 1N aqueous HCl (1 mL). The solution was injected onto a prep reverse phase HPLC. The appropriate fractions were lyophilized to afford 9-(8-furan-3-ylmethyl-8-aza-bicyclo[3.2.1]oct-3-ylidene)-9H-xanthen-4-ol (0.046 g, 0.11 mmol, 50% yield, MH⁺ 386.17).

Example B

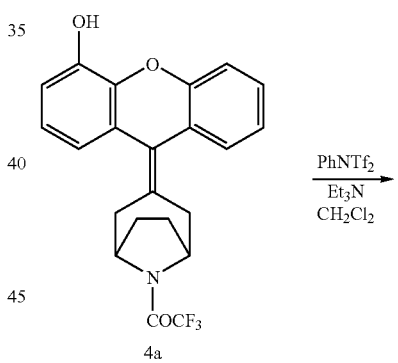

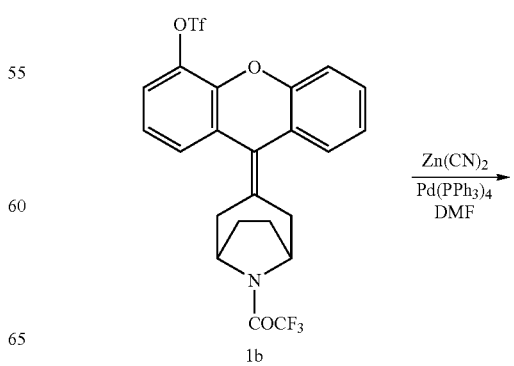

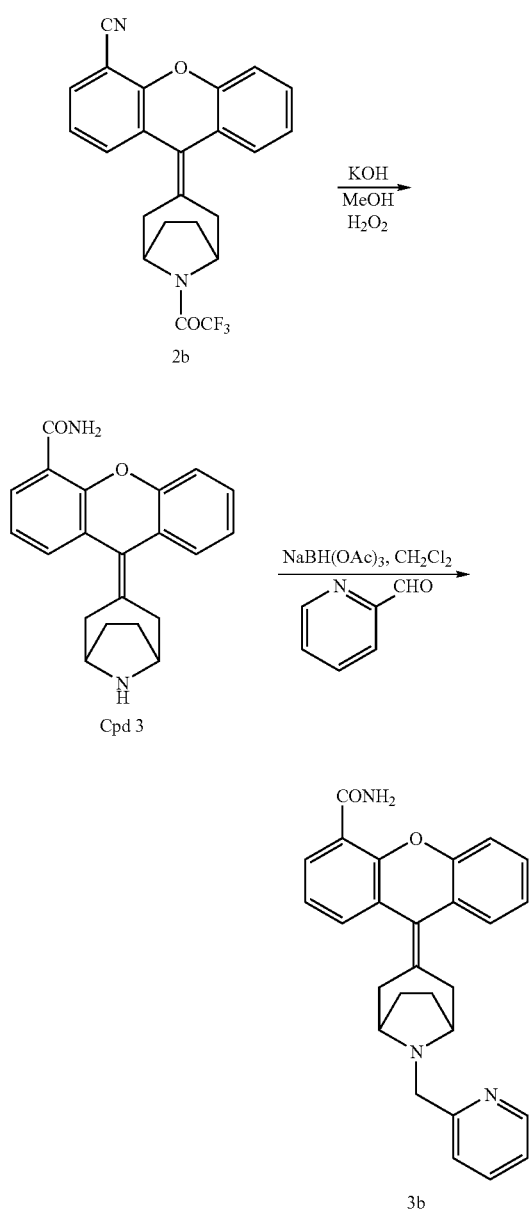

Procedure 7

Trifluoromethanesulfonic acid 9-[8-(2,2,2-trifluoroacetyl)-8-aza-bicyclo[3.2.1]oct-3-ylidene]-9H-xanthen-4-yl ester, 1b 2,2,2-Trifluoro-1-[3-(4-hydroxy-xanthen-9-ylidene)-8-aza-bicyclo[3.2.1]oct-8-yl]-ethanone may be dissolved in methylene chloride (0.1M to 2 M solution), cooled to 0° C., and trifluoromethane sulfonic anhydride (1.0 to 1.5 equiv) and triethylamine (1.0 to 2 equiv) may be added dropwise. The solution may be stirred at 0° C. to room temperature for 1 to 5 hrs. After aqueous workup, drying over a suitable drying agent such as sodium sulfate or magnesium sulfate, and evaporation of solvent, Compound 1b may be obtained.

Procedure 8

9-[8-(2,2,2-Trifluoroacetyl)-8-aza-bicyclo[3.2.1]oct-3-ylidene]-9H-xanthene-4-carbonitrile, 2b A solution of trifluoromethanesulfonic acid 9-[8-(2,2,2-trifluoroacetyl)-8-aza-bicyclo[3.2.1]oct-3-ylidene]-9H-xanthen-4-yl ester in a deoxygenated solvent such as dimethyl formamide (0.5 to 2 M solution) may be treated with a catalytic amount of a palladium catalyst such as tetrakis(triphenylphosphine) palladium ( 0.01 to 0.1 equiv) and a cyanide source such as zinc cyanide (1.5 to 3 equiv). The mixture may be heated to 100° C. to 150° C. under an argon atmosphere for 1 to 5 hr. After cooling, the mixture may be partitioned between a saturated sodium bicarbonate solution and an organic solvent such as ethyl acetate. The organic phase may be separated, dried over an appropriate drying agent such as sodium sulfate, filtered, and evaporated. The residue may be purified over silica gel using a mixture of organic solvents or via reverse phase chromatography to yield Compound 2b.

Procedure 9

9-(8-Aza-bicyclo[3.2.1]oct-3-ylidene)-9H-xanthene-4-carboxylic acid amide, Cpd 3

9-[8-(2,2,2-Trifluoroacetyl)-8-aza-bicyclo[3.2.1]oct-3-ylidene]-9H-xanthene-4-carbonitrile may be dissolved in an alcoholic solvent such as methanol (0.05 to 1 M) and treated with a concentrated potassium hydroxide solution (20 to 30%) and a catalytic amount (2 to 5 drops) of hydrogen peroxide solution. The mixture may be heated to reflux for 1 to 6 hr. After cooling, the solution may be extracted with an organic solvent such as ethyl acetate. The organic phase may be dried over a suitable drying agent such as potassium carbonate, filtered, and evaporated. The crude product may be purified via reverse phase column chromatography to yield Compound 3.

9-(8-Pyridin-2-ylmethyl-8-aza-bicyclo[3.2.1]oct-3-ylidene)-9H-xanthene-4-carboxylic acid amide, 3b Following Procedure 6, substituting 9-(8-aza-bicyclo[3.2.1]oct-3-ylidene)-9H-xanthene-4-carboxylic acid amide for 9-(8-aza-bicyclo[3.2.1]oct-3-ylidene)-9H-xanthen-4-ol and 2-pyridylcarboxaldehyde for 3-furaldehyde, Compound 3b may be obtained.

Example C

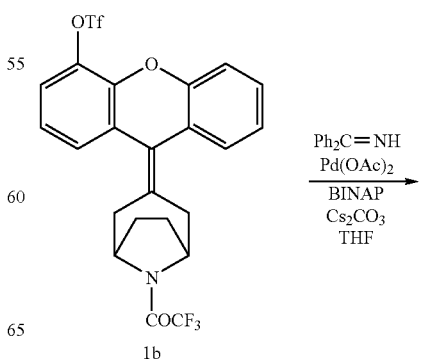

-continued

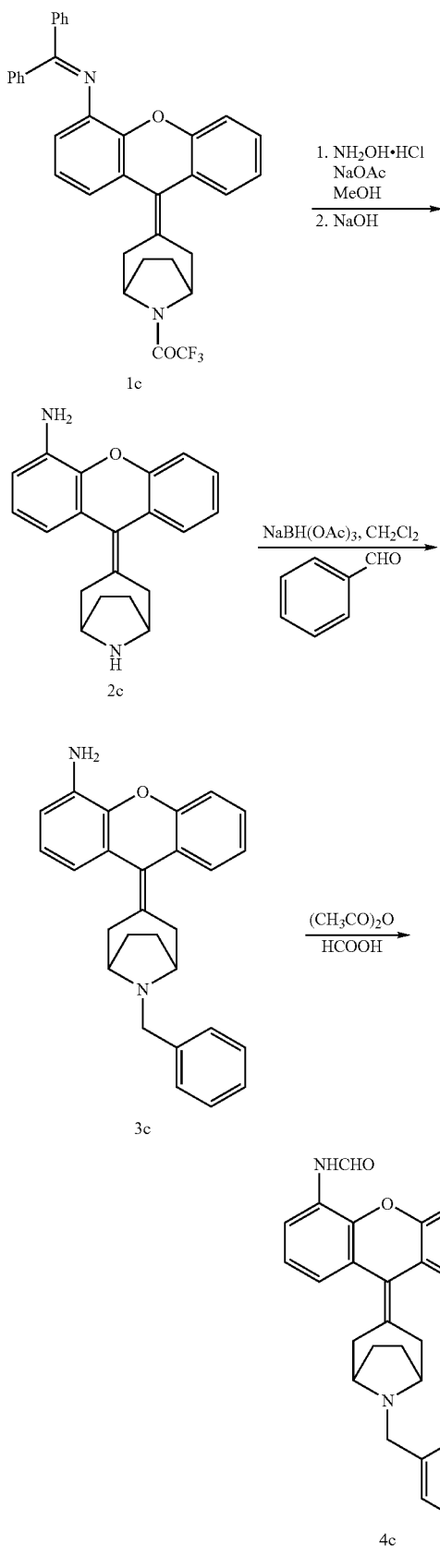

Procedure 10

1-{3-[4-(Benzhydrylidene-amino)-xanthen-9-ylidene]-8-aza-bicyclo[3.2.1]oct-8-yl}-2,2,2-trifluoroethanone, 1c A solution of trifluoromethanesulfonic acid 9-[8-(2,2,2-trifluoroacetyl)-8-aza-bicyclo[3.2.1]oct-3ylidene]-9H-xanthen-4-yl ester in THF (0.1 to 1 M solution) may be treated with a catalytic amount of a palladium catalyst such as palladium acetate (0.01 to 0.05 equiv), BINAP (0.01 to 0.05 equiv), benzophenone imine (1.05 to 1.5 equiv), and cesium carbonate (1.2 to 2 equiv) under an argon atmosphere. The mixture may be heated to reflux for a period of 10 to 24 hr. After removal of the solvent via evaporation, the residue may be taken up in a halogenated solvent such as methylene chloride, and the solution may be washed with water, dried over a suitable drying agent such as magnesium sulfate, filtered, and concentrated. The residue may be purified via column chromatography to yield Compound 1c.

Procedure 11

9-(8-Aza-bicyclo[3.2.1]oct-3-ylidene)-9H-xanthen-4-ylamine, 2c

A solution of 1-{3-[4-(benzhydrylidene-amino)-xanthen-9-ylidene]-8-aza-bicyclo[3.2.1]oct-8-yl}-2,2,2-trifluoroethanone in methanol (0.1 to 1 M solution) may be treated with sodium acetate (2 to 4 equiv) and hydroxylamine hydrochloride (1 to 3 equiv) and stirred at rt for 1 to 4 days. Sodium hydroxide may be added to make the solution basic, and the solution may be stirred at rt for 1 to 5 hr. Methylene chloride and water may be added, and the organic layer may be separated. After drying over a suitable drying agent such as potassium carbonate, filtration, and evaporation, the residue may be purified via reverse phase column chromatography to yield Compound 2c.

Procedure 12

9-(8-Benzyl-8-aza-bicyclo[3.2.1]oct-3-ylidene)-9H-xanthen-4-ylamine, 3c

Following Procedure 6, substituting 9-(8-aza-bicyclo[3.2.1]oct-3-ylidene)-9H-xanthen-4-ylamine for 9-(8-aza-bicyclo[3.2.1]oct-3-ylidene)-9H-xanthen-4-ol and benzaldehyde for 3-furaldehyde, Compound 3c may be obtained.

Procedure 13

N-[9-(8-Benzyl-8-aza-bicyclo[3.2.1]oct-3-ylidene)-9H-xanthen-4-yl]-formamide, 4c Equimolar amounts of acetic anhydride and formic acid may be combined at 0° C. and heated to 50-60° C. for 2 hr to produce acetic formic anhydride. The mixture may be cooled to or below 0° C. and 9-(8-benzyl-8-aza-bicyclo[3.2.1]oct-3-ylidene)-9H-xanthen-4-ylamine may be added. After stirring at) 0° C. for a period of 15 min to 2 hr, the mixture may be evaporated to yield Compound 4c.

Example D

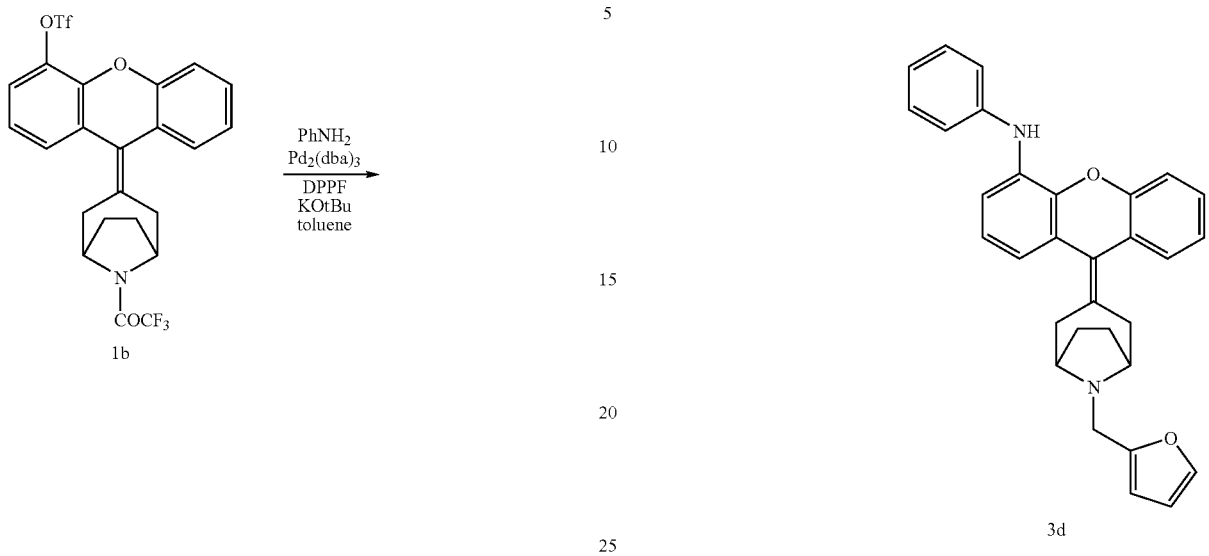

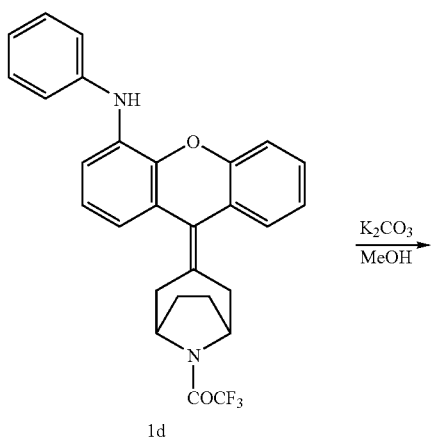

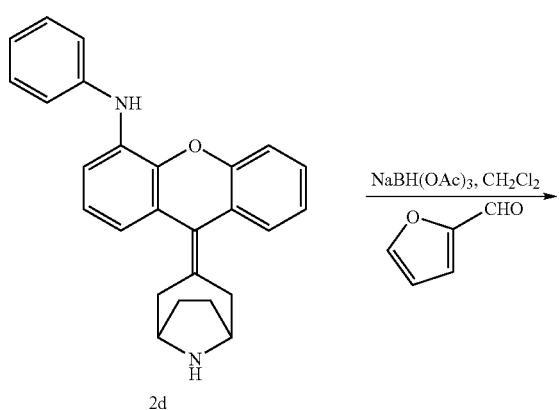

Procedure 14

2,2,2-Trifluoro-1-[3-(4-phenylamino-xanthen-9-ylidene)-8-aza-bicyclo[3.2.1]oct-8-yl]-ethanone, 1d A solution of trifluoromethanesulfonic acid 9-[8-(2,2,2-trifluoroacetyl)-8-aza-bicyclo[3.2.1]oct-3-ylidene]-9H-xanthen-4-yl ester in toluene (0.1 to 2 M solution) may be treated with a catalytic amount of a palladium catalyst such as $Pd_2(dba)_3$ (0.01 to 0.1 equiv), DPPF (0.1 to 0.3 equiv), aniline (2 to 5 equiv), sodium tert-butoxide (1.2 to 2 equiv) under an argon atmosphere. The mixture may be heated to 80° C. for a period of 1 to 10 hr. After filtration and removal of the solvent via evaporation, the residue may be taken up in a halogenated solvent such as methylene chloride, and the solution may be washed with water, dried over a suitable drying agent such as magnesium sulfate, filtered, and concentrated. The residue may be purified via column chromatography to yield Compound 1d.

[9-(8-Aza-bicyclo[3.2.1]oct-3-ylidene)-9H-xanthen-4-yl]-phenylamine, 2d

Following Procedure 5, substituting 2,2,2-trifluoro-1-[3-(4-phenylamino-xanthen-9-ylidene)-8-aza-bicyclo[3.2.1]oct-8-yl]-ethanone for 9-(8-aza-bicyclo[3.2.1]oct-3-ylidene)-9H-xanthen-4-ol, Compound 2d may be obtained.

[9-(8-Furan-2-ylmethyl-8-aza-bicyclo[3.2.1]oct-3-ylidene)-9H-xanthen-4-yl]-phenylamine, 3d Following Procedure 6, substituting [9-(8-aza-bicyclo[3.2.1]oct-3-ylidene)-9H-xanthen-4-yl]-phenylamine for

Example E

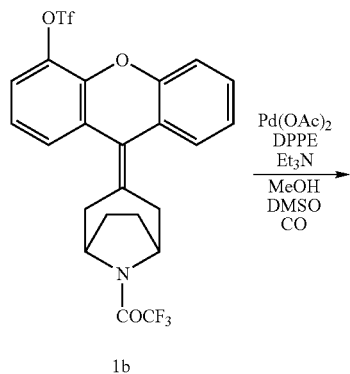

1b

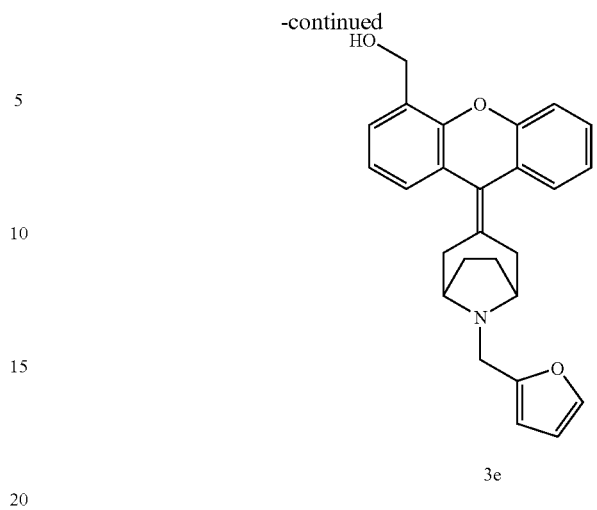

3e

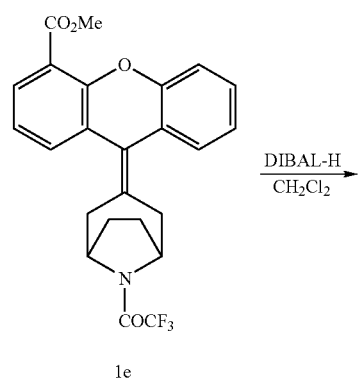

1e

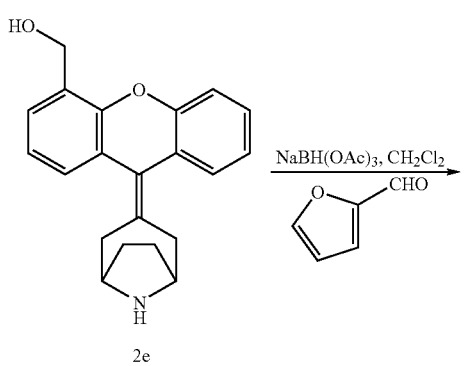

2e

Procedure 15

9-[8-(2,2,2-Trifluoroacetyl)-8-aza-bicyclo[3.2.1]oct-3-ylidene]-9H-xanthene-4-carboxylic acid methyl ester, 1e A solution of trifluoromethanesulfonic acid 9-[8-(2,2,2-trifluoroacetyl)-8-aza-bicyclo[3.2.1]oct-3-ylidene]-9H-xanthen-4-yl ester in deoxygenated DMSO (0.1 to 1 M solution) may be treated with a catalytic amount of a palladium catalyst such as $Pd(OAc)_2$ (0.01 to 0.1 equiv), bis(diphenylphosphino)ethane (0.01 to 0.1 equiv), methanol (100 to 1000 equiv), triethylamine (1.1 to 2 equiv) and purged with CO by bubbling a stream of CO gas through the solution for 5 min. The mixture may be heated to 80° C. for a period of 1 to 10 hr. After cooling, the mixture may be partitioned between equal amounts of water and an organic solvent such as ethyl acetate. The organic layer may be separated, dried over an appropriate drying agent such as magnesium sulfate, filtered, and evaporated. The residue may be purified via column chromatography to yield Compound 1e.

Procedure 16

[9-(8-Aza-bicyclo[3.2.1]oct-3-ylidene)-9H-xanthen-4-yl]-methanol, 2e

A solution of 9-[8-(2,2,2-trifluoroacetyl)-8-aza-bicyclo[3.2.1]oct-3-ylidene]-9H-xanthene-4-carboxylic acid methyl ester in methylene chloride (0.001 to 1 M solution) at −78° C. may be treated with diisobutyl aluminum hydride (1M in cyclohexane; 2 to 10 equiv), and the mixture may be allowed to slowly warm up to 0° C. After stirring at that temperature for a period of 1 to 5 hr, an aqueous solution of Rochelle's salt may be added. The mixture may be extracted with an appropriate organic solvent such as ethyl acetate, and the organic layer may be dried over a suitable drying agent such as potassium carbonate. After filtration and evaporation, the residue may be purified via reverse phase column chromatography to yield Compound 2e.

[9-(8-Furan-2-ylmethyl-8-aza-bicyclo[3.2.1]oct-3-ylidene)-9H-xanthen-4-yl]-methanol, 3e Following Procedure 6, substituting [9-(8-aza-bicyclo[3.2.1]oct-3-ylidene)-9H-xanthen-4-yl]-methanol for 9-(8- aza-bicyclo[3.2.1]oct-3-ylidene)-9H-xanthen-4-ol and 2-furaldehyde for 3-furaldehyde, Compound 3e may be obtained.

Example F

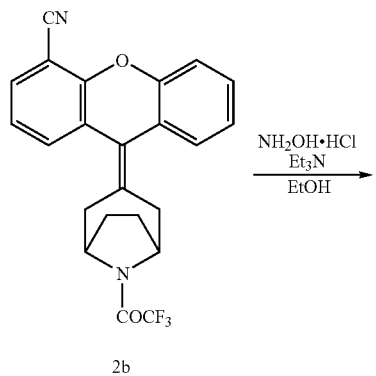

2b

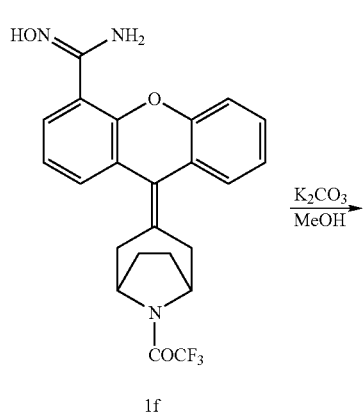

1f

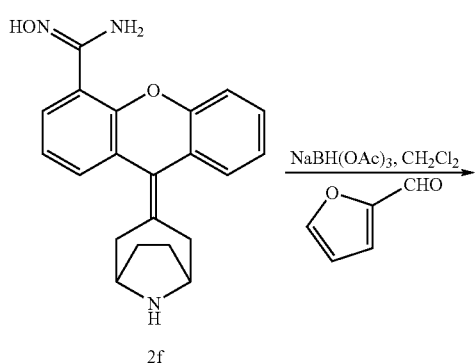

2f

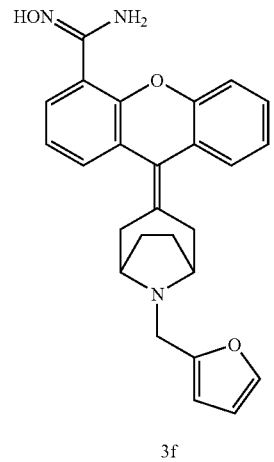

3f

Procedure 17

N-Hydroxy-9-[8-(2,2,2-trifluoro-acetyl)-8-aza-bicyclo[3.2.1]oct-3-ylidene]-9H-xanthene-4-carboxamidine, 1f A solution of 9-[8-(2,2,2-trifluoroacetyl)-8-aza-bicyclo[3.2.1]oct-3-ylidene]-9H-xanthene-4-carbonitrile in ethanol (0.1 to 2 M solution) may be treated with hydroxylamine hydrochloride (1 to 2 equiv) and triethylamine (2 to 3 equiv) and may be heated to reflux for a period of 1 to 10 hr. After cooling, the mixture may be evaporated under reduced pressure, and the residue may be partitioned between equal amounts of water and an organic solvent such as ethyl acetate. The organic layer may be separated, dried over an appropriate drying agent such as magnesium sulfate, filtered, and evaporated. The residue may be purified via column chromatography to yield Compound 1f.

9-(8-Aza-bicyclo[3.2.1]oct-3-ylidene)-N-hydroxy-9H-xanthene-4-carboxamidine, 2f

Following Procedure 5, substituting N-Hydroxy-9-[8-(2,2,2-trifluoro-acetyl)-8-aza-bicyclo[3.2.1]oct-3-ylidene]-9H-xanthene-4-carboxamidine for 9-(8-aza-bicyclo[3.2.1]oct-3-ylidene)-9H-xanthen-4-ol, Compound 2f may be obtained.

9-(8-Furan-2-ylmethyl-8-aza-bicyclo[3.2.1]oct-3-ylidene)-N-hydroxy-9H-xanthene-4-carboxamidine, 3f Following Procedure 6, substituting 9-(8-Aza-bicyclo[3.2.1]oct-3-ylidene)-N-hydroxy-9H-xanthene-4-carboxamidine for 9-(8-aza-bicyclo[3.2.1]oct-3-ylidene)-9H-xanthen-4-ol and 2-furaldehyde for 3-furaldehyde, Compound 3f may be obtained.

Example G

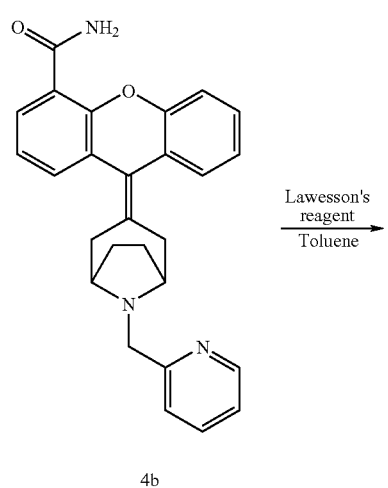

4b

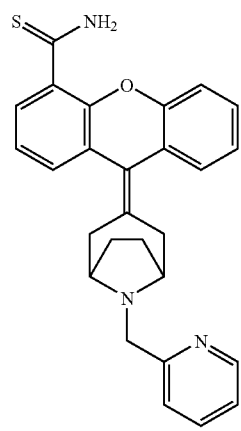

1g

Procedure 18

N-Hydroxy-9-[8-(2,2,2-trifluoro-acetyl)-8-aza-bicyclo[3.2.1]oct-3-ylidene]-9H-xanthene-4-carboxamidine, 1g To a solution of 9-(8-pyridin-2-ylmethyl-8-aza-bicyclo[3.2.1]oct-3-ylidene)-9H-xanthene-4-carboxylic acid amide in toluene (0.05 to 1 M solution), Lawesson's reagent (1.2 to 2 equiv) may be added, and the mixture may be irradiated in a microwave oven for 5 to 20 min, An organic solvent may be added to the cooled mixture, and the solution may be washed with an equal amount of water. The organic layer may be separated, dried over a suitable drying agent such as sodium sulfate, filtered, and evaporated. The residue may be purified via reverse phase column chromatography to yield Compound 1g.

Example H

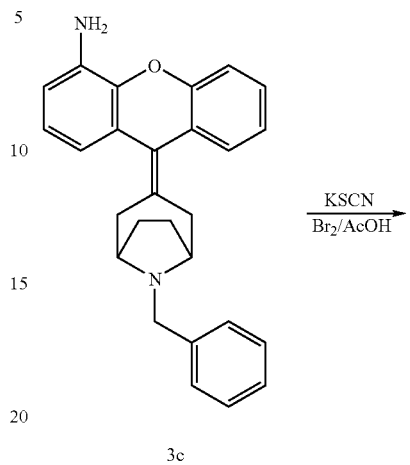

3c

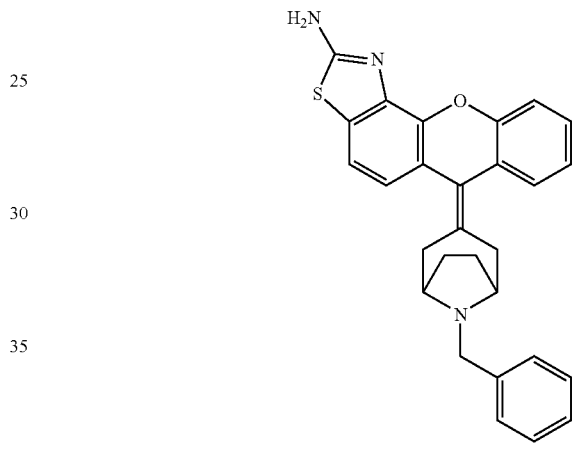

1h

Procedure 19

6-(8-Benzyl-8-aza-bicyclo[3.2.1]oct-3-ylidene)-6H-11-oxa-3-thia-1-aza-cyclopenta[a]anthracen-2-ylamine, 1h To a solution of 9-(8-benzyl-8-aza-bicyclo[3.2.1]oct-3-ylidene)-9H-xanthen-4-ylamine in glacial acetic acid (0.1 to 1 M solution) may be added potassium thiocyanate (2 equiv). A solution of bromine (1 equiv) in glacial acetic acid (0.5 to 2 M solution) may be added slowly, and the resulting mixture may be stirred at rt for 1 to 4 hr. The solution may be basified with a sodium hydroxide solution (5 to 20%), and extracted with a suitable organic solvent such as ethyl acetate. The organic layer may be separated, dried over sodium sulfate, filtered, and evaporated. The residue may be purified via column chromatography to yield Compound 1h.

Example I

Enantiomers 5 and 6 in Table 1 herein were obtained via chiral separation of the racemic material. The chiral separation was performed on a preparative Daicel Chiralpak® AD column (Amylose tris-(3,5-dimethylphenylcarbamate, coated on 20 μm silica gel; 500 gram; 5 cm ID; 41 cm length) using an isocratic mixture of heptane/methanol/ethanol (80/10/10) as eluent. The analytes were monitored using a wavelength of 220 nm. Compounds 8 and 9 were obtained via deprotection of compounds 5 and 6, respectively.

Example J

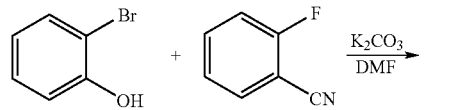

Procedure 20

2-(2-Bromophenoxy)-benzonitrile, 1j

To a solution of 2-bromophenol (6.0 mL, 51.7 mmol) in DMF (80 mL) was added potassium carbonate (7.16 g, 51.7 mmol), and the mixture was allowed to stir for 10 min ar rt. 2-Fluorobenzonitrile (5.62 mL, 82.6 mmol) was added and the mixture was heated to 100° C. for 40 h. The mixture was allowed to cool to rt, poured onto ice, filtered, washed with water, and dried to yield 13.0 g (91.7%) of title compound 2-(2-bromophenoxy)-benzonitrile 1j.

Procedure 21

2-(2-Bromophenoxy)-benzoic acid, 2j

To a solution of compound 2-(2-bromophenoxy)-benzonitrile 1j (12.8 g, 46.7 mmol) in ethanol (150 mL) was added a 3N sodium hydroxide solution (15 mL), and the mixture was heated to reflux for 16 h. The mixture was allowed to cool to rt and evaporated. The residue was diluted with water, and concentrated hydrochloric acid was added dropwise until the mixture was acidic. The solid was separated via filtration, washed with water, and dried to yield 12.8 g (93.5%) of title compound 2j.

Procedure 22

4-Bromo-xanthen-9-one, 3j

To a solution of 2-(2-bromophenoxy)-benzoic acid 2j (11.8 g, 40.3 mmol) in dichloromethane (200 mL) was added trifluoroacetic anhydride (6.3 mL, 44.6 mmol), and the mixture was stirred for 30 min at rt. Boron trifluoride etherate (0.51 mL, 4.03 mmol) was added, and the mixture was stirred for 2 h at rt. The mixture was cooled in an ice bath, and a 3N sodium hydroxide solution (100 mL) was added under vigorous stirring. The organic layer was separated, washed with water and brine, dired over magnesium sulfate, filtered, and evaporated. The residue was purified over silica gel using dichloromethane as eluent. The desired fractions were collected, and evaporated to yield 10.18 g (91.8%) of title compound 3j.

Procedure 23

9-Oxo-9H-xanthene-4-carboxylic acid methyl ester, 4j

To a solution of 4-bromo-xanthen-9-one 3j (10 g, 36.35 mmol) and triethylamine (15.2 mL, 109 mmol) in a mixture of dimethylformamide (80 mL) and methanol 940 mL) was added $PdCl_2(dppf).CH_2Cl_2$ (3 g, 3 mmol), and sparged with carbon monoxide. The mixture was heated for 2 days at 80° C., poured into water, and the solid was collected via filtration. The solid was washed with water, air-dried, and dissolved in dichloromethane. The solution was filtered, dried over magnesium sulfate, filtered, and evaporated. The residue was purified via flash column chromatography (eluent gradient: 0.2% to 3% methanol in dichloromethane to yield 8.0 g (86.6%) of title compound 4j.

Procedure 24

9-Oxo-9H-xanthene-4-carboxylic acid, 5j

To a suspension of 9-oxo-9H-xanthene-4-carboxylic acid methyl ester 4j (2.0 g, 7.87 mmol) in methanol (30 mL) was added a 3N sodium hydroxide solution (3.2 mL), and the mixture was heated to reflux for 2 h. The solvent was evaporated and the residue was dissolved in water (50 mL). The solution was filtered, acidified with concentrated hydrochloric acid, and a precipitate formed. The solid was separated via filtration, washed with water, and air-dried to yield 1.9 g (quant.) of title compound 5j.

Procedure 25

9-Oxo-9H-xanthene-4-carboxylic acid amide, 6j

To a solution of 9-oxo-9H-xanthene-4-carboxylic acid 5j (1.84 g, 7.66 mmol) in dimethylformamide (20 mL) was added N,N-diisopropyl-N-ethylamine (1.74 mmol, 9.96 mmol) and O(benzotriazol-1-yl)-N,N,N',N'-tetramethyl-uronium hexafluorophosphate (2.9 g, 7.66 mmol). The mixture was stirred for 30 min at rt, and ammonium hydroxide (2 mL) was added. The mixture was stirred for 3 h, poured onto ice, and the solid was collected via filtration. The solid was washed with water and air-dried to yield 1.78 g (97.2% of title compound 6j.

9-[8-(2,2,2-Trifluoroacetyl)-8-azabicyclo[3.2.1]oct-3-ylidene]-9H-xanthene-4-carboxylic acid amide, 7j Using an adaptation of the method described in Procedure 4, substituting compound 6j for compound 3a, the title compound 7j was obtained.

9-(8-Azabicyclo[3.2.1]oct-3-ylidene)-9H-xanthene-4-carboxylic acid amide, Cpd 3

Using an adaptation of the method described in Procedure 5, substituting compound 7j for compound 4a, the title compound 3 was obtained as a TFA salt.

9-(8-Furan-3-ylmethyl-8-azabicyclo[3.2.1]oct-3-ylidene)-9H-xanthene-4-carboxylic acid amide, Cpd 4

Using an adaptation of the method described in Procedure 6, substituting 9-(8-azabicyclo[3.2.1]oct-3-ylidene)-9H-xanthene-4-carboxylic acid amide for the trifluoroacetate salt of compound 2, the title compound 4 was obtained as a TFA salt.

Procedure 26

(+)-9-[8-(2,2,2-Trifluoroacetyl)-8-azabicyclo[3.2.1] oct-3-ylidene]-9H-xanthene-4-carboxylic acid amide (Cpd 36)

and (−)-9-[8-(2,2,2-Trifluoroacetyl)-8-azabicyclo[3.2.1] oct-3-ylidene]-9H-xanthene-4-carboxylic acid amide (Cpd 38)

The (+) and (−) enantiomers of compound 7f (Cpds 36 and 38), in Table 1 herein were separated on a preparative chiralpak AD column (500 grams of 20 micron material, 5×41 cm) using hexane/methanol/ethanol (50/25/25) as eluent, The analytes were monitored using a wavelength of 220 nm. For analytical work, the same column material was used (chiralpak AD, 4.6×50 mm), and the same solvents, but in 80/10/10 proportion Enant (A): -9-(8-Azabicyclo[3.2.1]oct-3-ylidene)-9H-xanthene-4-carboxylic acid amide, Cpd 37

Using an adaptation of the method described in Procedure 5 substituting (+)-9-[8-(2,2,2-trifluoroacetyl)-8-azabicyclo [3.2.1]oct-3-ylidene]-9H-xanthene-4-carboxylic acid amide 36 for 2,2,2-trifluoro-1-[3-(4-hydroxyxanthen-9-ylidene)-8-azabicyclo[3.2.1]oct-8-yl]-ethanone 4a, title compound 37 was obtained as a TFA salt.

Enant (B): 9-(8-Azabicyclo[3.2.1]oct-3-ylidene)-9H-xanthene-4-carboxylic acid amide, Cpd 39

Using an adaptation of the method described in Procedure 5, substituting (−)-9-[8-(2,2,2-trifluoroacetyl)-8-azabicyclo[3.2.1]oct-3-ylidene]-9H-xanthene-4-carboxylic acid amide 38 for 2,2,2-trifluoro-1-[3-(4-hydroxyxanthen-9-ylidene)-8-azabicyclo[3.2.1]oct-8-yl]-ethanone 4a, the title compound 39 was obtained as a TFA salt.

Example K

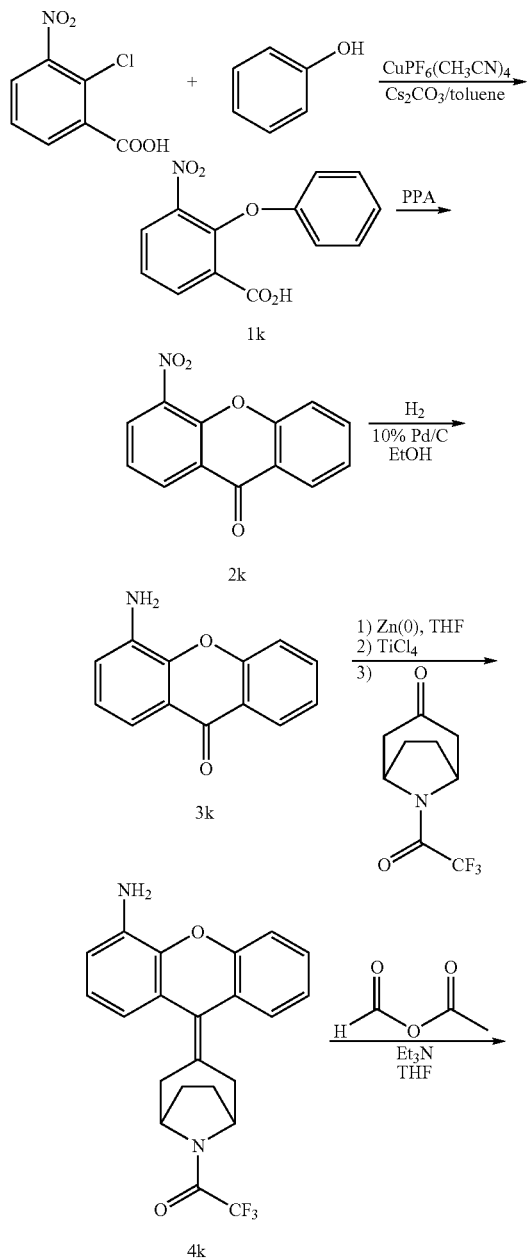

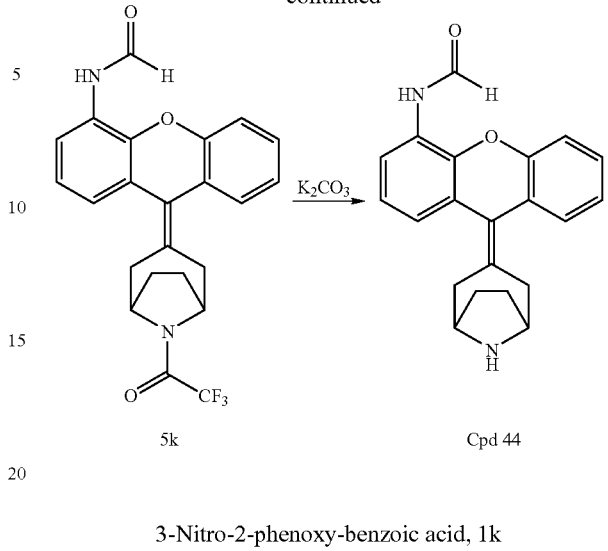

3-Nitro-2-phenoxy-benzoic acid, 1k

Using an adaptation of the method described in Procedure 1, substituting 2-chloro-3-nitrobenzoic acid for 2-bromobenzoic acid and phenol for 2-methoxyphenol, the title compound 1k was obtained.

Procedure 27

4-Nitroxanthen-9-one, 2k

A mixture of 3-nitro-2-phenoxy-benzoic acid 1k (7.1 g, 27.4 mmol) and polyphosphoric acid (140 g) was heated to 120° C. for 4 h. The mixture was allowed to cool to 55° C. and poured onto ice. The mixture was stirred for t 16 h, and the solid was collected via filtration, yielding 5.1 g (78.5%) of title compound 4-nitroxanthen-9-one 2k.

Procedure 28

4-Aminoxanthen-9-one, 3k

A mixture of 4-nitroxanthen-9-one 2k (4.5 g, 18.7 mmol) and 10% palladium on carbon (200 mg) in ethanol (70 mL) was hydrogenated (hydrogen pressure: 55 psi) for 16 h. The catalyst was removed via filtration and the solvent was evaporated to yield 3.5 g (89%) of title compound 4-aminoxanthen-9-one 3k.

1-[3-(4-Amino-xanthen-9-ylidene)-8-aza-bicyclo[3.2.1]oct-8-yl]-2,2,2-trifluoro-ethanone, 4k Using an adaptation of the method described in Procedure 4, substituting compound 3k for compound 3a, the title compound 4k was obtained.

Procedure 29

N-{9-[8-(2,2,2-Trifluoro-acetyl)-8-aza-bicyclo[3.2.1]oct-3-ylidene]-9H-xanthen-4-yl}-formamide, 5k Into a flask was placed acetic anhydride (4 mL) and the reaction was cooled in an ice bath. Upon cooling, formic acid (2 mL) was added and the mixture was heated to 50° C. for 15 min, and then cooled to rt. Upon cooling, the resulting solution (0.6 mL) was added to an ice bath-cooled solution of compound 4k (0.300 g, 6.0 mmol) in THF (2 mL), and the reaction was heated to 50° C. for 1 h. The mixture was cooled to rt, diluted with methylene chloride, and the organic phase was washed sequentially with saturated aqueous sodium bicarbonate solution and brine. The organic phase was dried over MgSO₄, filtered, and concentrated to yield 0.42 g of the title compound 5k.

Procedure 30

N-[9-(8-Azabicyclo[3.2.1]oct-3-ylidene)-9H-xanthen-4-yl]-formamide, Cpd 44

Compound 5k (0.42g, 0.98 mmol) was added to MeOH (10 mL), and K₂CO₃ (1 g) was added. The mixture was stirred for 3 h at rt. After that time, the solid was collected by vacuum filtration. The resulting filtrate was concentrated in vacuo. Water was added to the resulting residue and the mixture was stirred for 30 min. The solid was collected by vacuum filtration and purified by reverse phase HPLC to yield the title compound 44 (159 mg, 37%).

9-(8-Azabicyclo[3.2.1]oct-3-ylidene)-9H-xanthen-4-ylamine, Cpd 41

Using an adaptation of the methods described in Procedures 4 and 5, substituting 4-aminoxanthen-9-one 3k for 4-hydroxy-xanthen-9-one 3a in Procedure 4, the title compound 41 was obtained.

Example L

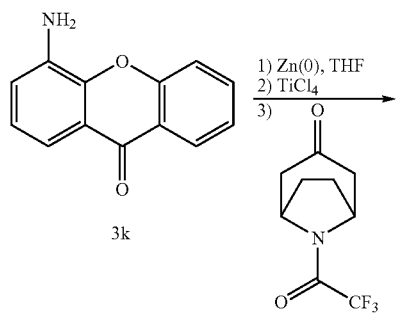

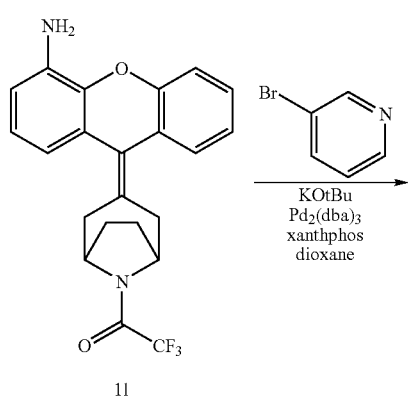

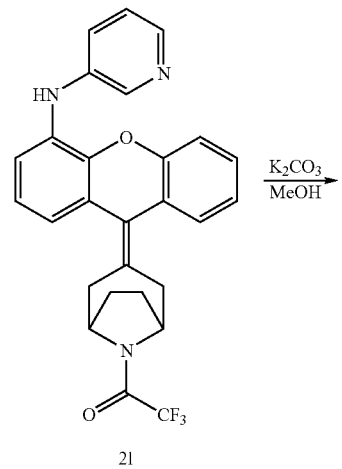

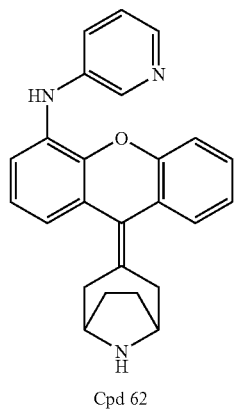

1-[3-(4-Aminoxanthen-9-ylidene)-8-azabicyclo[3.2.1]oct-8-yl]-2,2,2-trifluoro-ethanone, 11

Using an adaptation of the methods described in Procedure 4, substituting 4-aminoxanthen-9-one 3k for 4-hydroxy-xanthen-9-one 3a, the title compound 11 was obtained.

Procedure 31

[9-(8-Azabicyclo[3.2.1]oct-3-ylidene)-9H-xanthen-4-yl]-pyridin-3-yl-amine, Cpd 62

To a solution of 1-[3-(4-aminoxanthen-9-ylidene)-8-azabicyclo[3.2.1]oct-8-yl]-2,2,2-trifluoro-ethanone 11 (100 mg, 0.25 mmol) in dioxane (6 mL) was added 3-bromopyridine (0.05 mL, 0.5 mmol), 1M potassium tert-butoxide in tetrahydrofuran (1.2 mL, 1.2 mmol), Pd₂(dba)₃ (9 mg, 0.0125 mmol) and Xanthphos (4.5 mg, 0.0125 mmol). The mixture was irradiated in a microwave reactor for 30 min at 120° C. The mixture was allowed to cool to rt, water was added, and the mixture was extracted with ethyl acetate. The organic phase was separated, dried over Na₂SO₄, filtered, and evaporated. The residue was purified via reverse phase chromatography to yield 15 mg (12%) of title compound 62 as a TFA salt.

[9-(8-Azabicyclo[3.2.1]oct-3-ylidene)-9H-xanthen-4-yl]-phenylamine, Cpd 64

Using an adaptation of the methods described in Procedure 31, substituting bromobenzene for 3-bromopyridine, the title compound 64 was obtained.

[9-(8-Azabicyclo[3.2.1]oct-3-ylidene)-9H-xanthen-4-yl]-(4-chlorophenyl)-amine, Cpd 61

Using an adaptation of the methods described in Procedures 31, 4 and 5, substituting 4-chlorobromobenzene for 3-bromopyridine and cesium carbonate for potassium tert-butoxide in Procedure 30, the title compound 61 was obtained.

Example M

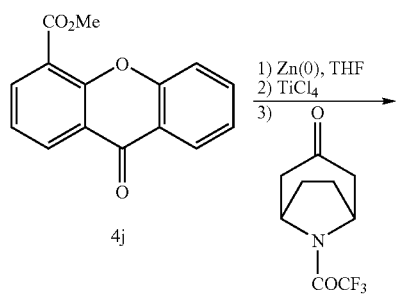

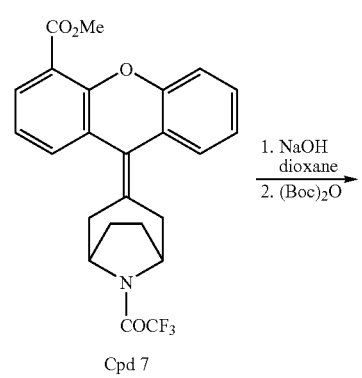

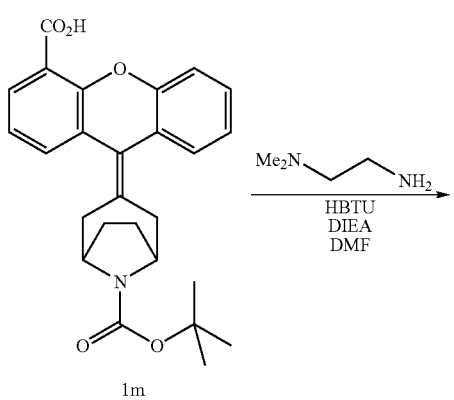

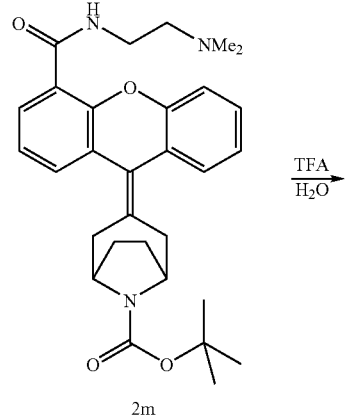

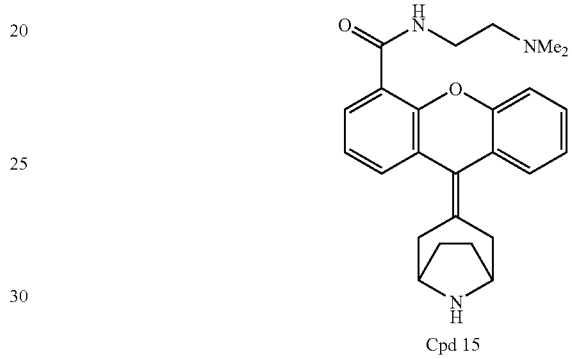

9-[8-(2,2,2-Trifluoroacetyl)-8-azabicyclo[3.2.1]oct-3-ylidene]-9H-xanthene-4-carboxylic acid methyl ester, Cpd 7

Using an adaptation of the method described in Procedure 4, substituting 9-oxo-9H-xanthene-4-carboxylic acid methyl ester 4j for 4-hydroxy-xanthen-9-one 3a, the title compound 7 was obtained.

Procedure 32

3-(4-Carboxyxanthen-9-ylidene)-8-azabicyclo[3.2.1]octane-8-carboxylic acid tert-butyl ester, 1m To a solution of compound 7 (2.2 g, 4.96 mmol) in dioxane (25 mL) was added a 3N sodium hydroxide solution (3.5 mL) and the mixture was heated to reflux for 3 h. Additional 3N sodium hydroxide solution (3.5 mL) was added and the mixture was heated to reflux for 16 h. The mixture was allowed to cool to rt and Boc-anhydride (3.24 g, 14.9 mmol) was added. The mixture was stirred for 24 h at rt, the solvent was evaporated, and the residue was partitioned between water and ethyl acetate. The organic phase was separated, dried over sodium sulfate, filtered, and evaporated. The residue was used without further purification.

3-[4-(2-Dimethylaminoethylcarbamoyl)-xanthen-9-ylidene]-8-azabicyclo[3.2.1]octane-8-carboxylic acid tert-butyl ester, 2m Using an adaptation of the method described in Procedure 25, substituting 3-(4-carboxyxanthen-9-ylidene)-8-azabicyclo[3.2.1]octane-8-carboxylic acid tert-butyl ester 1m for 9-oxo-9H-xanthene-4-carboxylic acid 5j and N,N-dimethylaminoethylamine for ammonium hydroxide, the title compound 2m was obtained.

Procedure 33

9-(8-Azabicyclo[3.2.1]oct-3-ylidene)-9H-xanthene-4-carboxylic acid (2-dimethylaminoethyl)-amide, Cpd 15

Compound 2m was treated with a 95:5 mixture of trifluoroacetic acid:water at rt, and the mixture was lyophilized, yielding the title compound 15 as a TFA salt.

9-(8-Azabicyclo[3.2.1]oct-3-ylidene)-9H-xanthene-4-carboxylic acid phenethyl-amide, Cpd 14

Using an adaptation of the method described in Procedures 25 and 33, substituting 3-(4-carboxyxanthen-9-ylidene)-8-azabicyclo[3.2.1]octane-8-carboxylic acid tert-butyl ester 2m for 9-oxo-9H-xanthene-4-carboxylic acid 5j and 2-phenethylamine for ammonium hydroxide in Procedure 25, the title compound 14 was obtained.

9-(8-Azabicyclo[3.2.1]oct-3-ylidene)-9H-xanthene-4-carboxylic acid dimethylamide, Cpd 11

Using an adaptation of the method described in Procedures 25 and 33, substituting 3-(4-carboxyxanthen-9-ylidene)-8-azabicyclo[3.2.1]octane-8-carboxylic acid tert-butyl ester 2m for 9-oxo-9H-xanthene-4-carboxylic acid 5j and dimethylamine for ammonium hydroxide in Procedure 25, the title compound 11 was obtained.

9-(8-Azabicyclo[3.2.1]oct-3-ylidene)-9H-xanthene-4-carboxylic acid benzylamide, Cpd 13

Using an adaptation of the method described in Procedures 25 and 33, substituting 3-(4-carboxyxanthen-9-ylidene)-8-azabicyclo[3.2.1]octane-8-carboxylic acid tert-butyl ester 2m for 9-oxo-9H-xanthene-4-carboxylic acid 5j and benzylamine for ammonium hydroxide in Procedure 25, the title compound 13 was obtained.

9-(8-Azabicyclo[3.2.1]oct-3-ylidene)-9H-xanthene-4-carboxylic acid methylamide, Cpd 10

Using an adaptation of the method described in Procedures 25 and 33, substituting 3-(4-carboxyxanthen-9-ylidene)-8-azabicyclo[3.2.1]octane-8-carboxylic acid tert-butyl ester 2m for 9-oxo-9H-xanthene-4-carboxylic acid 5j and methylamine for ammonium hydroxide in Procedure 25, the title compound 10 was obtained.

9-(8-Azabicyclo[3.2.1]oct-3-ylidene)-9H-xanthene-4-carboxylic acid phenylamide, Cpd 12

Using an adaptation of the method described in Procedures 25 and 33, substituting 3-(4-carboxyxanthen-9-ylidene)-8-azabicyclo[3.2.1]octane-8-carboxylic acid tert-butyl ester 2m for 9-oxo-9H-xanthene-4-carboxylic acid 5j and aniline for ammonium hydroxide in Procedure 25, the title compound 12 was obtained.

Enant (A)-9-(8-Azabicyclo[3.2.1]oct-3-ylidene)-9H-xanthene-4-carboxylic acid phenylamide, Cpd 47 and

Enant (B)-9-(8-Azabicyclo[3.2.1]oct-3-ylidene)-9H-xanthene-4-carboxylic acid phenylamide, Cpd 48

The (+) and (−) enantiomers of compound 12 (Cpds 47 and 48), in Table 1 herein were separated based on the following analytical chiral separation conditions: 25 cm ADH column, eluent: 1:1 acetonitrile:ethanol mixture containing 0.05% triethylamine. Cpd 47 is the first eluting isomer, and Cpd 48 is the second eluting isomer. Cpd 47: (+) ellipticity @ 246 nm; Cpd 48: (−) ellipticity @ 246 nm.

Example N

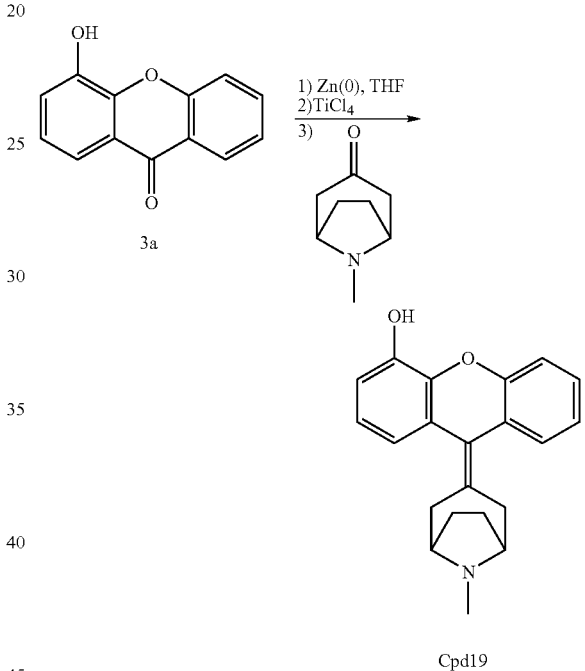

9-(8-Methyl-8-azabicyclo[3.2.1]oct-3-ylidene)-9H-xanthen-4-ol, Cpd 19

Using an adaptation of the method described in Procedure 4, substituting tropinone for N-trifluoroacetyl-nortropinone, the title compound 19 was obtained.

9-Piperidin-4-ylidene-9H-xanthen-4-ol, Cpd 16

Using an adaptation of the method described in Procedure 4, substituting N-Boc-tropinone for N-trifluoroacetyl-nortropinone, the title compound 16 was obtained.

9-(9-Methyl-9-azabicyclo[3.3.1]non-3-ylidene)-9H-xanthen-4-ol, Cpd 17

Using an adaptation of the method described in Procedure 4, substituting 9-methyl-9-azabicyclo[3.3.1]nonan-3-one for N-trifluoroacetyl-nortropinone, the title compound 17 was obtained.

9-(1-Methyl-piperidin-4-ylidene)-9H-xanthen-4-ol, Cpd 18

Using an adaptation of the method described in Procedure 4, substituting 1-methyl-piperidin-4-one for N-trifluoroacetyl-nortropinone, the title compound 18 was obtained.

9-(9-Azabicyclo[3.3.1]non-3-ylidene)-9H-xanthen-4-ol, Cpd 20

Using an adaptation of the method described in Procedure 4, substituting 9-azabicyclo[3.3.1]nonan-3-one for N-trifluoroacetyl-nortropinone, the title compound 20 was obtained.

Enant (A): 2,2,2-Trifluoro-1-[3-(4-hydroxy-xanthen-9-ylidene)-8-azabicyclo[3.2.1]oct-8-yl]-ethanone, Cpd 5 and

Enant (B): 2,2,2-Trifluoro-1-[3-(4-hydroxy-xanthen-9-ylidene)-8-azabicyclo[3.2.1]oct-8-yl]-ethanone, Cpd 6

The (+) and (−) enantiomers of 2,2,2-trifluoro-1-[3-(4-hydroxyxanthen-9-ylidene)-8-azabicyclo[3.2.1]oct-8-yl]-ethanone 4a (Cpds 5 and 6), in Table 1 herein were separated on a preparative chiralpak AD column (500 grams of 20 micron material, 5×41 cm) using hexane/methanol/ethanol (50/25/25) as eluent. The analytes were monitored using a wavelength of 220 nm. For analytical work, the same column material was used (chiralpak AD, 4.6×50 mm), and the same solvents, but in 80/10/10 proportion.

Enant (A): 9-(8-Azabicyclo[3.2.1]oct-3-ylidene)-9H-xanthen-4-ol, Cpd 8

Using an adaptation of the method described in Procedure 5, substituting enant (A), compound 5, for racemic 2,2,2-trifluoro-1-[3-(4-hydroxy-xanthen-9-ylidene)-8-azabicyclo[3.2.1 ]oct-8-yl]-ethanone, the title compound 8 was obtained.

Enant (B): 9-(8-Azabicyclo[3.2.1]oct-3-ylidene)-9H-xanthen-4-ol, Cpd 9

Using an adaptation of the method described in Procedure 5, substituting enant (B), compound 6, for racemic 2,2,2-trifluoro-1-[3-(4-hydroxy-xanthen-9-ylidene)-8-azabicyclo[3.2.1]oct-8-yl]-ethanone, the title compound 9 was obtained.

Enant (A)-9-(8-Benzyl-8-azabicyclo[3.2.1]oct-3-ylidene)-9H-xanthen-4-ol, Cpd 45 and

Enant (B)-9-(8-Benzyl-8-azabicyclo[3.2.1]oct-3-ylidene)-9H-xanthen-4-ol, Cpd 46

The (+) and (−) enantiomers of 9-(8-benzyl-8-azabicyclo[3.2.1]oct-3-ylidene)-9H-xanthen-4-ol 32 (Cpds 45 and 46), in Table 1 herein were separated based on the following analytical chiral separation conditions: 25 cm ADH column, eluent: ethanol containing 0.05% triethylamine. Cpd 45 is the first eluting isomer, and Cpd 46 is the second eluting isomer.

Enant (A)-9-(8-Pyridin-3-ylmethyl-8-azabicyclo[3.2.1]oct-3-ylidene)-9H-xanthen-4-ol, Cpd 49 and

Enant (B)-9-(8-Pyridin-3-ylmethyl-8-azabicyclo[3.2.1]oct-3-ylidene)-9H-xanthen-4-ol, Cpd 50

The (+) and (−) enantiomers of 9-(8-pyridin-3-ylmethyl-8-azabicyclo[3.2.1]oct-3-ylidene)-9H-xanthen-4-ol 31 (Cpds 49 and 50), in Table 1 herein were separated based on the following analytical chiral separation conditions: 15 cm ASH column, eluent: ethanol containing 0.05% triethylamine. Cpd 49 is the first eluting isomer, and Cpd 50 is the second eluting isomer. Cpd 49: (−) ellipticity @ 284 nm; Cpd 50: (+) ellipticity @ 284 nm.

Enant (A)-9-(8-Methyl-8-azabicyclo[3.2.1]oct-3-ylidene)-9H-xanthen-4-ol, Cpd 51 and

Enant (B)-9-(8-Methyl-8-azabicyclo[3.2.1]oct-3-ylidene)-9H-xanthen-4-ol, Cpd 52

The (+) and (−) enantiomers of 9-(8-methyl-8-azabicyclo[3.2.1]oct-3-ylidene)-9H-xanthen-4-ol 19 (Cpds 51 and 52), in Table 1 herein were separated based on the following analytical chiral separation conditions: 25 cm ADH column, eluent: ethanol containing 0.05% triethylamine. Cpd 51 is the first eluting isomer, and Cpd 52 is the second eluting isomer. Cpd 51: (+) ellipticity @ 284 nm; Cpd 52: (−) ellipticity @ 284 nm.

Enant (A)-9-(8-Furan-3-ylmethyl-8-azabicyclo[3.2.1]oct-3-ylidene)-9H-xanthen-4-ol, Cpd 58 and

Enant (B)-9-(8-Furan-3-ylmethyl-8-azabicyclo[3.2.1]oct-3-ylidene)-9H-xanthen-4-ol, Cpd 57

The (+) and (−) enantiomers of 9-(8-furan-3-ylmethyl-8-azabicyclo[3.2.1]oct-3-ylidene)-9H-xanthen-4-ol 25 (Cpds 57 and 58), in Table 1 herein were separated based on the following analytical chiral separation conditions: 25 cm ADH column, eluent: ethanol containing 0.05% triethylamine. Cpd 57 is the first eluting isomer, and Cpd 58 is the second eluting isomer. Cpd 57: (+) ellipticity @ 284 nm: Cpd 58: (−) ellipticity @ 284 nm.

Enant (A)-9-(8-Pyridin-2-ylmethyl-8-azabicyclo[3.2.1]oct-3-ylidene)-9H-xanthen-4-ol, Cpd 59 and

Enant (B)-9-(8-Pyridin-2-ylmethyl-8-azabicyclo[3.2.1]oct-3-ylidene)-9H-xanthen-4-ol, Cpd 60

The (+) and (−) enantiomers of 9-(8-pyridin-2-ylmethyl-8-azabicyclo[3.2.1]oct-3-ylidene)-9H-xanthen-4-ol 21 (Cpds 59 and 60), in Table xxx herein were separated based on the following analytical chiral separation conditions: 15 cm ADH column, eluent: isopropanol containing 0.05% triethylamine. Cpd 59 is the first eluting isomer, and Cpd 60 is the second eluting isomer. Cpd 59: (−) ellipticity @ 284 nm; Cpd 60: (+) ellipticity @ 284 nm.

Example P

Enant (A)-9-(8-Azabicyclo[3.2.1]oct-3-ylidene)-9H-xanthene-4-carboxylic acid phenethylamide, Cpd 55 and

Enant (B)-9-(8-Azabicyclo[3.2.1]oct-3-ylidene)-9H-xanthene-4-carboxylic acid phenethylamide, Cpd 56

The (+) and (−) enantiomers of compound 14 (Cpds 55 and 56), in Table 1 herein were separated based on the following analytical chiral separation conditions: 15 cm ASH column, eluent: methanol containing 0.05% triethylamine. Cpd 55 is the first eluting isomer, and Cpd 56 is the second eluting isomer. Cpd 55: (+) ellipticity @ 263 nm; Cpd 56: (−) ellipticity @ 263 nm.

Enant (A)-9-(8-Azabicyclo[3.2.1]oct-3-ylidene)-9H-xanthene-4-carboxylic acid benzylamide, Cpd 53 and

Enant (B)-9-(8-Azabicyclo[3.2.1]oct-3-ylidene)-9H-xanthene-4-carboxylic acid benzylamide, Cpd 54

The (+) and (−) enantiomers of compound 13 (Cpds 53 and 54), in Table 1 herein were separated based on the following analytical chiral separation conditions: 15 cm ASH column, eluent: methanol containing 0.05% triethylamine. Cpd 53 is the first eluting isomer, and Cpd 54 is the second eluting isomer. Cpd 53: (+) ellipticity @ 258 nm; Cpd 54: (−) ellipticity @ 258 nm.

Example Q

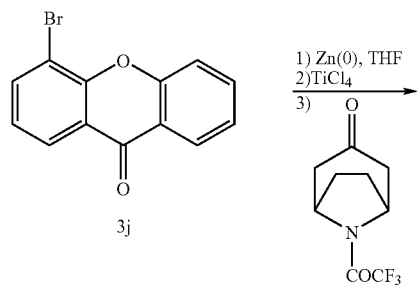

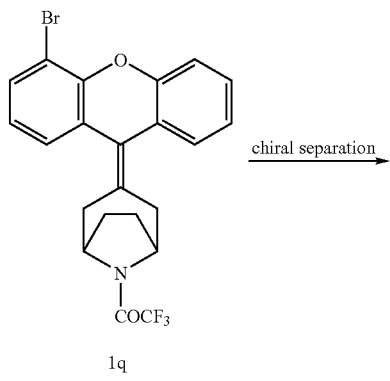

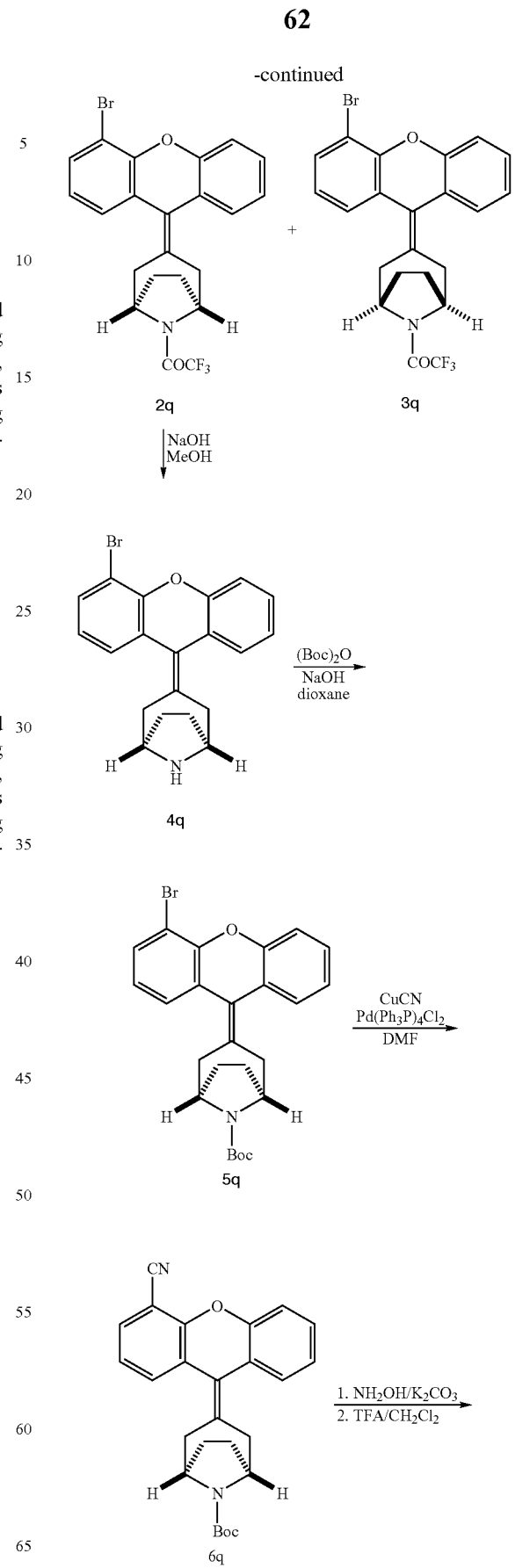

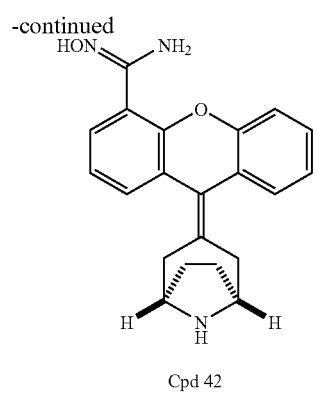

Cpd 42

1-[3-(4-Bromoxanthen-9-ylidene)-8-azabicyclo[3.2.1]oct-8-yl]-2,2,2-trifluoro-ethanone, 1q Using an adaptation of the method described in Procedure 4, substituting 4-bromoxanthen-9-one 3j for 4-hydroxy-xanthen-9-one 3a, the title compound 1q was obtained.

Enant (A)-1-[3-(4-Bromoxanthen-9-ylidene)-8-azabicyclo[3.2.1]oct-8-yl]-2,2,2-trifluoro-ethanone, 2q and

Enant (B)-1-[3-(4-Bromoxanthen-9-ylidene)-8-azabicyclo[3.2.1]oct-8-yl]-2,2,2-trifluoro-ethanone, 3q The (+) and (−) enantiomers of compound 1q (Cpds 2q and 3q) were separated on a preparative chiralpak AD column (500 grams of 20 micron material, 5×41 cm) using hexane/methanol/ethanol (50/25/25) as eluent. The analytes were monitored using a wavelength of 220 nm. For analytical work, the same column material was used (chiralpak AD, 4.6×50 mm), and the same solvents, but in 80/10/10 proportion.

Enant (A)-3-(4-Bromo-xanthen-9-ylidene)-8-azabicyclo[3.2.1]octane, 4q

Using an adaptation of the method described in Procedure 5, substituting enant (A)-1-[3-(4-bromoxanthen-9-ylidene)-8-azabicyclo[3.2.1]oct-8-yl]-2,2,2-trifluoro-ethanone 2q for 2,2,2-trifluoro-1-[3-(4-hydroxyxanthen-9-ylidene)-8-azabicyclo[3.2.1]oct-8-yl]-ethanone 4a, a 3N sodium hydroxide solution for potassium carbonate, and applying reflux temperatures in stead of rt, the title compound 4q was obtained.

Enant (A)-3-(4-Bromo-xanthen-9-ylidene)-8-azabicyclo[3.2.1]octane-8-carboxylic acid tert-butyl ester, 5q Using an adaptation of the method described in Procedure 32, substituting enant (A)-3-(4-bromo-xanthen-9-ylidene)-8-aza-bicyclo[3.2.1]octane 4q for Cpd 7, the title compound 5q was obtained.

Procedure 34

Enant (A)-3-(4-Cyano-xanthen-9-ylidene)-8-azabicyclo[3.2.1]octane-8-carboxylic acid tert-butyl ester, 6q To a solution of enant (A)-3-(4-bromo-xanthen-9-ylidene)-8-aza-bicyclo[3.2.1]octane-8-carboxylic acid tert-butyl ester 5q (3 g, 6.6 mmol) in dimethyl formamide (90 mL) were added copper cyanide (3 g, 33 mmol) and palladium tetrakis triphenylphosphine dichloride (45 mg, 0.66 mmol). The mixture was heated to 140° C. for 16 h. The mixture was allowed to cool to rt and water was added. The mixture was extracted with methylene chloride. The organic layer was separated, dried, filtered, and evaporated. The residue was purified via flash column chromatography to yield title compound 6q.

Procedure 35

Enant (A)-9-(8-Aza-bicyclo[3.2.1]oct-3-ylidene)-N-hydroxy-9H-xanthene-4-carboxamidine, Cpd 42

To a solution of enant (A)-3-(4-cyano-xanthen-9-ylidene)-8-aza-bicyclo[3.2.1]octane-8-carboxylic acid tert-butyl ester 6q (0.3 g, 0.72 mmol) in ethanol (8 mL) were added hydroxylamine hydrochloride (0.15 g, 2.2 mmol) and potassium carbonate (0.2 g, 1.4 mmol). The mixture was heated to reflux for 16 h. The mixture was allowed to cool to rt and the solids were removed via filtration, The filtrate was evaporated and the residue was dissolved in methylene chloride containing 10% trifluoroacetic acid. The mixture was stirred for 1 h at rt and evaporated. The residue was purifiede via reverse phase HPLC, yielding 128 mg (58%) of title compound 42 as a TFA salt; (+) ellipticity @ 269 nm.

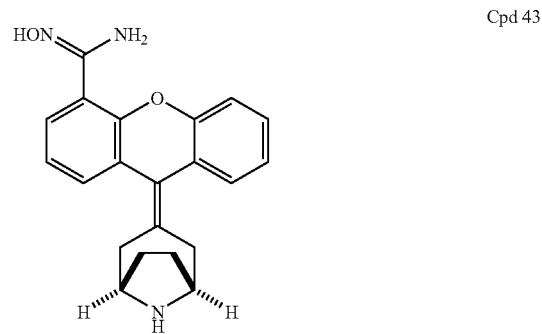

Cpd 43

Enant (B)-9-(8-Aza-bicyclo[3.2.1]oct-3-ylidene)-N-hydroxy-9H-xanthene-4-carboxamidine, Cpd 43

Using an adaptation of the method described in Procedures 5, 22 and 24, substituting Cpd 3q for 2,2,2-trifluoro-1-[3-(4-hydroxyxanthen-9-ylidene)-8-azabicyclo[3.2.1]oct-8-yl]-ethanone 4a, a 3N sodium hydroxide solution for potassium carbonate, and applying reflux temperatures in stead of rt, in Procedure 5, the title compound 43 was obtained as a TFA salt; (−) ellipticity @ 269 nm.

Example R

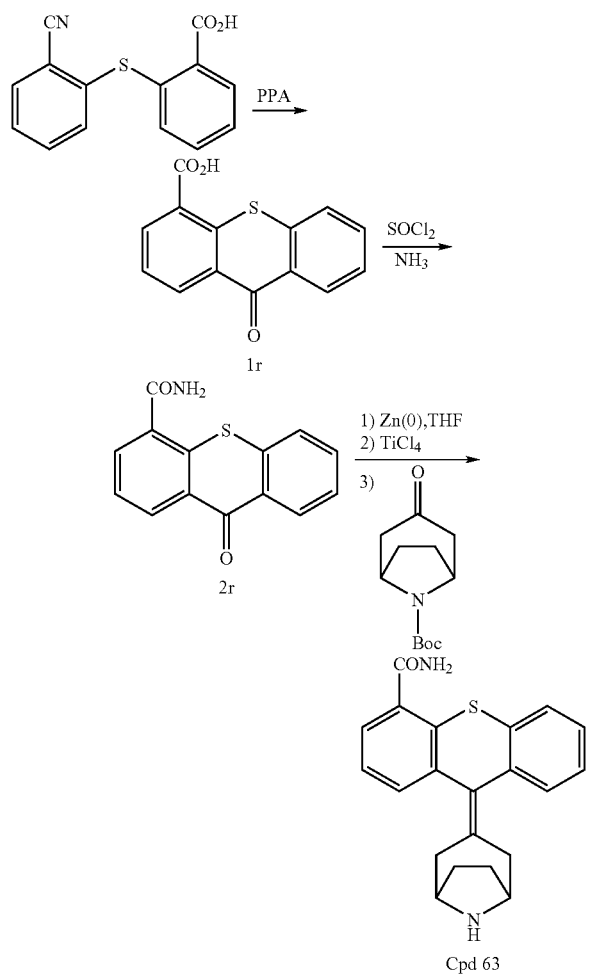

9-Oxo-9H-thioxanthene-4-carboxylic acid, 1r

A sample of 2-(2-cyanophenylsulfanyl)-benzoic acid (15 g, 58.8 mmol) was heated in polyphosphoric acid (300 g) at 170° C. for 16 h. The mixture was allowed to cool to rt and poured onto ice. The precipitate was collected via filtration, yielding 15 g (quant.) of title compound 1r. The material was used without further purification.

9-Oxo-9H-thioxanthene-4-carboxylic acid amide, 2r

A sample of 9-oxo-9H-thioxanthene-4-carboxylic acid 1r (15 g, 58.7 mmol) was heated in sulfonyl chloride (70 mL) for 2 h. Excess sulfonyl chloride was removed via evaporation. The residue was dissolved in tetrahydrofuran (200 mL), and triethylamine (16.4 mL, 117.4 mmol) and a 0.5 M solution of ammonia in dioxane (176 mL, 88.5 mmol) were added. Methanol (20 mL) was added, and the mixture was evaporated. Water and chloroform were added, and a precipitate formed. The precipitate was isolated via filtration, and yielded 3.5 g (25%) of title compound 2r. The organic layer was separated, dried, filtered, and evaporated to yield 11 g of recovered 1r.

9-(8-Azabicyclo[3.2.1]oct-3-ylidene)-9H-thioxanthene-4-carboxylic acid amide, Cpd 63

Using an adaptation of the method described in Procedure 4, substituting 9-oxo-9H-thioxanthene-4-carboxylic acid amide 2r for 4-hydroxy-xanthen-9-one 3a and N-Boc-nortropinone for N-trifluoroacetyl-nortropinone, the title compound 63 was obtained.

Compounds 1 through 64 of Formula (I), in Table 1 were prepared according to the methods described by the Schemes and Examples, herein.

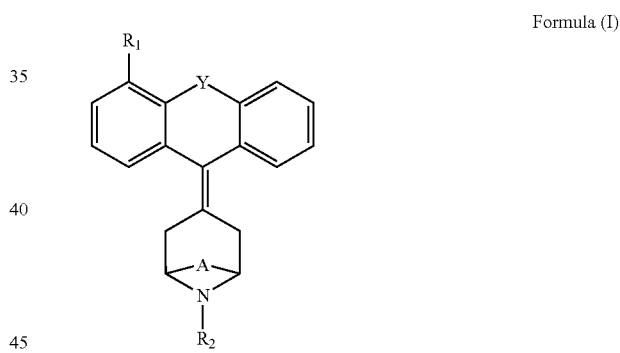

Formula (I)

TABLE 1

Structural and Mass Spectral Data

| Cpd No. | $R_1$ | A | $R_2$ | Y | MS Parent Peak Obs'd | MS Calc'd |
|---|---|---|---|---|---|---|
| 1 | methoxy | —$(CH_2)_2$— | H | O | 320.0 | 319.4 |
| 2 | hydroxy | —$(CH_2)_2$— | H | O | 306.1 | 305.4 |
| 3 | aminocarbonyl | —$(CH_2)_2$— | H | O | 333.2 | 332.4 |
| 4 | aminocarbonyl | —$(CH_2)_2$— | furan-2-yl methyl | O | 413.2 | 412.5 |
| 5- Enant. A | hydroxy | —$(CH_2)_2$— | trifluoromethyl carbonyl | O | 402.0 | 401.4 |
| 6- Enant. B | hydroxy | —$(CH_2)_2$— | trifluoromethyl carbonyl | O | 401.9 | 401.4 |
| 7 | methoxy carbonyl | —$(CH_2)_2$— | trifluoromethyl carbonyl | O | 444.1 | 443.4 |
| 8- | hydroxy | —$(CH_2)_2$— | H | O | 306.0 | 305.4 |

TABLE 1-continued

Structural and Mass Spectral Data

| Cpd No. | R₁ | A | R₂ | Y | MS Parent Peak Obs'd | MS Calc'd |
|---|---|---|---|---|---|---|
| 9- Enant. A | hydroxy | —(CH₂)₂— | H | O | 306.0 | 305.4 |
| 10 Enant. B | methylaminocarbonyl | —(CH₂)₂— | H | O | 347.0 | 346.4 |
| 11 | dimethylaminocarbonyl | —(CH₂)₂— | H | O | 360.9 | 360.5 |
| 12 | phenylaminocarbonyl | —(CH₂)₂— | H | O | 408.9 | 408.5 |
| 13 | phenylmethylaminocarbonyl | —(CH₂)₂— | H | O | 422.9 | 422.5 |
| 14 | phenylethyl-aminocarbonyl | —(CH₂)₂— | H | O | 437.0 | 436.6 |
| 15 | (2-dimethyl amino-ethyl) aminocarbonyl | —(CH₂)₂— | H | O | 404.18 | 403.5 |
| 16 | hydroxy | absent | H | O | 280.1 | 279.3 |
| 17 | hydroxy | —(CH₂)₃— | methyl | O | 334.2 | 333.4 |
| 18 | hydroxy | absent | methyl | O | 294.1 | 293.4 |
| 19 | hydroxy | —(CH₂)₂— | methyl | O | 320.1 | 319.4 |
| 20 | hydroxy | —(CH₂)₃— | H | O | 320.1 | 319.4 |
| 21 | hydroxy | —(CH₂)₂— | pyridin-2-yl methyl | O | 397.2 | 396.5 |
| 22 | hydroxy | —(CH₂)₂— | pyridin-4-yl methyl | O | 397.2 | 396.5 |
| 23 | hydroxy | —(CH₂)₂— | 2-hydroxy-pyridin-4-yl methyl | O | 413.2 | 412.5 |
| 24 | hydroxy | —(CH₂)₂— | thien-2-yl methyl | O | 402.1 | 401.5 |
| 25 | hydroxy | —(CH₂)₂— | furan-3-yl methyl | O | 386.2 | 385.5 |
| 26 | hydroxy | —(CH₂)₂— | cyclopropyl methyl | O | 360.2 | 359.5 |
| 27 | hydroxy | —(CH₂)₂— | 2-methyl-but-2-enyl | O | 374.2 | 373.5 |
| 28 | hydroxy | —(CH₂)₂— | 2-phenyl-imidazol-4-yl methyl | O | 462.2 | 461.6 |
| 29 | aminocarbonyl | —(CH₂)₂— | trifluoromethyl carbonyl | O | 429.1 | 428.41 |
| 30 | hydroxy | —(CH₂)₂— | phenethyl | O | 410.2 | 409.53 |
| 31 | hydroxy | —(CH₂)₂— | pyridin-2-ylmethyl | O | 397.2 | 396.49 |
| 32 | hydroxy | —(CH₂)₂— | phenylmethyl | O | 396.2 | 395.50 |
| 33 | hydroxy | —(CH₂)₂— | benzothien-3-ylmethyl | O | 452.2 | 451.59 |
| 34 | hydroxy | —(CH₂)₂— | 1H-imidazol-2-ylmethyl | O | 386.2 | 385.47 |
| 35 | hydroxy | —(CH₂)₂— | isoquinolin-5-ylmethyl | O | 447.2 | 446.55 |
| 36 | aminocarbonyl | —(CH₂)₂— | trifluoromethyl carbonyl | O | 429.2 | 428.41 |
| 37 | aminocarbonyl | —(CH₂)₂— | H | O | 333.2 | 332.40 |
| 38 | aminocarbonyl | —(CH₂)₂— | trifluoromethtyl carbonyl | O | 429.2 | 428.41 |
| 39 | aminocarbonyl | —(CH₂)₂— | H | O | 333.2 | 332.40 |
| 40 | aminocarbonyl | —(CH₂)₂— | trifluoromethyl carbonyl | S |  | 444.47 |
| 41 | amino | —(CH₂)₂— | H | O | 305.2 | 304.39 |
| 42 | hydroxyamidino | —(CH₂)₂— | H | O | 348.2 | 347.42 |
| 43 Enant. A | hydroxyamidino | —(CH₂)₂— | H | O | 348.2 | 347.42 |
| 44 Enant. B | formylamino | —(CH₂)₂— | H | O | 333.2 | 332.40 |
| 45 | hydroxy | —(CH₂)₂— | phenylmethyl | O | 396.1 | 395.50 |
| 46 | phenylaminocarbonyl | —(CH₂)₂— | H | O | 396.1 | 395.50 |
| 47 | phenylaminocarbonyl | —(CH₂)₂— | H | O | 409.2 | 408.50 |
| 48 | hydroxy | —(CH₂)₂— | pyridin-3-ylmethyl | O | 409.2 | 408.50 |
| 49 | hydroxy | —(CH₂)₂— | pyridin-3-ylmethyl | O | 397.2 | 396.49 |
| 50 | hydroxy | —(CH₂)₂— | methyl | O | 397.2 | 396.49 |
| 51 | hydroxy | —(CH₂)₂— | methyl | O | 320.2 | 319.40 |

TABLE 1-continued

Structural and Mass Spectral Data

| Cpd No. | $R_1$ | A | $R_2$ | Y | MS Parent Peak Obs'd | MS Calc'd |
|---|---|---|---|---|---|---|
| 52 | pyridin-2-yloxy | —$(CH_2)_2$— | H | O | 320.2 | 319.40 |
| 53 | phenylmethylamioncarbonyl | —$(CH_2)_2$— | H | O | 423.2 | 422.53 |
| 54 | phenethyl aminocarbonyl | —$(CH_2)_2$— | H | O | 423.2 | 422.53 |
| 55 | phenethyl aminocarbonyl | —$(CH_2)_2$— | H | O | 437.2 | 436.55 |
| 56 | hydroxy | —$(CH_2)_2$— | furan-3-ylmethyl | O | 437.2 | 436.55 |
| 57 | hydroxy | —$(CH_2)_2$— | furan-3-ylmethyl | O | 386.1 | 385.46 |
| 58 | hydroxy | —$(CH_2)_2$— | pyridin-2-ylmethyl | O | 386.1 | 385.46 |
| 59 | hydroxy | —$(CH_2)_2$— | pyridin-2-ylmethyl | O | 397.2 | 396.49 |
| 60 | hydroxy | —$(CH_2)_2$— | pyridin-2-ylmethyl | O | 397.2 | 396.49 |
| 61 | 4-chloro-phenylamino | —$(CH_2)_2$— | H | O | 383.1 | 382.46 |
| 62 | pyridin-3-yl amino | —$(CH_2)_2$— | H | O | 415.2 | 414.94 |
| 63 | aminocarbonyl | —$(CH_2)_2$— | H | S | 382.3 | 381.48 |
| 64 | phenylamino | —$(CH_2)_2$— | H | O |  | 348.47 |

Biological Examples

Example 1

Rat Brain Delta Opioid Receptor Binding Assay

Procedure: Male, Wistar rats (150-250 g, VAF, Charles River, Kingston, N.Y) were killed by $CO_2$, and their brains removed and placed immediately in ice cole Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.15 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. Resultant data is shown in Table 1.

Example 2

Rat Brain Mu Opioid Receptor Binding Assay

Procedure: Male, Wistar rats (150-250 g, VAF, Charles River, Kingston, N.Y.) were killed by $CO_2$, and their brains removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity quantifed on a LKB (Wallac) 1205 BetaPlate liquid scintillation counter. Analysis: The data from the scintillation counter were used to calculate either the % inhibition compared to control binding (when only a single concentration of test compound was evaluated) or a $K_i$ value (when a range of concentrations tested). Percent inhibition was calculated as: [(total dpm-test compound dpm)/(total dpm-nonspecific dpm)]*100. Kd and Ki values were calculated using Graph-Pad PRISM data analysis program. Resultant data is shown in Table 1.

Example 3

Functional Assay: [$^{35}$S]GTPγS Binding Assay in NG108-15 Cell Membranes (delta opioid)

Methods: NG108-15 cell membranes were purchased from Applied Cell Sciences (Rockville, Md.). A sample (8 mg/mL) of membrane protein suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM MgCl$_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 µg/mL) were preincubated with SPA (10 mg/mL) at 25° C. for 45 min in the assay buffer. The SPA (5 mg/mL) coupled with membranes (37.5 µg/mL) was then incubated with 0.1 nM [$^{35}$S] GTPγS in the same Tris buffer containing 100 µM GDP in total volume of 200 µL. Increasing concentrations of receptor agonists were used to stimulate [$^{35}$S]-GTPγS binding. The basal binding was tested in the absence of agonists and non-specific binding was tested in the presence of 10 µM unlabeled GTPγS. The data were analyzed on a Packard Top Count.

DATA

% of Basal=(stimulated−non specific)*100/(basal−non specific).

EC$_{50}$ values were calculated using GraphPad Prism. Resultant data is shown in Table 1.

Example 4

Functional Assay: [$^{35}$S]GTPγS Binding Assays in CHO-hMOR Cell Membranes

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension kept on ice. A 1 mL volume of membranes was added to 15 mL cold binding assay buffer containing 50 mM HEPES, pH 7.6, 5 mM MgCl$_2$, 100 mM NaCl, 1 mM DTT and 1 mM EDTA. The membrane suspension was homogenized with a Polytron and centrifuged at 3,000 rpm for 10 min. The supernatant was then centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 µg/mL) were then incubated with 0.5 nM [$^{35}$S] GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [$^{35}$S]GTPγS binding. Both basal and non-specific binding was tested in the absence of agonist; non-specific binding determination included 10 µM unlabeled GTPγS.

Compounds were tested for function as antagonists by evaluating their potential to inhibit agonist-stimulated GTPγS binding. Radioactivity was quantified on a Packard Top-Count. The following parameters were calculated:

$$\% \text{ stimulation} = \frac{(\text{test compound } cpm - \text{non-specific } cpm)}{(\text{basal } cpm - \text{non-specific } cpm)} \times 100.$$

$$\% \text{ inhibition} = \frac{(\% \text{ stimulation by } 1 \, \mu M \, DAMGO - \% \text{ stimulation by test compound})}{(\% \text{ stimulation by } 1 \, \mu M \, DAMGO - 100)} \times 100$$

EC$_{50}$ values were calculated using GraphPad Prism. Resultant data is shown in Table 1.

TABLE 1

Biological Data

| | Binding Data | | Functional Data | |
|---|---|---|---|---|
| Cpd No. | rDOR (Ki, nM) | rMOR (Ki, nM) | delta GTPγS binding EC50 (nM)/Rel Eff | mu GTPγS binding EC50 (nM)/Rel Eff |
| 1* | 3802 | 1794 | — | — |
| 2 | 0.48 | 7.0 | 50.9 (0.67) | 382 (0.37) |
| 3 | 3.2 | 29.4 | 42.0 | 3964 |
| 4 | 2.3 | 2.5 | 9.40 | 4043 |
| 5 | 2112 | 5621 | | |
| 6 | 8496 | >10000 | | |
| 7 | >10000 | >10000 | | |
| 8 | 0.56 | 3.5 | 9.98 | 902 |
| 9 | 68.2 | 63.6 | | |
| 10 | 1573, 136 | 27, 51.0 | 617 | >10,000 |
| 11 | 3109 | 471 | | |
| 12 | 272, 67.9 | 32 | 30.3 (1.03) | 611 (0.96) |
| 13 | 216, 17.8 | 15, 12.7 | 5.68 (0.87) | 717 (0.67) |
| 14 | 864, 58.3 | 44, 36.2 | 10.4 (0.92) | 997 (0.54) |
| 15 | 1420 | 336 | | |
| 16 | 15.1 | 776 | 964 | |
| 17 | 132 | 221 | | |
| 18 | 330 | 4612 | | |
| 19 | 28.3 | 372 | 768 | >10,000 |
| 20 | 20.2 | 32.6 | 180 | 7080 |
| 21 | 0.007 | 0.10 | 21.8 | >10,000 |
| 22 | 0.97 | 358 | 2716 | >10,000 |
| 23 | 1.50 | 2.18 | 52.8 | 12365 |
| 24 | 0.046 | 1.58 | 6.05 | >10,000 |
| 25 | 0.26 | 0.56 | 1.08 | 2815 |
| 26 | 5.43 | 65.9 | 194 | >10,000 |
| 27 | 0.35 | 2.03 | 9.80 | >10,000 |
| 28 | 192 | 58.5 | 1378 | >10,000 |
| 30 | 63.5 | 27.7 | 2964 | >10,000 |
| 31 | 0.028 | 1.23 | 134 | 8090 |
| 32 | 0.023 | 0.29 | 28.6 | >10,000 |
| 33 | 137 | 168 | | |
| 34 | 0.028 | 0.53 | 3.33 | 1610 |
| 35 | 180 | 286 | | |
| 36 | 1793 | >10,000 | | |
| 37 | 4.00 | 29.0 | 156 | 878 |
| 38 | 6440 | >10,000 | | |
| 39 | 31.9 | 96.4 | 1243 | |

TABLE 1-continued

Biological Data

| Cpd No. | Binding Data | | Functional Data | |
|---|---|---|---|---|
| | rDOR (Ki, nM) | rMOR (Ki, nM) | delta GTPγS binding EC50 (nM)/Rel Eff | mu GTPγS binding EC50 (nM)/Rel Eff |
| 42 | 237 | 56.5 | | |
| 43 | >10,000 | >10,000 | | |
| 44 | 19.2 | 45.2 | 7.03 | |
| 45 | 9.62 | 11.37 | 1419.8 | |
| 46 | 0.03 | 0.19 | 10.2 | |
| 47 | 250.45 | 292.95 | | |
| 48 | 3.71 | 3.58 | 101.1 | |
| 49 | 62.61 | 443.20 | | |
| 50 | 0.08 | 0.68 | 217.9 | |
| 51 | 11.2 | 138.1 | 59.2 | |
| 52 | 323.4 | 1323 | | |
| 53 | 1128 | 2027 | | |
| 55 | 100.4 | 200 | | |
| 56 | 49.6 | 6.96 | 40.1 | |
| 57 | 246 | 36.5 | | |
| 58 | 0.1 | 0.45 | 2.6 | |
| 59 | 0.07 | 0.39 | | |
| 60 | 0.01 | 0.01 | | |
| 61 | 395 | 3156 | | |
| 62 | 107.5 | 158.8 | | |
| 63 | 0.71 | 3.31 | 2.7 | |
| 64 | 862 | 2419 | | |

*a prodrug form
rDOR Ki: Rat delta opioid receptor binding constant
rMOR Ki: Rat mu opioid receptor binding constant Example 5

Rat CFA Radiant Heat Model of Inflammatory Pain

Intraplantar injection of Complete Freund's Adjuvant (CFA) in rodents results in a strong, long-lasting inflammatory reaction, characterized by a chronic and pronounced hyperalgesia to both thermal and mechanical stimuli. These effects peak between 24-72 h following injection, and can last for several days to few few weeks. To assess the ability of compounds to reverse thermal hyperalgesia, male Sprague-Dawley rats (200-350 g) are given an intraplantar injection of CFA (1:1 CFA:saline, 100 µL) into their left hindpaw. Following a 24-h incubation period, response latencies on the Radiant Heat Paw Stimulator (RH) are obtained and compared to baseline (pre-CFA) latencies. The RH device automatically registers lifting of the paw from the surface of the glass. Only rats that exhibit at least a 25% reduction in response latency from baseline (i.e. hyperalgesia) are included in further analysis. Following the post CFA latency assessment, rats are dosed orally (2.5 mL/kg) with test compound or vehicle (hydroxypropylmethylcellulose, HPMC). Percent reversal of hyperalgesia is calculated for each animal as (Treatment Response−postCFA Response)/(preCFA Response−postCFA Response)×100. Therefore, a return to normal pre-CFA thresholds is defined as 100% efficacy, whereas no change from post-CFA thresholds is 0% efficacy. Average % reversal of hyperalgesia is then calculated for each treatment group (n=6-8 rats/group).

Example 6

The therapeutic effect of delta opioid agonists has been demonstrated in:

Pain (Fang, (1995) Shengli Kexue Jinzhan 26:137-40; Garzon, (1995) Analgesia (Elmsford, N.Y.) 1:131-44; Mafthes, Maldonado, Simonin, Valverde, Slowe, Kitchen, Befort, Dierich, Le Meur and et al., (1996) Nature (London) 383: 819-823; Stevens, (1996) Journal of Pharmacology and Experimental Therapeutics 276:440-8; Dondio, Ronzoni and Petrillo, (1997) Expert Opinion on Therapeutic Patents 7:1075-1098; Hutcheson, Sanchez-Blazquez, Rodriguez-Diaz, Garzon, Schmidhammer, Borsodi, Roques and Maldonado, (1999) European Journal of Pharmacology 383: 29-37; Fraser, Pradhan, Clarke and Wahlestedt, (2000) Journal of Pharmacology and Experimental Therapeutics 295:1135-1141; Scheideler, (2000) Current Opinion in Central & Peripheral Nervous System Investigational Drugs 2:171-177; Wei, Brown, Takasaki, Plobeck, Delorme, Zhou, Yang, Jones, Gawell, Gagnon, Schmidt, Yue, Walpole, Payza, St-Onge, Labarre, Godbout, Jakob, Butterworth, Kamassah, Morin, Projean, Ducharme and Roberts, (2000) Journal of Medicinal Chemistry 43:3895-3905; Nagase, Yajima, Fujii, Kawamura, Narita, Kamei and Suzuki, (2001) Life Sciences 68:2227-2231; Abeyta, Dettmer, Barnes, Vega, Carta, Gallegos, Raymond-Stintz, Savage, Valenzuela and Saland, (2002) Brain Research 931:100-5. FIELD Reference Number: FIELD Journal Code:0045503 FIELD Call Number:; Cahill, Morinville, Hoffert, O'Donnell and Beaudet, (2003) Pain 101:199-208; Collina, Azzolina, Vercesi, Brusotti, Rossi, Barbieri, Lanza, Mennuni, Alcaro, Battaglia, Linati and Ghislandi, (2003) Farmaco 58:939-946; Hurley, Banfor and Hammond, (2003) Neuroscience (Oxford, United Kingdom) 118.789-796).

Inflammatory Pain States (Stein, Millan, Shippenberg, Peter and Herz, (1989) Journal of Pharmacology and Experimental Therapeutics 248:1269-75; Antonijevic, Mousa, Schaefer and Stein, (1995) Journal of Neuroscience 15:165-72; Ballet, Mauborgne, Benoliel, Bourgoin, Hamon, Cesselin and Collin, (1998) Brain Research 796:198-208; Hurley and Hammond, (2001) Journal of Neuroscience 21:2536-2545; Przewlocki and Przewlocka, (2001) European Journal of Pharmacology 429:79-91; Spetea, Rydelius, Nylander, Ahmed, Bileviciute-Ljungar, Lundeberg, Svensson and Kreicbergs, (2002) European Journal of Pharmacology 435:245-252; Bao, Jin, Zhang, Wang, Xu, Zhang, Wang, Ning, Cai, Guan, Xiao, Xu, He, Hokfelt, Zhou and Zhang, (2003) Neuron 37:121-133; Cahill, Morinville, Hoffert, O'Donnell and Beaudet, (2003) Pain 101:199-208; Martin, Matifas, Maldonado and Kieffer Brigitte, (2003) European Journal of Neuroscience 17:701-8. FIELD Reference Number: FIELD Journal Code:8918110 FIELD Call Number:; Petrillo, Angelici, Bingham, Ficalora, Garnier, Zaratin, Petrone, Pozzi, Sbacchi, Stean, Upton, Dondio and Scheideler, (2003) Journal of Pharmacology and Experimental Therapeutics 307:1079-1089).

Visceral Pain
(Schmauss and Yaksh, (1984) Journal of Pharmacology and Experimental Therapeutics 228:1-12; Craft, henley, Haaseth, Hruby and Porreca, (1995) Journal of Pharmacology and Experimental Therapeutics 275:1535-42; Su, Wachtel and Gebhart, (1998) Journal of Neurophysiology 80:3112-3119; Gebhart, Su, Joshi, Ozaki and Sengupta, (1999) Progress in Pain Research and Management 14:225-235; Sora, Li, Funada, Kinsey and Uhl, (1999) European Journal of Pharmacology 366:R3-R5; Gebhart, (2000) Regional Anesthesia and Pain Medicine 25:632-638; Martin, Matifas, Maldonado and Kieffer Brigitte, (2003) European Journal of Neuroscience 17:701-8).

Lung
(Kuo, Rohde, Barnes and Rogers, (1992) British Journal of Pharmacology 105:361-6; Campa, Schreiber, Bepler, Bishop, McNutt, Chang and Patz, (1996) Cancer Research 56:1695-701; Bolli, Shinmura, Tang, Kodani, Xuan, Guo and Dawn, (2002) Cardiovascular Research 55:506-519; Janssens, Leenaerts, Fernandez-Gadea, Gomez-Sanchez, Flameng, Herijgers, Meert and Borgers, (2003) PCT Int. Appl. 75 pp.; McLeod, Tulshian and Hey, (2003) Expert Opinion on Therapeutic Patents 13:1501-1512).

Cardioprotection
(Schultz, Hsu, Nagase and Gross, (1998) American Journal of Physiology 274:H909-H914; Fryer, Hsu, Eells, Nagase and Gross, (1999) Circulation Research 84:846-851; Fryer, Hsu, Nagase and Gross, (2000) Journal of Pharmacology and Experimental Therapeutics 294:451-457; Fryer, Hsu and Gross, (2001) Basic Research in Cardiology 96:136-142; Fryer, Patel, Hsu and Gross, (2001) American Journal of Physiology 281:H1184-H1192; Fryer, Pratt, Hsu and Gross, (2001) Journal of Pharmacology and Experimental Therapeutics 296:642-649; Fryer, Wang, Hsu and Gross, (2001) American Journal of Physiology 280:H1346-H1353; Fryer, Wang, Hsu, Nagase and Gross, (2001) Journal of Pharmacology and Experimental Therapeutics 299:477-482; Huh, Gross, Nagase and Liang, (2001) American Journal of Physiology 280:H377-H383; Karck, Tanaka, Bolling, Simon, Su, Oeltgen and Haverich, (2001) Journal of Thoracic and Cardiovascular Surgery 122:986-992; McPherson and Yao, (2001) Anesthesiology 94:1082-1088; Patel, Hsu, Moore and Gross, (2001) Journal of Molecular and Cellular Cardiology 33:1455-1465; Rebrova, Maslov and Tam, (2001) Voprosy Meditsinskoi Khimii 47:338-345; Patel, Ludwig, Fryer, Hsu, Warltier and Gross, (2002) FASEB Journal 16:1468-1470, 10.1096/fj.02-0170fje; Sigg, Coles, Oeltgen and laizzo, (2002) American Journal of Physiology 282:H1953-H1960; Zhang, McPherson, Liu, Baman, McPherson, Rock and Yao, (2002) Journal of Pharmacology and Experimental Therapeutics 301:1012-1019; Patel, Hsu and Gross, (2004) Basic Research in Cardiology 99:38-45; Patel, Hsu and Gross, (2004) Life Sciences 75:129-140; Pear and Gross, (2004) Basic research in cardiology 99:29-37. FIELD Reference Number: FIELD Journal Code:0360342 FIELD Call Number; Shinmura, Nagai, Tamaki and Bolli, (2004) Basic research in cardiology 99:46-55.

Urinary Dysfunction
(Dray and Metsch, (1984) Neuroscience Letters 47:81-4; Dray, (1985) Journal of Pharmacological Methods 13:157-65; Craft, henley, Haaseth, Hruby and Porreca, (1995) Journal of Pharmacology and Experimental Therapeutics 275:1535-42; Murase, Hamada and Asaki, (1996) PCT Int. Appl. 93 pp.; Su, Sengupta and Gebhart, (1997) Journal of Neurophysiology 77:1566-1580; Sezen, Kenigs and Kapusta, (1998) Journal of Pharmacology and Experimental Therapeutics 287:238-245; Chang, Gengo, Biciunas, Ma, Pendergast and Jan, (2003) PCT Int. Appl 73 pp.; Igari, Yanai and Goya, (2004) PCT Int. Appl. 30 pp.).

Cough
(Kamei, Iwamoto, Suzuki, Nagase, Misawa and Kasuya, (1993) European Journal of Pharmacology 234:117-20; Kotzer, Hay, Dondio, Giardina, Petrillo and Underwood, (2000) Journal of Pharmacology and Experimental Therapeutics 292:803-9; McLeod, Tulshian and Hey, (2003) Expert Opinion on Therapeutic Patents 13:1501-1512).

Anxiety
(Roberts, Gold, Polis, McDonald, Filliol, Kieffer and Koob, (2001) Alcoholism: Clinical and Experimental Research 25:1249-1256; Gaveriaux-Ruff and Kieffer, (2002) Neuropeptides (Edinburgh, United Kingdom) 36:62-71; Masuda, Suzuki, Takemura, Sugawara, Guo, Liu, Kawarada, Shimizu and Sugiyama, (2003) Tohoku Journal of Experimental Medicine 201:23-27; Noble and Roques, (2003) Drugs of Today 39:897-908).

Depression
(Broom, Jutkiewicz, Folk, Traynor, Rice and Woods, (2002) Psychopharmacology (Berlin, Germany) 164:42-48; Broom, Jutkiewicz, Folk, Traynor, Rice and Woods, (2002) Neuropsychopharmacology 26:744-755; Broom, Jutkiewicz, Rice, Traynor and Woods, (2002) Japanese Journal of Pharmacology 90:1-6; Varona, Gil, Saracibar, Maza, Echevarria and Irazusta, (2003) Arzneimittel-Forschung 53.21-25).

Parkinsons Disease
(Barneoud, Descombris, Aubin and Abrous, (2000) European journal of neuroscience 12:322-36. Hill, Hille and Brotchie, (2000) Drug News & Perspectives 13:261-268; Hudzik, Howell, Payza and Cross, (2000) European Journal of Pharmacology 396:101-107; Hille, Fox, Maneuf, Crossman and Brotchie, (2001) Experimental Neurology 172:189-198).

Example 7

The therapeutic effect of mu opioid agonists has been demonstrated in:

Pain
(Pasternak, (1986) Advances in Pain Research and Therapy 8:337-44; Garzon and Sanchez-Blazques, (1995) Life Sciences 56:PL237-PL242; Matthes, Maldonado, Simonin, Valverde, Slowe, Kitchen, Befort, Dierich, Le Meur and et al., (1996) Nature (London) 383:819-823; Stevens, (1996) Journal of Pharmacology and Experimental Therapeutics 276:440-8; Dayer, Desmeules and Collart, (1997) Drugs 53:18-24; Valverde, Maldonado and Kieffer, (1998) CNS Drugs 10:1-10; Kharkevich and Churukanov, (1999) European Journal of Pharmacology 375:121-131; Pasternak, (2000) Progress in Pain Research and Management 16:147-162; Gutstein and Akil, J. G. Hardman and L. E. Limbird (2001) The pharmacological basis of therapeutics 569-619; Pasternak, (2001) Neuroscientist 7:220-231; Smith, Ross, Nielsen and Saini, (2001) European Journal of Pain (London, United Kingdom) 5:135-136; Wells, Bartlett, Ananthan and Bilsky, (2001) Journal of Pharmacology and Experimental Therapeutics 297:597-605; Abbadie and Pasternak, (2003) Handbook of Chemical Neuroanatomy 20:1-29; Collina, Azzolina, Vercesi, Brusotti, Rossi, Barbieri, Lanza, Mennuni, Alcaro, Battaglia, Linati and Ghislandi, (2003) Farmaco 58:939-946; Cowan, (2003) International Journal of Clinical Practice, Supplement 133:3-8; Hurley, Banfor and Hammond, (2003) Neuroscience (Oxford, United Kingdom) 118:789-796; Neilan, King, Rossi, Ansonoff, Pintar, Schiller and Pasternak, (2003) Brain Research 974:254-257; Porreca and Hruby, (2003) Pain 407-419; Servin, (2003) Advances in Experimental Medicine and Biology 523:245-260; Gilbert, Hosztafi, Mahurter and Pasternak, (2004) European Journal of Pharmacology 492:123-130).

Inflammatory Pain
(Gutstein and Akil, J. G. Hardman and L. E. Limbird (2001) The pharmacological basis of therapeutics 569-619).

Immune Function
(Renaud and Tomer, (1996) Advances in Experimental Medicine and Biology 402:63-69; Sacerdote, Bianchi, Manfredi and Panerai, (1997) Pain 72:325-330; Carrigan, Saurer, Ijames and Lysle, (2004) International Immunopharmacology 4:419-428).

Visceral Pain
(Kharkevich and Churukanov, (1999) European Journal of Pharmacology 375:121-131; Gebhart, (2000) Regional Anesthesia and Pain Medicine 25:632-638; Churukanov, (2003) Eksperimental'naya i Klinicheskaya Farmakologiya 66:24-31).

Esophageal Reflux
(Tonini, de Giorgio and de Ponti, (2004) Drugs 64:347-361).

Muscle Pain
Nielsen, Mathiesen and Blackburn-Munro, (2004) European Journal of Pharmacology 487:93-103).

Cancer Pain
9Gutstein and Akil, J. G. Hardman and L. E. Limbird (2001) The pharmacological basis of therapeutics 569-619; Wells, Bartlett, Ananthan and Bilsky, (2001) Journal of Pharmacology and Experimental Therapeutics 297:597-605; Valenzano, Miller, Chen, Shan, Crumley, Victory, Davies, Huang, Allie, Nolan, Rotshteyn, Kyle and Brogle, (2004) Journal of Pharmacology and Experimental Therapeutics 310:783-792).

Cough
(Gutstein and Akil, J. G. Hardman and L. E. Limbird (2001) The pharmacological basis of therapeutics 569-619).

Example 8

Delta, Mu Analgesic Synergy

Delta and mu opioid agonists have been repeatedly demonstrated to produce antinociceptive synergy. (Vaught and Takemori, (1979) Journal of Pharmacology and Experimental Therapeutics 211:280-3; Vaught and Takemori, (1979) Journal of Pharmacology and Experimental Therapeutics 208:86-90; Porreca, Jiang and Tallarida, (1990) European Journal of Pharmacology 179:463-8; Sufters, Miakowski, Taiwo and Levine, (1990) Brain Research 530:290-4; Horan, Tallarida, Haaseth, Matsunaga, Hruby and Porreca, (1992) Life Sciences 50:1535-41; Malmberg and Yaksh, (1992) Journal of Pharmacology and Experimental Therapeutics 263:264-75; Adams, Tallarida, Geller and Adler, (1993) Journal of Pharmacology and Experimental Therapeutics 266:1261-7; Dykstra, Schoenbaum, Yarbrough, McNutt and Chang, (1993) Journal of Pharmacology and Experimental Therapeutics 267:875-82; Rossi, Pasternak and Bodnar, (1994) Brain Research 665:85-93; Negri, Improta, Lattanzi, Potenza, Luchetti and Melchiorri, (1995) British Journal of Pharmacology 116:2931-8; Dykstra, Granger, Allen, Zhang and Rice, (2002) Psychopharmacology (Berlin, Germany) 163: 420-429).

Example 9

Delta, Mu Reduced Side Effect Profile

Combinations of delta and mu opioid agonists have demonstrated reduced side effect profiles including fewer convulsions, lower incidence of straub tail, and attenuated respiratory depression (O'Neill, Collins, Pettit, McNutt and Chang, (1997) Journal of Pharmacology and Experimental Therapeutics 282:271-277; Su, McNutt and Chang, (1998) Journal of Pharmacology and Experimental Therapeutics 287:815-823).

Therefore compounds dually embodying delta and mu opioid pharmacologies will have greater analgesic action and a reduced side effect profile than that derived from either sole pharmacology.

The invention claimed is:
1. A compound of Formula 1

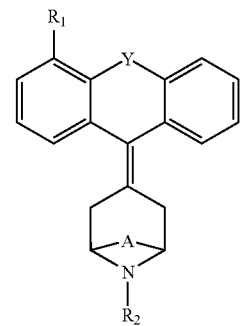

Formula (I)

wherein:
$R_1$ is hydroxy, aminocarbonyl, hydroxyamidino, formylamino; $C_{1-4}$alkanylaminocarbonyl; phenyl-aminocarbonyl; phenyl($C_{1-4}$)alkanylaminocarbonyl; and naphthyl- and phenyl- amino wherein the naphthyl and phenyl are optionally substituted with one to two substitutents independently selected from the group consisting of $C_{1-4}$alkanyl, $C_{1-4}$alkoxy, halogen, and hydroxy; or pyridinylamino;

$R_2$ is selected from the group consisting of hydrogen, $C_{1-4}$alkanyl, $C_{2-8}$alkenyl, $C_{2-8}$alkynyl, $C_{3-8}$cycloalkanyl ($C_{1-4}$)alkanyl, $C_{1-4}$alkanyloxy($C_{1-4}$)alkanyl, $C_{1-4}$alkanylthio($C_{1-4}$)alkanyl, hydroxy$C_{1-4}$alkanyl, thioformyl, phenylimino($C_{1-4}$)alkanyl, phenyl($C_{1-4}$)alkanyl, and heteroaryl($C_{1-4}$)alkanyl wherein heteroaryl is selected from the group consisting of benzo [1,3 ]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, benzothiophenyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form —O(CH$_2$)$_{1-3}$O—;
A is —(CH$_2$)$_2$—;
Y is O;
and enantiomers, diastereomers, tautomers, or pharmaceutically acceptable salts thereof.

2. The compound of claim 1 wherein:
R$_1$ is hydroxy, aminocarbonyl, formylamino; phenyl-aminocarbonyl; or pyridinylamino;
R$_2$ is selected from the group consisting of hydrogen, methyl, allyl, 2-methyl-allyl, 3-methyl-but-2-enyl, propynyl, hydroxyethyl, C$_{3-5}$ cycloalkanylmethyl, methylthioethyl, methoxyethyl, thioformyl, phenyliminomethyl, phenethyl, and heteroaryl(C$_{1-2}$)alkanyl wherein the heteroaryl is selected from the group consisting of benzo[1,3] dioxolyl, imidazolyl, furanyl, pyridinyl, thienyl, pyrimidinyl, pyrrolyl, quinolinyl, isoquinolinyl, benzothiophenyl, tetrazolyl; wherein the phenyl in any phenyl-containing substituent and the pyridinyl substituent are optionally substituted with one hydroxyl group;
and enantiomers, diastereomers, tautomers, or pharmaceutically acceptable salts thereof.

3. The compound of claim 1 wherein:
R$_1$ is hydroxy, aminocarbonyl, formylamino; phenyl-aminocarbonyl; or phenyl(C$_{1-4}$)alkanylaminocarbonyl;
R$_2$ is hydrogen, methyl, allyl, 3-methyl-but-2-enyl, cyclopropylmethyl, phenylmethyl, or heteroarylmethyl wherein heteroaryl is selected from the group consisting of benzo [1,3] dioxolyl, imidazolyl, furanyl, pyridinyl, and thienyl;
and enantiomers, diastereomers, tautomers, or pharmaceutically acceptable salts thereof.

4. The compound of claim 3 wherein:
R$_1$ is hydroxy, aminocarbonyl, formylamino; phenyl-aminocarbonyl; or phenylmethylaminocarbonyl;
R$_2$ is hydrogen, methyl, 3-methyl-but-2-enyl, cyclopropylmethyl, phenylmethyl, pyridin-2-ylmethyl, pyridin-3-ylmethyl, pyridin-4-ylmethyl, 2-hydroxy-pyridine-4-ylmethyl, imidazol-2-ylmethyl, thien-2-ylmethyl, or furan-3-ylmethyl;
and enantiomers, diastereomers, tautomers, or pharmaceutically acceptable salts thereof.

5. A compound of Formula (Ia)

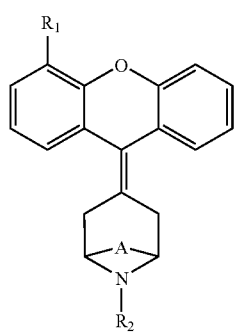

Formula (Ia)

selected from the group consisting of
a compound of Formula (Ia) wherein R$_1$ is methoxy, A is —(CH$_2$)$_2$—, and R$_2$ is H;
a compound of Formula (Ia) wherein R$_1$ is hydroxy, A is —(CH$_2$)$_2$—, and R$_2$ is H;
a compound of Formula (Ia) wherein R$_1$ is aminocarbonyl, A is —(CH$_2$)$_2$—, and R$_2$ is H;
a compound of Formula (Ia) wherein R$_1$ is aminocarbonyl, A is —(CH$_2$)$_2$—, and R$_2$ is furan-2-ylmethyl;
Enant. A, a compound of Formula (Ia) wherein R$_1$ is hydroxy, A is —(CH$_2$)$_2$—, and R$_2$ is trifluoromethylcarbonyl;
Enant. B, a compound of Formula (Ia) wherein R$_1$ is hydroxy, A is —(CH$_2$)$_2$—, and R$_2$ is trifluoromethylcarbonyl;
a compound of Formula (Ia) wherein R$_1$ is hydroxy, A is —(CH$_2$)$_2$—, and R$_2$ is H;
a compound of Formula (Ia) wherein R$_1$ is hydroxy, A is —(CH$_2$)$_2$—, and R$_2$ is H;
a compound of Formula (Ia) wherein R$_1$ is methylaminocarbonyl, A is —(CH$_2$)$_2$—, and R$_2$ is H;
a compound of Formula (Ia) wherein R$_1$ is dimethylaminocarbonyl, A is —(CH$_2$)$_2$—, and R$_2$ is H;
a compound of Formula (Ia) wherein R$_1$ is phenyl-aminocarbonyl, A is —(CH$_2$)$_2$-, and R$_2$ is H;
a compound of Formula (Ia) wherein R$_1$ is phenylmethyl-aminocarbonyl, A is —(CH$_2$)$_2$-, and R$_2$ is H;
a compound of Formula (Ia) wherein R$_1$ is phenylethyl-aminocarbonyl, A is —(CH$_2$)$_2$-, and R$_2$ is H;
a compound of Formula (Ia) wherein R$_1$ is (2-dimethylamino-ethyl) aminocarbonyl, A is —(CH$_2$)$_2$—, and R$_2$ is H;
a compound of Formula (Ia) wherein R$_1$ is hydroxy, A is —(CH$_2$)$_2$—, and R$_2$ is methyl;
a compound of Formula (Ia) wherein R$_1$ is hydroxy, A is —(CH$_2$)$_2$—, and R$_2$ is pyridin-2-ylmethyl;
a compound of Formula (Ia) wherein R$_1$ is hydroxy, A is —(CH$_2$)$_2$—, and R$_2$ is pyridin-4-ylmethyl;
a compound of Formula (Ia) wherein R$_1$ is hydroxy, A is —(CH$_2$)$_2$—, and R$_2$ is 2-hydroxy-pyridin-4-ylmethyl;
a compound of Formula (Ia) wherein R$_1$ is hydroxy, A is —(CH$_2$)$_2$—, and R$_2$ is thien-2-ylmethyl;
a compound of Formula (Ia) wherein R$_1$ is hydroxy, A is —(CH$_2$)$_2$—, and R$_2$ is furan-3-ylmethyl;
a compound of Formula (Ia) wherein R$_1$ is hydroxy, A is —(CH$_2$)$_2$—, and R$_2$ is cyclopropylmethyl;
a compound of Formula (Ia) wherein R$_1$ is hydroxy, A is —(CH$_2$)$_2$—, and R$_2$ is 2-methyl-but-2-enyl;
a compound of Formula (Ia) wherein R$_1$ is hydroxy, A is —(CH$_2$)$_2$—, and R$_2$ is 2-phenyl-imidazol-4-ylmethyl;
a compound of Formula (Ia) wherein R$_1$ is aminocarbonyl, A is —(CH$_2$)$_2$—, and R$_2$ is trifluoromethylcarbonyl
a compound of Formula (Ia) wherein R$_1$ is hydroxy, A is —(CH$_2$)$_2$—, and R$_2$ is phenethyl;
a compound of Formula (Ia) wherein R$_1$ is hydroxy, A is —(CH$_2$)$_2$—, and R$_2$ is pyridin-2-ylmethyl;
a compound of Formula (Ia) wherein R$_1$ is hydroxy, A is —(CH$_2$)$_2$—, and R$_2$ is phenylmethyl;
a compound of Formula (Ia) wherein R$_1$ is hydroxy, A is —(CH$_2$)$_2$—, and R$_2$ is benzothien-3-ylmethyl;
a compound of Formula (Ia) wherein R$_1$ is hydroxy, A is —(CH$_2$)$_2$—, and R$_2$ is 1H-imidazol-2-ylmethyl;
a compound of Formula (Ia) wherein R$_1$ is hydroxy, A is —(CH$_2$)$_2$—, and R$_2$ is isoquinolin-5-ylmethyl;
Enant. A, a compound of Formula (Ia) wherein R$_1$ is aminocarbonyl, A is —(CH$_2$)$_2$—, and R$_2$ is trifluoromethylcarbonyl;
Enant. A, a compound of Formula (Ia) wherein R$_1$ is aminocarbonyl, A is —(CH$_2$)$_2$—, and R$_2$ is H;
Enant. B, a compound of Formula (Ia) wherein R$_1$ is aminocarbonyl, A is —(CH$_2$)$_2$—, and R$_2$ is trifluoromethylcarbonyl;

Enant. A, a compound of Formula (Ia) wherein $R_1$ is aminocarbonyl, A is —$(CH_2)_2$—, and $R_2$ is H;
a compound of Formula (Ia) wherein $R_1$ is amino, A is —$(CH_2)_2$—, and $R_2$ is H;
Enant. A, a compound of Formula (Ia) wherein $R_1$ is hydroxyamidino, A is —$(CH_2)_2$—, and $R_2$ is H;
a compound of Formula (Ia) wherein $R_1$ is formylamino, A is —$(CH_2)_2$—, and $R_2$ is H;
Enant. A, a compound of Formula (Ia) wherein $R_1$ is hydroxy, A is —$(CH_2)_2$—, and $R_2$ is phenylmethyl;
Enant. B, a compound of Formula (Ia) wherein $R_1$ is hydroxy, A is —$(CH_2)_2$—, and $R_2$ is phenylmethyl;
a compound of Formula (Ia) wherein $R_1$ is phenylaminocarbonyl, A is —$(CH_2)_2$—, and $R_2$ is H;
a compound of Formula (Ia) wherein $R_1$ is phenylaminocarbonyl, A is —$(CH_2)_2$—, and $R_2$ is H;
Enant. A, a compound of Formula (Ia) wherein $R_1$ is hydroxy, A is —$(CH_2)_2$—, and $R_2$ is pyridin-3-ylmethyl;
Enant. B, a compound of Formula (Ia) wherein $R_1$ is hydroxy, A is —$(CH_2)_2$—, and $R_2$ is pyridin-3-ylmethyl;
Enant. A, a compound of Formula (Ia) wherein $R_1$ is hydroxy, A is —$(CH_2)_2$—, and $R_2$ is methyl;
Enant. B, a compound of Formula (Ia) wherein $R_1$ is hydroxy, A is —$(CH_2)_2$—, and $R_2$ is methyl;
Enant. A, a compound of Formula (Ia) wherein $R_1$ is phenylmethylaminocarbonyl, A is —$(CH_2)_2$—, and $R_2$ is H;
Enant. B, a compound of Formula (Ia) wherein $R_1$ is phenylmethylaminocarbonyl, A is —$(CH_2)_2$—, and $R_2$ is H;
Enant. A, a compound of Formula (Ia) wherein $R_1$ is phenethylaminocarbonyl, A is —$(CH_2)_2$—, and $R_2$ is H;
Enant. B, a compound of Formula (Ia) wherein $R_1$ is phenethylaminocarbonyl, A is —$(CH_2)_2$—, and $R_2$ is H;
Enant. B, a compound of Formula (Ia) wherein $R_1$ is hydroxy, A is —$(CH_2)_2$—, and $R_2$ is furan-3-ylmethyl;
Enant. A, a compound of Formula (Ia) wherein $R_1$ is hydroxy, A is —$(CH_2)_2$—, and $R_2$ is furan-3-ylmethyl;
Enant. A, a compound of Formula (Ia) wherein $R_1$ is hydroxy, A is —$(CH_2)_2$—, and $R_2$ is pyridin-2-ylmethyl;
Enant. B, a compound of Formula (Ia) wherein $R_1$ is hydroxy, A is —$(CH_2)_2$—, and $R_2$ is pyridin-2-ylmethyl;
a compound of Formula (Ia) wherein $R_1$ is 4-chiorophenylamino, A is —$(CH_2)_2$—, and $R_2$ is H;
a compound of Formula (Ia) wherein $R_1$ is pyridin-3-ylamino, A is —$(CH_2)_2$—, and $R_2$ is H; and
a compound of Formula (Ia) wherein $R_1$ is phenylamino, A is —$(CH_2)_2$—, and $R_2$ is H.

6. A composition comprising the (+) enantiomer of a compound of claim 1 wherein said composition is substantially free from the (−) isomer of said compound.

7. A composition comprising the (−) enantiomer of a compound of claim 1 wherein said composition is substantially free from the (+) isomer of said compound.

8. A pharmaceutical composition comprising a compound or salt according to claim 1 admixed with a pharmaceutically acceptable carrier, excipient or diluent.

9. A veterinary composition comprising a compound or salt according to claim 1 admixed with a veterinarily acceptable carrier, excipient or diluent.

10. A pharmaceutical composition comprising a compound or salt according to claim 1 admixed with a pharmaceutically acceptable carrier, excipient or diluent.

11. A veterinary composition comprising a compound or salt according to claim 1 admixed with a veterinarily acceptable carrier, excipient or diluent.

12. A pharmaceutical composition comprising a compound or salt according to claim 2 admixed with a pharmaceutically acceptable carrier, excipient or diluent.

13. A veterinary composition comprising a compound or salt according to claim 2 admixed with a veterinarily acceptable carrier, excipient or diluent.

14. A pharmaceutical composition comprising a compound or salt according to claim 3 admixed with a pharmaceutically acceptable carrier, excipient or diluent.

15. A veterinary composition comprising a compound or salt according to claim 3 admixed with a veterinarily acceptable carrier, excipient or diluent.

16. A pharmaceutical composition comprising a compound or salt according to claim 4 admixed with a pharmaceutically acceptable carrier, excipient or diluent.

17. A veterinary composition comprising a compound or salt according to claim 4 admixed with a veterinarily acceptable carrier, excipient or diluent.

* * * * *